United States Patent
Adedokun et al.

(10) Patent No.: US 12,138,295 B2
(45) Date of Patent: *Nov. 12, 2024

(54) METHODS OF TREATING CROHN'S DISEASE WITH ANTI-IL23 SPECIFIC ANTIBODY

(71) Applicant: Janssen Biotech, Inc., Horsham, PA (US)

(72) Inventors: Omoniyi Adedokun, Phoenixville, PA (US); Daphne Chan, Abington, PA (US); Yang Chen, Ambler, PA (US); Philippe Szapary, Wynnewood, PA (US)

( * ) Notice: Subject to any disclaimer, the term of this patent is extended or adjusted under 35 U.S.C. 154(b) by 558 days.

This patent is subject to a terminal disclaimer.

(21) Appl. No.: 17/212,424

(22) Filed: Mar. 25, 2021

(65) Prior Publication Data

US 2021/0308220 A1 Oct. 7, 2021

Related U.S. Application Data

(63) Continuation of application No. 16/291,310, filed on Mar. 4, 2019, now abandoned.

(60) Provisional application No. 62/638,624, filed on Mar. 5, 2018.

(51) Int. Cl.
| | | |
|---|---|---|
| A61K 38/17 | (2006.01) | |
| A61K 39/00 | (2006.01) | |
| A61P 1/00 | (2006.01) | |
| A61P 37/06 | (2006.01) | |
| C07K 16/24 | (2006.01) | |

(52) U.S. Cl.
CPC ............ *A61K 38/1793* (2013.01); *A61P 1/00* (2018.01); *A61P 37/06* (2018.01); *C07K 16/244* (2013.01); *A61K 2039/505* (2013.01); *A61K 2039/545* (2013.01); *A61K 2039/57* (2013.01); *C07K 2317/76* (2013.01)

(58) Field of Classification Search
None
See application file for complete search history.

(56) References Cited

U.S. PATENT DOCUMENTS

| | | |
|---|---|---|
| 4,309,989 A | 1/1982 | Fahim |
| 4,399,216 A | 8/1983 | Axel |
| 4,634,665 A | 1/1987 | Axel |
| 4,656,134 A | 4/1987 | Ringold |
| 4,676,980 A | 6/1987 | Segal |
| 4,683,195 A | 7/1987 | Mullis |
| 4,683,202 A | 7/1987 | Mullis |
| 4,704,692 A | 11/1987 | Ladner |
| 4,766,067 A | 8/1988 | Biswas |
| 4,767,402 A | 8/1988 | Kost |
| 4,795,699 A | 1/1989 | Tabor |
| 4,800,159 A | 1/1989 | Mullis |
| 4,816,567 A | 3/1989 | Cabilly |
| 4,873,316 A | 10/1989 | Meade |
| 4,889,818 A | 12/1989 | Gelfand |
| 4,921,794 A | 5/1990 | Tabor |
| 4,939,666 A | 7/1990 | Hardman |
| 4,946,778 A | 8/1990 | Ladner |
| 4,956,288 A | 9/1990 | Barsoum |
| 4,965,188 A | 10/1990 | Mullis |
| 4,994,370 A | 2/1991 | Silver |
| 5,066,584 A | 11/1991 | Gyllensten |
| 5,091,310 A | 2/1992 | Innis |
| 5,122,464 A | 6/1992 | Wilson |
| 5,130,238 A | 7/1992 | Malek |
| 5,142,033 A | 8/1992 | Innis |
| 5,149,636 A | 9/1992 | Axel |
| 5,168,062 A | 12/1992 | Stinski |
| 5,179,017 A | 1/1993 | Axel |
| 5,223,409 A | 6/1993 | Ladner |
| 5,225,539 A | 7/1993 | Winter |
| 5,260,203 A | 11/1993 | Ladner |
| 5,266,491 A | 11/1993 | Nagata |
| 5,304,489 A | 4/1994 | Rosen |
| 5,385,839 A | 1/1995 | Stinski |
| 5,403,484 A | 4/1995 | Ladner |
| 5,427,908 A | 6/1995 | Dower |
| 5,455,030 A | 10/1995 | Ladner |
| 5,496,549 A | 3/1996 | Yamazaki |
| 5,518,889 A | 5/1996 | Ladner |
| 5,530,101 A | 6/1996 | Queen |
| 5,534,621 A | 7/1996 | Ladner |
| 5,545,806 A | 8/1996 | Lonberg |
| 5,545,807 A | 8/1996 | Surani |
| 5,565,362 A | 10/1996 | Rosen |
| 5,569,825 A | 10/1996 | Lonberg |
| 5,571,698 A | 11/1996 | Ladner |
| 5,576,195 A | 11/1996 | Robinson |
| 5,580,717 A | 12/1996 | Dower |

(Continued)

FOREIGN PATENT DOCUMENTS

| | | |
|---|---|---|
| EP | 0003089 | 7/1979 |
| EP | 229246 | 10/1986 |

(Continued)

OTHER PUBLICATIONS

US 5,733,746 A, 03/1998, Treco (withdrawn)
Boehringer Ingelheim & Abbvie press release,"IL-23 inhibitor risankizumab induces remission in phase II study in patients with moderate-to-severe Crohn's disease"; news.abbvie.com/news/il-23-inhibitor-risankizumab-induces-remission-in-phase-ii-study-in-patients-with-moderate-to-severe-crohns-disease.htm; May 2016.*
Feagan et al, (Lancet; Apr. 29, 2017; vol. 389, pp. 1699-1709).*
Sandborn et al, (Gastroenterology 2022;162:1650-1664).*
Matteo Menga, Anna Balato, Annunziata Raimondo and Nicola Balato (2018) Guselkumab for the treatment of psoriasis, Expert Opinion on Biological Therapy, 18:4, 459-468, DOI: 10.1080/14712598.2018.1445223. Published online Mar. 3, 2018. (Year: 2018).*

(Continued)

*Primary Examiner* — Daniel E Kolker
*Assistant Examiner* — Hilary Ann Petrash
(74) *Attorney, Agent, or Firm* — Riverside Law LLP

(57) ABSTRACT

A method of treating Crohn's disease in a patient administers an IL-23 specific antibody, e.g., guselkumab, at an initial intravenous dose and subsequence subcutaneous doses.

15 Claims, No Drawings

Specification includes a Sequence Listing.

(56) References Cited

U.S. PATENT DOCUMENTS

| | | |
|---|---|---|
| 5,580,734 A | 12/1996 | Treco |
| 5,582,996 A | 12/1996 | Curtis |
| 5,585,089 A | 12/1996 | Queen |
| 5,595,898 A | 1/1997 | Robinson |
| 5,601,819 A | 2/1997 | Wong |
| 5,618,920 A | 4/1997 | Robinson |
| 5,625,126 A | 4/1997 | Lonberg |
| 5,625,825 A | 4/1997 | Rostoker |
| 5,627,052 A | 5/1997 | Schrader |
| 5,633,425 A | 5/1997 | Lonberg |
| 5,641,670 A | 6/1997 | Treco |
| 5,643,759 A | 7/1997 | Pfreundschuh |
| 5,643,768 A | 7/1997 | Kawasaki |
| 5,656,730 A | 8/1997 | Lee |
| 5,658,754 A | 8/1997 | Kawasaki |
| 5,661,016 A | 8/1997 | Lonberg |
| 5,693,493 A | 12/1997 | Robinson |
| 5,693,762 A | 12/1997 | Queen |
| 5,698,417 A | 12/1997 | Robinson |
| 5,698,435 A | 12/1997 | Robinson |
| 5,714,352 A | 2/1998 | Jakobobits |
| 5,723,323 A | 3/1998 | Kauffman |
| 5,733,761 A | 3/1998 | Treco |
| 5,750,373 A | 5/1998 | Garrard |
| 5,763,192 A | 6/1998 | Kauffman |
| 5,763,733 A | 6/1998 | Whitlow |
| 5,766,886 A | 6/1998 | Studnicka |
| 5,767,260 A | 6/1998 | Whitlow |
| 5,770,359 A | 6/1998 | Wilson |
| 5,770,428 A | 6/1998 | Boris-Lawrie |
| 5,789,650 A | 8/1998 | Lonberg |
| 5,807,706 A | 9/1998 | Carter |
| 5,814,476 A | 9/1998 | Kauffman |
| 5,817,483 A | 10/1998 | Kauffman |
| 5,821,333 A | 10/1998 | Carter |
| 5,824,514 A | 10/1998 | Kauffman |
| 5,827,690 A | 10/1998 | Meade |
| 5,827,739 A | 10/1998 | Wilson |
| 5,833,985 A | 11/1998 | Ball |
| 5,837,500 A | 11/1998 | Ladner |
| 5,839,446 A | 11/1998 | Waner |
| 5,849,992 A | 12/1998 | Meade |
| 5,851,198 A | 12/1998 | Castellano |
| 5,856,456 A | 1/1999 | Whitlow |
| 5,859,205 A | 1/1999 | Adair |
| 5,885,793 A | 3/1999 | Griffiths |
| 5,932,448 A | 8/1999 | Tso |
| 5,959,083 A | 9/1999 | Bosslet |
| 5,959,084 A | 9/1999 | Ring |
| 5,962,255 A | 10/1999 | Griffiths |
| 5,976,862 A | 11/1999 | Kauffman |
| 5,989,530 A | 11/1999 | Lorenz |
| 5,994,616 A | 11/1999 | Rosen |
| 6,010,902 A | 1/2000 | Ledbetter |
| 6,037,453 A | 3/2000 | Jardieu |
| 6,060,284 A | 5/2000 | Bazan |
| 6,060,285 A | 5/2000 | Lenz |
| 6,106,833 A | 8/2000 | Ring |
| 6,132,992 A | 10/2000 | Ledbetter |
| 6,180,370 B1 | 1/2001 | Queen |
| 6,193,967 B1 | 2/2001 | Morganelli |
| 6,204,023 B1 | 3/2001 | Robinson |
| 6,210,668 B1 | 4/2001 | Lindhofer |
| 6,479,634 B1 | 11/2002 | Bazan |
| 6,495,667 B1 | 12/2002 | Bazan |
| 6,610,285 B1 | 8/2003 | Hirata |
| 6,756,481 B2 | 6/2004 | Chirica |
| 6,800,460 B1 | 10/2004 | Oppmann |
| 6,835,825 B1 | 12/2004 | Bazan |
| RE39,015 E | 3/2006 | Bazan |
| 7,090,847 B1 | 8/2006 | Oppmann |
| 7,183,382 B2 | 2/2007 | Oppmann |
| 7,247,711 B2 | 7/2007 | Benson |
| 7,252,971 B2 | 8/2007 | Benson |
| 7,282,204 B2 | 10/2007 | Oft |
| 7,491,391 B2 | 2/2009 | Benson |
| 7,807,414 B2 | 10/2010 | Benson |
| 7,935,344 B2* | 5/2011 | Benson ............... A61P 35/00 424/145.1 |
| 7,993,645 B2 | 8/2011 | Benson |
| 8,106,177 B2 | 1/2012 | Benson |
| 8,221,760 B2 | 7/2012 | Benson |
| 9,353,181 B2 | 5/2016 | Benson |
| 9,353,645 B1 | 5/2016 | Kennedy |
| 9,783,607 B2 | 10/2017 | Benson |
| 9,803,010 B2 | 10/2017 | Reichert |
| 10,030,070 B2 | 7/2018 | Benson |
| 11,780,911 B2* | 10/2023 | Germinaro ............ A61P 1/04 424/145.1 |
| 2002/0042386 A1 | 4/2002 | Rosen |
| 2003/0003097 A1 | 1/2003 | Reff |
| 2003/0124617 A1 | 7/2003 | Gram |
| 2003/0162261 A1 | 8/2003 | Oppmann |
| 2004/0185506 A1 | 9/2004 | Heavner |
| 2004/0258686 A1 | 12/2004 | Chirica |
| 2005/0049402 A1 | 3/2005 | Babcook |
| 2005/0053598 A1 | 3/2005 | Burke |
| 2005/0175611 A1 | 8/2005 | Mahler |
| 2005/0208052 A1 | 9/2005 | Katsikis |
| 2005/0244874 A1 | 11/2005 | Kastelein |
| 2007/0048315 A1 | 3/2007 | Presta |
| 2010/0322863 A1 | 12/2010 | Benson |
| 2011/0287028 A1 | 11/2011 | Benson |
| 2011/0319292 A1 | 12/2011 | Benson |
| 2015/0147337 A1 | 5/2015 | Reichert |
| 2016/0237151 A1 | 8/2016 | Benson |
| 2017/0081402 A1* | 3/2017 | Boecher ............. A61P 1/04 |
| 2017/0107266 A1 | 4/2017 | Hinner |
| 2018/0036379 A1* | 2/2018 | Chevrier ............. A61P 29/00 |
| 2018/0094052 A1 | 4/2018 | Randazzo |
| 2018/0218215 A1 | 8/2018 | Quenard |
| 2019/0246455 A1 | 8/2019 | Weber |
| 2019/0269757 A1 | 9/2019 | Adedokun |

FOREIGN PATENT DOCUMENTS

| | | |
|---|---|---|
| EP | 368684 | 5/1990 |
| EP | 371998 | 6/1990 |
| EP | 0438474 | 7/1991 |
| EP | 0463151 | 1/1992 |
| EP | 550400 | 7/1993 |
| EP | 0229046 B1 | 5/1994 |
| EP | 0710719 A1 | 5/1996 |
| EP | 0814259 | 12/1997 |
| GB | 2272440 A | 5/1994 |
| JP | 2009523012 | 6/2009 |
| JP | 2016505572 | 2/2016 |
| WO | 8605803 A1 | 10/1986 |
| WO | 8806630 A1 | 9/1988 |
| WO | 8906283 A1 | 7/1989 |
| WO | 9003809 A1 | 4/1990 |
| WO | 9004036 A1 | 4/1990 |
| WO | 1990005370 | 5/1990 |
| WO | 9014424 A1 | 11/1990 |
| WO | 9014430 A1 | 11/1990 |
| WO | 9014443 A1 | 11/1990 |
| WO | 9100360 A1 | 1/1991 |
| WO | 9117271 A1 | 11/1991 |
| WO | 9118980 A1 | 12/1991 |
| WO | 9119818 A1 | 12/1991 |
| WO | 9200373 A1 | 1/1992 |
| WO | 1992001047 A1 | 1/1992 |
| WO | 1992003461 | 3/1992 |
| WO | 9205258 A1 | 4/1992 |
| WO | 1992006204 | 4/1992 |
| WO | 1992011272 | 7/1992 |
| WO | 9214843 A1 | 9/1992 |
| WO | 9216221 A1 | 10/1992 |
| WO | 9218619 A1 | 10/1992 |
| WO | 1992020791 | 11/1992 |
| WO | 9308278 A1 | 4/1993 |
| WO | 1993006213 A1 | 4/1993 |
| WO | 9308829 A1 | 5/1993 |
| WO | 1993011236 A1 | 6/1993 |

(56) References Cited

FOREIGN PATENT DOCUMENTS

| WO | 1993019172 | A1 | 9/1993 |
|---|---|---|---|
| WO | 1994018219 | | 8/1994 |
| WO | 9425585 | A1 | 11/1994 |
| WO | 1995001438 | | 1/1995 |
| WO | 9516027 | A1 | 6/1995 |
| WO | 1995015388 | | 6/1995 |
| WO | 9607754 | A1 | 3/1996 |
| WO | 9613583 | A2 | 5/1996 |
| WO | 9619256 | A1 | 6/1996 |
| WO | 9634096 | A1 | 10/1996 |
| WO | 9708320 | A1 | 3/1997 |
| WO | 9713852 | A1 | 4/1997 |
| WO | 1997020032 | | 6/1997 |
| WO | 1998001757 | | 1/1998 |
| WO | 9824884 | A1 | 6/1998 |
| WO | 9824893 | A1 | 6/1998 |
| WO | 9850433 | A2 | 11/1998 |
| WO | 9853847 | A1 | 12/1998 |
| WO | 1999006834 | | 2/1999 |
| WO | 9954342 | A1 | 10/1999 |
| WO | 03011878 | A2 | 2/2003 |
| WO | 2007076524 | | 7/2007 |
| WO | 2014004436 | | 1/2014 |
| WO | 2014093203 | A1 | 6/2014 |
| WO | WO 2015/119841 | * | 8/2015 |
| WO | 2017048901 | | 3/2017 |
| WO | 2017049035 | | 3/2017 |
| WO | 2017172771 | | 10/2017 |

OTHER PUBLICATIONS

Langrish, et al., "IL-23 drives a pathogenic T cell population that induces autoimmune inflammation," Journal of Experimental Medicine, 201(20: 233-240 (2005).

Lee, et al., "Increased Expression of Interleukin 23 p19 and p40 in Lesional Skin of Patients with Psoriasis Vulgaris," Journal of Experimental Medicine, 199(1): 125-130 (2004).

Leonard, et al., "Prevention of experimental autoimmune encephalomyelitis by antibodies against interleukin 12," Journal of Experimental Medicine, 181(1): 381-386 (1995).

Lonberg et al. "Antigen-specific human antibodies from mice comprising four distinct genetic modifications", Nature, vol. 368 (1994), pp. 856-859.

Lonberg et al., "Human Antibodies from Transgenic Mice", International Reviews of Immunology, vol. 13, No. 1 (1995), pp. 65-93.

Ma et al., "Immunotherapeutic potential of antibodies produced in plants", Trends in Biotechnology, vol. 13 (1995), pp. 522-527.

Ma et al., "Plant Antibodies for Immunotherapy", Plant Physiology, vol. 109 (1995), pp. 341-346.

Maguire van Seventer, et al., "Interferon- differentially regulates expression of the IL-12 family members p35, p40, p19 and EB13 in activated human dendritic cells," Journal of Neuroimmunology, 133: 60-71 (2002).

Malfait, et al., "Blockade of IL-12 during the induction of collagen-induced arthritis (CIA) markedly attenuates the severity of the arthritis," Clinical and Experimental Immunology, 111:327-383 (1998).

Mendez, et al., "Functional transplant of megabase human immunoglobulin loci recapitulates human antibody response in mice," Nature Genetics, vol. 15, No. 2 (1997), pp. 146-156.

Milstein, et al., "Hybrid hybridomas and their Use in Immunohistochemistry," Nature, vol. 305 (1983), pp. 537-540.

Murphy, et al., "Divergent pro- and anti-inflammatory roles for IL-23 and IL-12 in Joint autoimmune inflammation," Journal of Experimental Medicine, 198(12): 1951-1957 (2003).

Needleman, S. & Wunsch, C, "A General Method Applicable to the Search for Similarities in the Amino Acid Sequence of Two Proteins.", J. Mol. Biol., 1970, pp. 443-453, vol. 48.

Nguyen et al., "Production of Human Monoclonal Antibodies in SCID Mouse", Microbiology and Immunology, vol. 41 (1997), pp. 901-907.

Oppmann, et al., "Novel p19 Protein Engages IL-12p40 to Form a Cytokine, IL-23, with Biological Activities Similar as Well as Distinct from IL-12," Immunity, 13: 715-725 (2000).

Panaccione et al; "Briakinumab for Treatment of Crohn's Disease: Results of a Randomized Trial." Inflammatory Bowel Disease, vol. 21, No. 6, Jun. 2015, pp. 1329-1340.

Parham, et al., "A Receptor for the Heterodimeric Cytokine IL-23 is Composed of IL-12R 1 and a Novel Cytokine Receptor Subunit, IL-23R," The Journal of Immunology, 168: 5699-5708 (2002).

Peter J. Barnes, "Cytokine-directed therapies for the treatment of chronic airway diseases," Cytokine & Growth Factor Reviews 14 (2003): 511-522 (2003).

Portolano, et al., "Lack of Promiscuity in Autoantigen-Specific H and L Chain Combinations as Revealed by Human H and L Chain 'Roulette'," Journal of Immunology, 150(3): 880-887 (1993).

Powell et al., "Gel Microdroplets and Flow Cytometry: Rapid Determination of Antibody Secretion by Individual Cells Within a Cell Population", Biotechnology, vol. 8 (1990), pp. 333-337.

Presky et al., "A functional interleukin 12 receptor complex is composed of two beta-type cytokine receptor subunits," Proceedings of the National Academy of Science USA, 93(24): 14002-14007 (1996).

Presta, et al., "Humanization of an antibody y directed against IgE," Journal of Immunology, 151: 2623-2632 (1993).

Ramos et al; "Targeting Specific Immunologic Pathways in Crohn's Disease." Gatroenterol Clin N Am, Sep. 2017, vol. 46, No. 3, pp. 577-588.

Riechmann, et al., "Reshaping human antibodies for therapy," Nature, vol. 332 (1988), pp. 323-327.

Sandhu et al., "The Use of SCID Mice in Biotechnology and as a Model for Human Disease", Critical Reviews in Biotechnology, vol. 16 (1996), pp. 95-118.

Schmidt, et al., Expression of Interleukin-12-Related Cytokine Transcripts in Inflammatory Bowel Disease: Elevated Interleukin-23p19 and Interneukin-27p28 in Crohn's Disease but Not in Ulcerative Colitis, 11: 16-23 (2005).

Shields, et al., "High Resolution Mapping of the Binding Site onHuman IgFI for FOyRI, FCyRII, FCyRIII, and RcRn and Design of IgGI Variants with Improved Binding to the RCyR," The Journal of Biological Chemistry, 276(9): 6591-6604 (2001).

Sims et al., "A Humanized CD18 Antibody Can Block Function without Cell Destruction", Journal of Immunology, vol. 151 (1993), p. 2296.

Smith, et al., "Human Interleukin 4: The Solution Structure of a Four-helix Bundle Protein", Journal of Molecular Biology, vol. 224 (1992), pp. 899-904.

Sofen, et al., "Guselkumab (an IL-23-specific mAb) demonstrates clinical and molecular response in patients with moderate-to-severe psoriasis," Journal of Allergy and Clinical Immunology, 133(4): 1032-1040 (2014).

Sofen, et al., "Results of a single ascending dose study to assess the safety and tolerability of CNTO1959 following intravenous or subcutaneous administration in healthy subjects and in subjects with moderate to severe psoriasis," British Journal of Dermatology, Abstract FC-21 (2011). Abstract only.

Sprague, et al., "Expression of a Recombinant DNA Gene Coding for the Vesiclar Stomatitis Virus Nucleocapsid Protein", Journal of Virology, vol. 45 (1983), pp. 773-781.

Steenbakkers et al., "Efficient generation of monoclonal antibodies from preselected antigen-specific B", Molecular Biology Reports, vol. 19 (1994), pp. 125-134.

Suresh et al., "Bispecific Monoclonal Antibodies from Hybrid Hybridomas", Methods in Enzymology 121:210 (1986).

Taylor et al., "A transgenic mouse that expresses a diversity of human sequence heavy and light chain immunoglobulins", Nucleic Acids Research, vol. 20, No. 23 (1992), pp. 6287-6295.

Taylor, et al., "Human immunoglobulin transgenes undergo rearrangement, somatic mutation and class switching in mice that lack endogenous IgM," International Immunology, vol. 6, No. 4 (1994), pp. 579-591.

Traunecker, et al., "Bispecific Single chain molecules (Janusins) target cytotoxic lymphocytes on HIV infected cells," EMBO Journal, 10(12): 3655-3659 (1991).

(56) References Cited

OTHER PUBLICATIONS

Trinchieri, et al., "The IL-12 Family of Heterodimeric Cytokines: New Players in the Regulation of T Cell Responses," Immunity, 19: 641-644 (2003).
Tuaillon et al., "Human immunoglobulin heavy-chain minilocus recombination in transgenic mice: Gene-segment use in u and y transcripts", Proc Natl Acad Sci USA, vol. 90, No. 8 (1993), pp. 3720-3724.
Umana, et al., "Engineered glycoforms of an anfineuro-blastoma IgGI with optimized antibody-dependent cellular cytotoxic activity," Nature Biotechnology, 17: 176-190 (1999).
Vajdos, et al., "Comprehensive Functional Maps of the Antigen-Binding Site of an Anti-ErbB2 Antibody Obtained with Shotgun Scanning Mutagenesis," Journal of Molecular Biology, 320(2): 415-428 (2002).
Verhoeyen et al., "Reshaping Human Antibodies:Grafting an Antilysozyme Activity", Science, vol. 239 (1988), p. 1534.
Visvanathan et al, "OP103 Selective IL-23 Inhibition by Risankizumab Modulates the Molecular Profile in the Colon of Active Crohn's Diseae Patients." United European Gastroenterology Journal; 4 (5S) A1-A156), Oct. 2016.
Werlen et al., "Site-Specific Conjugation of an Enzyme and an Antibody Fragment", Bioconjugate Chemistry, vol. 5 (1994), pp. 411-417.
Whitelam, et al., "Antibody production in transgenic plants," Biochemical Society Transactions, Transgenic Plants and Plan Biochemistry, vol. 22 (1994), pp. 940-944.
Wiekowski, et al., "Ubiquitous Transgenic Expression of the IL-23 Subunit p19 Induces Multiorgan Inflammation, Runting, Infertility, and Premature Death," Journal of Immunology, 166: 7563-7570 (2001).
Wiendl, et al., "Therapeutic Approaches in Multiple Sclerosis: Lessons from Failed and Interrupted Treatment Trials," BioDrugs, 16(3): 183-200 (2002).
Yadav, et al., "Cytokines and autoimmunity: redundancy defines their complex nature," Current Opinion in Immunology, 15: 697-703 (2003).
Aggarwal, et al., "Interleukin-23 Promotes a Distinct CD4 T Cell Activation State characterized by the Production of Interleukin-17," The Journal of Biological Chemistry, 278(3): 1910-1914 (2003).
Alex Hoffman, "Prefilled syringes point to the future," Beremans Limited, 1-4 (2004).
Altschul, et al., "Basic Local Alignment Search Tool," Journal of Molecular Biology, 215: 403-410 (1990).
Anonymous: "NCT03466411 A Study of the Efficacy and Safety of Guselkumab in Participants With Moderately to Severely Active Crohn's Disease (GALAXI)", None (earliest Version on record) 2 Mar. 30, 2018 Contacts/Locations Study Status, Contacts/Locations and Study Design 16 May 16, 2019 Contacts/Locations and Study Status 17 Jun. 13, 2019 Study Status and Contacts/Locations 18 Jul. 11, 2019 Study St, Feb. 21, 2019 (Feb. 21, 2019 ), pp. 1-28, XP055895303.
Babcook et al., "A novel strategy for generating monoclonal antibodies from single, isolated lymphocytes producing antibodies of defined specificities", Proc. Natl. Acad. Sci. USA , vol. 93 (1996), pp. 7843-7848.
Barrie, et al., "The interleukin-12 family of cytokines: Therapeutic targets for inflammatory disease mediation," Clinical and Applied Immunology Reviews, 5: 225-240 (1995).
Belladonna, et al., "IL-23 and IL-12 Have Overlapping, but Distinct, Effects on Murine Dendritic Cells," The Journal of Immunology, 168: 5448-5454 (2002).
Bhandari et al, "Discovery of Novel Oral Peptide Antagonists of IL-23 Receptor that are Efficacious in a Rat Model of IBD." Inflammatory Bowel Diseases, Mar. 2016, vol. 22, No. 1, abstract P-148.
Boehringer Ingelheim, May 2016. "IL-23 Inhibitor Risankizumab Induces Remission in Phase II Study in Patients with Moderate-to-Severe Crohn's Disease" 4 pages.

Capellas, et al., "Enzymatic Condensation of Cholecystokinin CCK-8 (4-6) and CCK-8 (7-8) Peptide Fragments in Organic Media," Biotechnology and Bioengineering, vol. 56, No. 4 (1997), pp. 456-463.
Carter, et al., "Humanization of an anfi-pISS™ 12 antibody for human Cancer therapy," Proceedings of the National Academy of Science USA, 89: 4285-4289 (1992).
Chothia, et al., "Canonical Structures for the Hypervariable Regions of Immunoglobulins", Journal of Molecular Biology, vol. 196 (1987), pp. 901-917.
Conrad et al., "Compartment-specific accumulation of recombinant immunoglobulins in plant cells: an essential tool for antibody production and immunomodulation of physiological functions and pathogen activity", Plant Molecular Biology, vol. 38 (1998), pp. 101-109.
Cramer et al., "Transgenic Plants for Therapeutic Proteins: Linking Upstream and Downstream Strategies", Current Topics in Microbiology and Immunology, vol. 240 (1999), pp. 95-118.
Cua, et al., "Interleukin-23 rather than interleukin-12 is the critical cytokine for autoimmune inflammation of the brain," Nature, 421: 744-748 (2003).
Cunningham and Wells, "High-Resolution Epitope Mapping of hGH-Receptor Interations by Alanine-Scanning Mutagenesis", Science Ausubel, supra, Chapters 8, 15; 244:1081-1085 (1989)).
David M. Frucht, "IL-23: A Cytokine That Acts on Memory T Cells," Science STKE, 114: 1-3 (2002).
Davidson, et al., "IL-12, But Not IFN-y, Plays a Major Role in Sustaining the Chronic Phase of Colitis inIL-10-DeficientMice," The Journal of Immunology, 161: 3143-3149 (1998).
De Vos, et al., "Human Growth Hormone and Extracellular Domain of Its Receptor: Crystal Structure of the Complex", Science, vol. 255 (1992), pp. 306-312.
Devereaux, et al., "A comprehensive set of sequence analysis programs for the VAX," Nucleic Acids Research, 12(1): 387-395 (1984).
Eduardo Padlan, "Anatomy of the Antibody Molecule," Molecular Immunology, 31(3): 169-217 (1994).
Elliott, M.J. et al., "A Repeated Therapy with Monoclonal Antibody to Tumour Necrosis Factor a (cA2) in Patients with Rheumatoid Arthritis", The Lancet, vol. 344 (1994), pp. 1125-1127.
Eren et al. "Human monoclonal antibodies specific to hepatitis B virus generated in a human/mouse radiation chimera: the Trimera system", Immunology, vol. 93 (1998), pp. 154-161.
Fan, et al., "Mixed treatment comparison of infliximab with ustekinumab in patients with moderate to severe psoriasis," British Journal of Dermatology, Abstract P-64 (2011). Abstract only.
Feagan et al, "Supplemental Material: Induction therapy with the selective interleukin-23 inhibitor risankizumab in patients with moderate-to-severe Crohn's disease: a randomised, double-blind, placebo-controlled phase 2 study" Lancet; Apr. 2017; vol. 389, pp. 1699-1709.
Fisch et al., "Site-Specific Modification of a Fragment of a Chimeric Monoclonal Antibody Using Reverse Proteolysis", Bioconjugate Chemistry, vol. 3 (1992), pp. 147-153.
Fischer et al., "Towards molecular farming in the future: moving from diagnostic protein and antibody production in microbes to plants", Biotechnology and Applied Biochemistry, vol. 30 (1999), pp. 101-108.
Fishwild et al., "High-avidity human IgGk monoclonal antibodies from a novel strain of minilocus transgenic mice", Nature Biotechnology, vol. 14, No. 7 (1996), pp. 845-851.
GenBank Accession No. AA418747, Hillier, et al., May 12, 1997. 3 pages.
GenBank Accession No. AA418955, Hillier, et al., May 12, 1997. 3 pages.
GenBank Accession No. AF301620, Oppmann, et al., Dec. 4, 2000. 2 pages.
GenBank Accession No. C06368, J. Takeda, Aug. 9, 1996. 2 pages.
Girolomoni G. et al: "The role of IL-23 and the IL-23/T H 17 immune axis in the pathogenesis and treatment of psoriasis", JEADV. Journal of the European Academy of Dermatology and Venereology., vol. 31, No. 10, Oct. 1, 2017 (Oct. 1, 2017 ), pp. 1616-1626.

(56) References Cited

OTHER PUBLICATIONS

Gray et al., "Secretion capture and report web: use of affinity derivatized agarose microdroplets for the selection of hybridoma cells", Journal of Immunological Methods, vol. 182 (1995), pp. 155-163.
Green et al, "Antigen-specific human monoclonal antibodies from mice engineered with human Ig heavy and light chain YACs", Nature Genetics, vol. 7 (1994), pp. 13-21.
Hanes et al. "Ribosome display efficiently selects and evolves high-affinity antibodies in vitro from immune libraries", Proc Natl. Aca. Sci USA, vol. 95 (1998), pp. 14130-14135.
Hanes et al., "In vitro selection and evolution of functional proteins by using ribosome display", Proc. Natl. Acad. Sci. USA, vol. 94 (1997), pp. 4937-4942.
Harlow, et al., Antibodies a Laboratory Manual, Cold Spring Harbor Laboratory, pp. 567-569 (1988).
Henikoff, et al., "Amino acid Substitution matrices from protein blocks," Proceedings of the National Academy of Sciences USA, 89: 10915-10919 (1992).
Hong, et al., IL-12, independently of IFN-gamma, plays a crucial role in the pathogenesis of a murine psoriasis-like skindisorder, Journal of Immunology, 162(12): 7480-7491 (1999).
Hood et al., "Molecular Farming of Industrial Proteins from Transgenic Maize", Advances in Experimental Medicine and Biology, vol. 464 (1999), pp. 127-147.
Hu, et al., "Information contributed by meta-analysis in exposure-response modeling: application to phase 2 dose selection of guselkumab in patients with moderate-to-severe Psoriasis", Journal of Pharmacokinetics and Pharmacodynamics, vol. 41, No. 3, pp. 239-250, (2014).
Itoh et al., "Application of Inverse Substrates to Trypsin-Catalyzed Peptide Synthesis", Bioorganic Chemistry, vol. 24, No. 1 (1996), pp. 59-68.
Jones, et al., "Replacing the complementarity-determining regions in a human antibody with those from a mouse," Nature, vol. 321 (1986), pp. 522-525.
Katsube, Y., et al., "Analysis of k light chain contribution to anti-DNA antibody activity of a human VH4-21-encoded monoclonal antibody (NE-1) by antibody-phage display technique", International Journal of Molecular Medicine, vol. 1, No. 5 (1998), pp. 863-868.
Kenny et al., "Production of Monoclonal Antiboodies Using a Secretion Capture Report Web", Bio/Technology, vol. 13 (1995), pp. 787-790.
Knappik, et al., "Fully Synthetic Human Combinatorial Antibody Libraries (HuCAL) Based on Modular Consensus Frameworks and CDRs Randomized with Trinucleotides," Journal of Molecular Biology, 296(1): 57-86 (2000).
Kretzschmar, et al., "Antibody discovery: phage display," Current Opinion in Biotechnology, 13: 598-602 (2002).
Krnjevic-Pezic, et al., "Our experience using ustekinumab in patients with plaque psoriasis," British Journal of Dermatology, Abstract P-24 (2011). Abstract only.
Kumaran et al., "Conformationally driven protease-catalyzed splicing of peptide segments: V8 protease-mediated synthesis of fragments derived from thermolysin and ribonuclease A", Protein Science, vol. 6, No. 10 (1997), pp. 2233-2241.
Feagan, Brian G., et al. "Ustekinumab as induction and maintenance therapy for Crohn's disease." New England journal of medicine 375.20 (2016): 1946-1960.
Sandborn et al. Efficacy and Safety of Mirikizumab in a Randomized Phase 2 Study of Patients With Ulcerative Colitis. Gastroenterology. Feb. 2020;158(3):537-549.e10 Epub Sep. 4, 2019.
Shi et al. The state of the art on treatment of Crohn's disease. J Gastroenterol (2018) 53:989-998.
Centocor Ortho Biotech Inc., Dec. 30, 2009 [retrieved on Jun. 13, 2019]. Retrieved from the Internet: <URL: https://www.accessdata.fda.gov/drugsatfda_docs/label/2009/125261s0011b1pdf>; pp. 1-12.
Cohen, BL et al., Update on anti-tumor necrosis factor agents and other new drugs for inflammatory bowel disease. BMJ. Jun. 19, 2017, vol. 357, No. J2505; abstract; DOI: 10.1136/bmi.j2505.

* cited by examiner

METHODS OF TREATING CROHN'S DISEASE WITH ANTI-IL23 SPECIFIC ANTIBODY

CROSS-REFERENCE TO RELATED APPLICATIONS

This application is a continuation of U.S. patent application Ser. No. 16/291,310, filed 4 Mar. 2019, which claims priority to U.S. Provisional Application Ser. No. 62/638,624, filed 5 Mar. 2018. The entire contents of the aforementioned applications are incorporated by reference in their entireties.

SEQUENCE LISTING

The instant application contains a Sequence Listing which has been submitted electronically in ASCII format and is hereby incorporated by reference in its entirety. Said ASCII copy, created on 1 Mar. 2019 is named JBI5153USNP1SEQLIST.txt and is 79,744 bytes in size.

FIELD OF THE INVENTION

The present invention concerns methods for treating Crohn's Disease with an antibody that binds the human IL-23 protein. In particular, it relates to dosing regimens for administration of an anti-IL-23 specific antibody and specific pharmaceutical compositions of an antibody, e.g., guselkumab.

BACKGROUND OF THE INVENTION

Interleukin (IL)-12 is a secreted heterodimeric cytokine comprised of 2 disulfide-linked glycosylated protein subunits, designated p35 and p40 for their approximate molecular weights. IL-12 is produced primarily by antigen-presenting cells and drives cell-mediated immunity by binding to a two-chain receptor complex that is expressed on the surface of T cells or natural killer (NK) cells. The IL-12 receptor beta-1 (IL-12Rβ1) chain binds to the p40 subunit of IL-12, providing the primary interaction between IL-12 and its receptor. However, it is IL-12p35 ligation of the second receptor chain, IL-12Rβ2, that confers intracellular signaling (e.g. STAT4 phosphorylation) and activation of the receptor-bearing cell (Presky et al, 1996). IL-12 signaling concurrent with antigen presentation is thought to invoke T cell differentiation towards the T helper 1 (Th1) phenotype, characterized by interferon gamma (IFNγ) production (Trinchieri, 2003). Th1 cells are believed to promote immunity to some intracellular pathogens, generate complement-fixing antibody isotypes, and contribute to tumor immunosurveillance. Thus, IL-12 is thought to be a significant component to host defense immune mechanisms.

It was discovered that the p40 protein subunit of IL-12 can also associate with a separate protein subunit, designated p19, to form a novel cytokine, IL-23 (Oppman et al, 2000). IL-23 also signals through a two-chain receptor complex. Since the p40 subunit is shared between IL-12 and IL-23, it follows that the IL-12Rβ1 chain is also shared between IL-12 and IL-23. However, it is the IL-23p19 ligation of the second component of the IL-23 receptor complex, IL-23R, that confers IL-23 specific intracellular signaling (e.g., STAT3 phosphorylation) and subsequent IL-17 production by T cells (Parham et al, 2002; Aggarwal et al. 2003). Recent studies have demonstrated that the biological functions of IL-23 are distinct from those of IL-12, despite the structural similarity between the two cytokines (Langrish et al, 2005).

Abnormal regulation of IL-12 and Th1 cell populations has been associated with many immune-mediated diseases since neutralization of IL-12 by antibodies is effective in treating animal models of psoriasis, multiple sclerosis (MS), rheumatoid arthritis, inflammatory bowel disease, insulin-dependent (type 1) diabetes mellitus, and uveitis (Leonard et al, 1995; Hong et al, 1999; Malfait et al, 1998; Davidson et al, 1998). However, since these studies targeted the shared p40 subunit, both IL-12 and IL-23 were neutralized in vivo. Therefore, it was unclear whether IL-12 or IL-23 was mediating disease, or if both cytokines needed to be inhibited to achieve disease suppression. Recent studies have confirmed through IL-23p19 deficient mice or specific antibody neutralization of IL-23 that IL-23 inhibition can provide equivalent benefit as anti-IL-12p40 strategies (Cua et al, 2003, Murphy et al, 2003, Benson et al 2004). Therefore, there is increasing evidence for the specific role of IL-23 in immune-mediated disease. Neutralization of IL-23 without inhibition of IL-12 pathways could then provide effective therapy of immune-mediated disease with limited impact on important host defense immune mechanism. This would represent a significant improvement over current therapeutic options.

Currently, there are three classes of biologic agents approved for the treatment of moderately to severely active Crohn's disease: tumor necrosis factor (TNF) antagonist therapies (infliximab, adalimumab, certolizumab), integrin inhibitors (natalizumab and vedolizumab), and an IL-12/23 inhibitor (ustekinumab). Although the introduction of biologic agents has significantly improved the clinical management of patients with moderately to severely active Crohn's disease, a sizable proportion of the target patient population is non-responsive or will lose response over time. A review of the available data for approved biologic agents highlighted the unmet need in achieving and maintaining long-term remission, especially among patients who have previously failed biologic treatments. In all-treated patients (ie, all patients who were randomized at Week 0 of the studies evaluated), the estimated rates of clinical remission at 1 year in the biologic failure or intolerance (BIO-Failure) population is around 20%, and ranges from 20% to 50% in the conventional therapy failure or intolerance (CON-Failure) population.

In summary, there remains considerable unmet medical need for new treatment options, especially therapies with novel mechanisms of action that have the potential to raise the efficacy bar and maximize the proportion of patients who achieve and maintain clinical remission.

SUMMARY OF THE INVENTION

In a first aspect, the invention concerns a method of a subject suffering from Crohn's disease comprising administering an anti-IL-23 specific antibody (also referred to as IL-23p19 antibody), e.g., guselkumab, to the patient in an initial intravenous induction dose from the start of treatment until 8 weeks from the start of treatment, and then subcutaneously administering the anti-IL-23 specific antibody once every 4 or 8 weeks thereafter, e.g., a dose at 0, 4, 8, 12 or 16, 20 or 24, 28 or 32, 36 or 40, 44 or 48 weeks. In addition, in another embodiment the subcutaneous treatment continues through 140 weeks after the start of treatment.

In one embodiment, the subject receives the anti-IL-23 specific antibody at a dose of 1200, 600 or 200 mg intravenously initially, 4 weeks after the initial dose and 8 weeks after the initial dose and continue with subcutaneous treatment of the anti-IL-23 specific antibody at 100 or 200 mg every 4 weeks through 44 weeks after initial treatment.

In another aspect, the composition used in the method of the invention comprises a pharmaceutical composition comprising: an anti-IL-23 specific antibody. In a preferred embodiment, the anti-IL-23 specific antibody is guselkumab in a composition of 7.9% (w/v) sucrose, 4.0 mM Histidine, 6.9 mM L-Histidine monohydrochloride monohydrate; 0.053% (w/v) Polysorbate 80 of the pharmaceutical composition; wherein the diluent is water at standard state.

In an embodiment, Crohn's disease patients achieved significant improvement in clinical endpoints selected from:
  (i) Change from Baseline in the Crohn's Disease Activity Index (CDAI) Score at Week 12 The CDAI score will be assessed by collecting information on 8 different Crohn's disease-related variables, with scores ranging from 0 to approximately 600. A decrease over time indicates improvement in disease activity.
  (ii) Clinical remission at Week 12, defined as CDAI less than (<) 150 points.
  (iii) Clinical response at Week 12, defined as greater than or equal to (>=) 100-point reduction from baseline in CDAI score or CDAI score <150.
  (iv) Patient-Reported Outcome (PRO)-2 Remission at Week 12 defined based on average daily stool frequency (SF) and average daily abdominal pain (AP) score.
  (v) Clinical-Biomarker Response at Week 12 defined using clinical response based on the CDAI score and reduction from baseline in C-reactive protein (CRP) or fecal calprotectin.
  (vi) Endoscopic Response at Week 12 measured by the Simple Endoscopic Score for Crohn's Disease (SES-CD). The SES-CD is based on the evaluation of 4 endoscopic components across 5 ileocolonic segments, with a total score ranging from 0 to 56.
  (vii) Clinical remission at Week 48 defined as CDAI score <150.
  (viii) Durable Clinical Remission at Week 48 defined as CDAI<50 for most of all visits between Week 12 and Week 48.
  (ix) Corticosteroid-Free Clinical Remission at Week 48 defined as CDAI score <150 at Week 48 and not receiving corticosteroids at Week 48.
  (x) PRO-2 remission at Week 48 defined based on average daily stool frequency (SF) and average daily abdominal pain (AP) score. Fatigue response at Week 12 based on the Patient-Reported Outcomes Measurement Information System (PROMIS). Fatigue Short Form 7a contains 7 items that evaluate the severity of fatigue, with higher scores indicating greater fatigue.
  (xi) Endoscopic response at Week 48 measured by the Simple Endoscopic Score for Crohn's Disease (SES-CD).

In another aspect of the invention the pharmaceutical composition comprises an isolated anti-IL23 specific antibody having the guselkumab CDR sequences comprising (i) the heavy chain CDR amino acid sequences of SEQ ID NO: 5, SEQ ID NO: 20, and SEQ ID NO: 44; and (ii) the light chain CDR amino acid sequences of SEQ ID NO: 50, SEQ ID NO: 56, and SEQ ID NO: 73 in a composition of 7.9% (w/v) sucrose, 4.0 mM Histidine, 6.9 mM L-Histidine monohydrochloride monohydrate; 0.053% (w/v) Polysorbate 80 of the pharmaceutical composition; wherein the diluent is water at standard state.

Another aspect of the method of the invention comprises administering a pharmaceutical composition comprising an isolated anti-IL-23 specific antibody having the guselkumab heavy chain variable region amino acid sequence of SEQ ID NO: 106 and the guselkumab light chain variable region amino acid sequence of SEQ ID NO: 116 in a composition of 7.9% (w/v) sucrose, 4.0 mM Histidine, 6.9 mM L-Histidine monohydrochloride monohydrate; 0.053% (w/v) Polysorbate 80 of the pharmaceutical composition; wherein the diluent is water at standard state.

DETAILED DESCRIPTION OF THE PREFERRED EMBODIMENTS

As used herein the method of treatment of a subject suffering from Crohn's disease comprises administering isolated, recombinant and/or synthetic anti-IL-23 specific human antibodies and diagnostic and therapeutic compositions, methods and devices.

As used herein, an "anti-IL-23 specific antibody," "anti-IL-23 antibody," "antibody portion," or "antibody fragment" and/or "antibody variant" and the like include any protein or peptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework region, or any portion thereof, or at least one portion of an IL-23 receptor or binding protein, which can be incorporated into an antibody of the present invention. Such antibody optionally further affects a specific ligand, such as but not limited to, where such antibody modulates, decreases, increases, antagonizes, agonizes, mitigates, alleviates, blocks, inhibits, abrogates and/or interferes with at least one IL-23 activity or binding, or with IL-23 receptor activity or binding, in vitro, in situ and/or in vivo. As a non-limiting example, a suitable anti-IL-23 antibody, specified portion or variant of the present invention can bind at least one IL-23 molecule, or specified portions, variants or domains thereof. A suitable anti-IL-23 antibody, specified portion, or variant can also optionally affect at least one of IL-23 activity or function, such as but not limited to, RNA, DNA or protein synthesis, IL-23 release, IL-23 receptor signaling, membrane IL-23 cleavage, IL-23 activity, IL-23 production and/or synthesis.

The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments that bind to a mammalian IL-23. For example, antibody fragments capable of binding to IL-23 or portions thereof, including, but not limited to, Fab (e.g., by papain digestion), Fab' (e.g., by pepsin digestion and partial reduction) and F(ab')2 (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the $C_H1$ domain and/or hinge region of the heavy chain. The various portions of antibodies can be joined together chemically by conventional techniques, or can be prepared as a contiguous protein using genetic engineering techniques.

As used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially non-immunogenic in humans, with only minor sequence changes or variations. A "human antibody" may also be an antibody that is derived from or closely matches human germline immunoglobulin sequences. Human antibodies may include amino acid residues not encoded by germline immunoglobulin sequences (e.g., mutations introduced by random or site-specific mutagenesis in vitro or by somatic mutation in vivo). Often, this means that the human antibody is substantially non-immunogenic in humans. Human antibodies have been classified into groupings based on their amino acid sequence similarities. Accordingly, using a sequence similarity search, an antibody with a similar linear sequence can be chosen as a template to create a human antibody. Similarly, antibodies designated primate (monkey, baboon, chimpanzee, etc.), rodent (mouse, rat, rabbit, guinea pig, hamster, and the like) and other mammals designate such species, sub-genus, genus, sub-family, and family specific antibodies. Further, chimeric antibodies can include any combination of the above. Such changes or variations optionally and preferably retain or reduce the immunogenicity in humans or other species relative to non-modified antibodies. Thus, a human antibody is distinct from a chimeric or humanized antibody.

It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

Bispecific, heterospecific, heteroconjugate or similar antibodies can also be used that are monoclonal, preferably, human or humanized, antibodies that have binding specificities for at least two different antigens. In the present case, one of the binding specificities is for at least one IL-23 protein, the other one is for any other antigen. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, *Nature* 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed, e.g., in WO 93/08829, U.S. Pat. Nos. 6,210,668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, 4,676,980, WO 91/00360, WO 92/00373, EP 03089, Traunecker et al., *EMBO J.* 10:3655 (1991), Suresh et al., *Methods in Enzymology* 121:210 (1986), each entirely incorporated herein by reference.

Anti-IL-23 specific (also termed IL-23 specific antibodies) (or antibodies to IL-23) useful in the methods and compositions of the present invention can optionally be characterized by high affinity binding to IL-23 and, optionally and preferably, having low toxicity. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titres in the patient treated (less than about 300, preferably less than about 100 measured with a double antigen enzyme immunoassay) (Elliott et al., *Lancet* 344: 1125-1127 (1994), entirely incorporated herein by reference). "Low immunogenicity" can also be defined as the incidence of titrable levels of antibodies to the anti-IL-23 antibody in patients treated with anti-IL-23 antibody as occurring in less than 25% of patients treated, preferably, in less than 10% of patients treated with the recommended dose for the recommended course of therapy during the treatment period.

The term "safe," as it relates to a dose, dosage regimen, treatment or method with an anti-IL-23 antibody of the present invention (e.g., the anti-IL-23 antibody guselkumab), refers to a relatively low or reduced frequency and/or low or reduced severity of treatment-emergent adverse events (referred to as AEs or TEAEs) from the clinical trials conducted, e.g., Phase 2 clinical trials and earlier, compared to the standard of care or to another comparator. An adverse event is an untoward medical occurrence in a patient administered a medicinal product. In particular, safe as it relates to a dose, dosage regimen or treatment with an anti-IL-23 antibody of the present invention refers to a relatively low or reduced frequency and/or low or reduced severity of adverse events associated with administration of the antibody if attribution is considered to be possible, probable, or very likely due to the use of the anti-IL-23 antibody.

Utility

The isolated nucleic acids of the present invention can be used for production of at least one anti-IL-23 antibody or specified variant thereof, which can be used to measure or effect in a cell, tissue, organ or animal (including mammals and humans), to diagnose, monitor, modulate, treat, alleviate, help prevent the incidence of, or reduce the symptoms of Crohn's disease.

Such a method can comprise administering an effective amount of a composition or a pharmaceutical composition comprising at least one anti-IL-23 antibody to a cell, tissue, organ, animal or patient in need of such modulation, treatment, alleviation, prevention, or reduction in symptoms, effects or mechanisms. The effective amount can comprise an amount of about 0.001 to 500 mg/kg per single (e.g., bolus), multiple or continuous administration, or to achieve a serum concentration of 0.01-5000 μg/ml serum concentration per single, multiple, or continuous administration, or any effective range or value therein, as done and determined using known methods, as described herein or known in the relevant arts.

Citations

All publications or patents cited herein, whether or not specifically designated, are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., *Current Protocols in Molecular Biology*, John Wiley & Sons, Inc., NY, NY (1987-2001); Sambrook, et al., *Molecular Cloning: A Laboratory Manual*, $2^{nd}$ Edition, Cold Spring Harbor, NY (1989); *Harlow and Lane, antibodies, a Laboratory Manual*, Cold Spring Harbor, NY (1989); Colligan, et al., eds., *Current Protocols in Immunology*, John Wiley & Sons, Inc., NY (1994-2001); Colligan et al., *Current Protocols in Protein Science*, John Wiley & Sons, NY, NY, (1997-2001).

Antibodies of the Present Invention—Production and Generation

At least one anti-IL-23 antibody used in the method of the present invention can be optionally produced by a cell line, a mixed cell line, an immortalized cell or clonal population of immortalized cells, as well known in the art. See, e.g., Ausubel, et al., ed., *Current Protocols in Molecular Biology*, John Wiley & Sons, Inc., NY, NY (1987-2001); Sambrook, et al., *Molecular Cloning: A Laboratory Manual*, $2^{nd}$ Edition, Cold Spring Harbor, NY (1989); *Harlow and Lane, antibodies, a Laboratory Manual*, Cold Spring Harbor, NY (1989); Colligan, et al., eds., *Current Protocols in Immunology*, John Wiley & Sons, Inc., NY (1994-2001); Colligan et al., *Current Protocols in Protein Science*, John Wiley & Sons, NY, NY, (1997-2001), each entirely incorporated herein by reference.

A preferred anti-IL-23 antibody is guselkumab (also referred to as CNTO1959) having the heavy chain variable region amino acid sequence of SEQ ID NO: 106 and the light chain variable region amino acid sequence of SEQ ID NO: 116 and having the heavy chain CDR amino acid sequences of SEQ ID NO: 5, SEQ ID NO: 20, and SEQ ID NO: 44; and the light chain CDR amino acid sequences of SEQ ID NO: 50, SEQ ID NO: 56, and SEQ ID NO: 73. Other anti-IL-23 antibodies have sequences listed herein and are described in U.S. Pat. No. 7,935,344, the entire contents of which are incorporated herein by reference).

Human antibodies that are specific for human IL-23 proteins or fragments thereof can be raised against an appropriate immunogenic antigen, such as an isolated IL-23 protein and/or a portion thereof (including synthetic molecules, such as synthetic peptides). Other specific or general mammalian antibodies can be similarly raised. Preparation of immunogenic antigens, and monoclonal antibody production can be performed using any suitable technique.

In one approach, a hybridoma is produced by fusing a suitable immortal cell line (e.g., a myeloma cell line, such as, but not limited to, Sp2/0, Sp2/0-AG14, NSO, NS1, NS2, AE-1, L.5, L243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMALWA, NEURO 2A, or the like, or heteromylomas, fusion products thereof, or any cell or fusion cell derived therefrom, or any other suitable cell line as known in the art) (see, e.g., www.atcc.org, www.lifetech.com., and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

Antibody producing cells can also be obtained from the peripheral blood or, preferably, the spleen or lymph nodes, of humans or other suitable animals that have been immunized with the antigen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from Cambridge antibody Technologies, Cambridgeshire, UK; MorphoSys, Martinsreid/Planegg, DE; Biovation, Aberdeen, Scotland, UK; BioInvent, Lund, Sweden; Dyax Corp., Enzon, Affymax/Biosite; Xoma, Berkeley, CA; Ixsys. See, e.g., EP 368,684, PCT/GB91/01134; PCT/GB92/01755; PCT/GB92/002240; PCT/GB92/00883; PCT/GB93/00605; U.S. Ser. No. 08/350,260(5/12/94); PCT/GB94/01422; PCT/GB94/02662; PCT/GB97/01835; (CAT/MRC); WO90/14443; WO90/14424; WO90/14430; PCT/US94/1234; WO92/18619; WO96/07754; (Scripps); WO96/13583, WO97/08320 (MorphoSys); WO95/16027 (BioInvent); WO88/06630; WO90/3809 (Dyax); U.S. Pat. No. 4,704,692 (Enzon); PCT/US91/02989 (Affymax); WO89/06283; EP 371 998; EP 550 400; (Xoma); EP 229 046; PCT/US91/07149 (Ixsys); or stochastically generated peptides or proteins—U.S. Pat. Nos. 5,723,323, 5,763,192, 5,814,476, 5,817,483, 5,824,514, 5,976,862, WO 86/05803, EP 590 689 (Ixsys, predecessor of Applied Molecular Evolution (AME), each entirely incorporated herein by reference)) or that rely upon immunization of transgenic animals (e.g., SCID mice, Nguyen et al., *Microbiol. Immunol.* 41:901-907 (1997); Sandhu et al., Crit. Rev. *Biotechnol.* 16:95-118 (1996); Eren et al., *Immunol.* 93:154-161 (1998), each entirely incorporated by reference as well as related patents and applications) that are capable of producing a repertoire of human antibodies, as known in the art and/or as described herein.

Such techniques, include, but are not limited to, ribosome display (Hanes et al., *Proc. Natl. Acad. Sci.* USA, 94:4937-4942 (May 1997); Hanes et al., *Proc. Natl. Acad. Sci. USA*, 95:14130-14135 (November 1998)); single cell antibody producing technologies (e.g., selected lymphocyte antibody method ("SLAM") (U.S. Pat. No. 5,627,052, Wen et al., J. Immunol. 17:887-892 (1987); Babcook et al., *Proc. Natl. Acad. Sci. USA* 93:7843-7848 (1996)); gel microdroplet and flow cytometry (Powell et al., *Biotechnol.* 8:333-337 (1990); One Cell Systems, Cambridge, MA; Gray et al., *J. Imm. Meth.* 182:155-163 (1995); Kenny et al., *Bio/Technol.* 13:787-790 (1995)); B-cell selection (Steenbakkers et al., *Molec. Biol. Reports* 19:125-134 (1994); Jonak et al., *Progress Biotech*, Vol. 5, In Vitro Immunization in Hybridoma Technology, Borrebaeck, ed., Elsevier Science Publishers B.V., Amsterdam, Netherlands (1988)).

Methods for engineering or humanizing non-human or human antibodies can also be used and are well known in the art. Generally, a humanized or engineered antibody has one or more amino acid residues from a source that is non-human, e.g., but not limited to, mouse, rat, rabbit, non-human primate or other mammal. These non-human amino acid residues are replaced by residues often referred to as "import" residues, which are typically taken from an "import" variable, constant or other domain of a known human sequence.

Known human Ig sequences are disclosed, e.g., www.ncbi.nlm.nih.gov/entrez/query.fcgi; www.ncbi.nih.gov/ig-blast; www.atcc.org/phage/hdb.html; www.mrc-cpe.cam.ac.uk/ALIGNMENTS.php; www.kabatdatabase.com/top.html; ftp.ncbi.nih.gov/repository/kabat; www.sciquest.com; www.abcam.com; www.antibodyresource.com/onlinecomp.html; www.public.iastate.edu/-pedro/research_tools.html; www.whfreeman.com/immunology/CH05/kuby05.htm; www.hhmi.org/grants/lectures/1996/vlab; www.path.cam.ac.uk/-mrc7/mikeimages.html; mcb.harvard.edu/BioLinks/Immunology.html; www.immunologylink.com; pathbox.wustl.edu/-hcenter/index.html; www.appliedbiosystems.com; www.nal.usda.gov/awic/pubs/antibody; www.m.ehime-u.ac.jp/-yasuhito/Elisa.html; www.biodesign.com; www.cancerresearchuk.org; www.biotech.ufl.edu; www.isac-net.org; baserv.uci.kun.nl/-jraats/links1.html; www.recab.uni-hd.de/immuno.bme.nwu.edu; www.mrc-cpe.cam.ac.uk; www.ibt.unam.mx/vir/V_mice.html; www.bioinf.org.uk/abs; antibody.bath.ac.uk; www.unizh.ch; www.cryst.bbk.ac.uk/-ubcg07s; www.nimr.mrc.ac.uk/CC/ccaewg/ccaewg.html; www.path.cam.ac.uk/~mrc7/humanisation/TAHHP.html; www.ibt.unam.mx/vir/structure/stat_aim.html; www.biosci.missouri.edu/smithgp/index.html; www.jerini.de; Kabat et al., Sequences of Proteins of Immunological Interest, *U.S. Dept. Health* (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing antigen binding. Accordingly, part or all of the non-human or human CDR sequences are maintained while the non-human sequences of the variable and constant regions may be replaced with human or other amino acids.

Antibodies can also optionally be humanized or human antibodies engineered with retention of high affinity for the antigen and other favorable biological properties. To achieve this goal, humanized (or human) antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, framework (FR) residues can be selected and combined from the consensus and import sequences so that the desired antibody characteristic, such as increased affinity for the target antigen(s), is achieved.

In addition, the human IL-23 specific antibody used in the method of the present invention may comprise a human germline light chain framework. In particular embodiments, the light chain germline sequence is selected from human VK sequences including, but not limited to, A1, A10, A11, A14, A17, A18, A19, A2, A20, A23, A26, A27, A3, A30, A5, A7, B2, B3, L1, L10, L11, L12, L14, L15, L16, L18, L19, L2, L20, L22, L23, L24, L25, L4/18a, L5, L6, L8, L9, O1, O11, O12, O14, O18, O2, O4, and O8. In certain embodiments, this light chain human germline framework is selected from V1-11, V1-13, V1-16, V1-17, V1-18, V1-19, V1-2, V1-20, V1-22, V1-3, V1-4, V1-5, V1-7, V1-9, V2-1, V2-11, V2-13, V2-14, V2-15, V2-17, V2-19, V2-6, V2-7, V2-8, V3-2, V3-3, V3-4, V4-1, V4-2, V4-3, V4-4, V4-6, V5-1, V5-2, V5-4, and V5-6.

In other embodiments, the human IL-23 specific antibody used in the method of the present invention may comprise a human germline heavy chain framework. In particular embodiments, this heavy chain human germline framework is selected from $V_H1-18$, $V_H1-2$, $V_H1-24$, $V_H1-3$, $V_H1-45$, $V_H1-46$, $V_H1-58$, $V_H1-69$, $V_H1-8$, $V_H2-26$, $V_H2-5$, $V_H2-70$, $V_H3-11$, $V_H3-13$, $V_H3-15$, $V_H3-16$, $V_H3-20$, $V_H3-21$, $V_H3-23$, $V_H3-30$, $V_H3-33$, $V_H3-35$, $V_H3-38$, $V_H3-43$, $V_H3-48$, $V_H3-49$, $V_H3-53$, $V_H3-64$, $V_H3-66$, $V_H3-7$, $V_H3-72$, $V_H3-73$, $V_H3-74$, $V_H3-9$, V14-28, $V_H4-31$, $V_H4-34$, $V_H4-39$, V14-4, $V_H4-59$, $V_H4-61$, $V_H5-51$, $V_H6-1$, and $V_H7-81$.

In particular embodiments, the light chain variable region and/or heavy chain variable region comprises a framework region or at least a portion of a framework region (e.g., containing 2 or 3 subregions, such as FR2 and FR3). In certain embodiments, at least FRL1, FRL2, FRL3, or FRL4 is fully human. In other embodiments, at least FRH1, FRH2, FRH3, or FRH4 is fully human. In some embodiments, at least FRL1, FRL2, FRL3, or FRL4 is a germline sequence (e.g., human germline) or comprises human consensus sequences for the particular framework (readily available at the sources of known human Ig sequences described above). In other embodiments, at least FRH1, FRH2, FRH3, or FRH4 is a germline sequence (e.g., human germline) or comprises human consensus sequences for the particular framework. In preferred embodiments, the framework region is a fully human framework region.

Humanization or engineering of antibodies of the present invention can be performed using any known method, such as but not limited to those described in, Winter (Jones et al., *Nature* 321:522 (1986); Riechmann et al., *Nature* 332:323 (1988); Verhoeyen et al., *Science* 239:1534 (1988)), Sims et al., *J. Immunol.* 151: 2296 (1993); *Chothia and Lesk, J. Mol. Biol.* 196:901 (1987); Carter et al., *Proc. Natl. Acad. Sci. U.S.A.* 89:4285 (1992); Presta et al., *J. Immunol.* 151:2623 (1993), U.S. Pat. Nos. 5,723,323, 5,976,862, 5,824,514, 5,817,483, 5,814,476, 5,763,192, 5,723,323, 5,766886, 5714352, 6204023, 6180370, 5693762, 5530101, 5585089, 5225539; 4816567, PCT/: US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, included references cited therein.

In certain embodiments, the antibody comprises an altered (e.g., mutated) Fc region. For example, in some embodiments, the Fc region has been altered to reduce or enhance the effector functions of the antibody. In some embodiments, the Fc region is an isotype selected from IgM, IgA, IgG, IgE, or other isotype. Alternatively or additionally, it may be useful to combine amino acid modifications with one or more further amino acid modifications that alter C1q binding and/or the complement dependent cytotoxicity function of the Fc region of an IL-23 binding molecule. The starting polypeptide of particular interest may be one that binds to C1q and displays complement dependent cytotoxicity (CDC). Polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO0042072, which is hereby incorporated by reference.

As disclosed above, one can design an Fc region of the human IL-23 specific antibody of the present invention with altered effector function, e.g., by modifying C1q binding and/or FcγR binding and thereby changing complement dependent cytotoxicity (CDC) activity and/or antibody-dependent cell-mediated cytotoxicity (ADCC) activity. "Effector functions" are responsible for activating or diminishing a biological activity (e.g., in a subject). Examples of effector functions include, but are not limited to: C1q binding; CDC; Fc receptor binding; ADCC; phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of the human IL-23 (or anti-IL-23) antibody with improved C1q binding and improved FcγRIIIbinding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

Fc mutations can also be introduced in engineer to alter their interaction with the neonatal Fc receptor (FcRn) and improve their pharmacokinetic properties. A collection of human Fc variants with improved binding to the FcRn have been described (Shields et al., (2001). High resolution mapping of the binding site on human IgG1 for FcγRI, FcγRII, FcγRIII, and FcRn and design of IgG1 variants with improved binding to the FcγR, *J. Biol. Chem.* 276:6591-6604).

Another type of amino acid substitution serves to alter the glycosylation pattern of the Fc region of the human IL-23 specific antibody. Glycosylation of an Fc region is typically either N-linked or O-linked. N-linked refers to the attachment of the carbohydrate moiety to the side chain of an asparagine residue. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation sites that are not present in the polypeptide. Addition of glycosylation sites to the Fc region of a human IL-23 specific antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the human IL-23 specific antibody of the present invention is expressed in cells that express beta (1,4)-N-acetylglucosaminyltransferase III (GnT III), such that GnT III adds GlcNAc to the human IL-23 antibody. Methods for producing antibodies in such a fashion are provided in WO/9954342, WO/03011878, patent publication 20030003097A1, and Umana et al., *Nature Biotechnology,* 17:176-180, February 1999; all of which are herein specifically incorporated by reference in their entireties.

The anti-IL-23 antibody can also be optionally generated by immunization of a transgenic animal (e.g., mouse, rat, hamster, non-human primate, and the like) capable of producing a repertoire of human antibodies, as described herein and/or as known in the art. Cells that produce a human anti-IL-23 antibody can be isolated from such animals and immortalized using suitable methods, such as the methods described herein.

Transgenic mice that can produce a repertoire of human antibodies that bind to human antigens can be produced by known methods (e.g., but not limited to, U.S. Pat. Nos. 5,770,428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. *Nature* 368:856-859 (1994), Taylor et al., *Int. Immunol.* 6(4)579-591 (1994), Green et al, *Nature Genetics* 7:13-21 (1994), Mendez et al., *Nature Genetics* 15:146-156 (1997), Taylor et al., *Nucleic Acids Research* 20(23):6287-6295 (1992), Tuaillon et al., *Proc Natl Acad Sci USA* 90(8)3720-3724 (1993), Lonberg et al., *Int Rev Immunol* 13(1):65-93 (1995) and Fishwald et al., *Nat Biotechnol* 14(7):845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

Screening antibodies for specific binding to similar proteins or fragments can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278.

Other systems for generating libraries of peptides have aspects of both in vitro chemical synthesis and recombinant methods. See, PCT Patent Publication Nos. 92/05258, 92/14843, and 96/19256. See also, U.S. Pat. Nos. 5,658,754; and 5,643,768. Peptide display libraries, vector, and screening kits are commercially available from such suppliers as Invitrogen (Carlsbad, CA), and Cambridge antibody Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456, assigned to Enzon; U.S. Pat. Nos. 5,223,409, 5,403,484, 5,571,698, 5,837,500, assigned to Dyax, 5427908, 5580717, assigned to Affymax; 5885793, assigned to Cambridge antibody Technologies; 5750373, assigned to Genentech, 5618920, 5595898, 5576195, 5698435, 5693493, 5698417, assigned to Xoma, Colligan, supra; Ausubel, supra; or Sambrook, supra, each of the above patents and publications entirely incorporated herein by reference.

Antibodies used in the method of the present invention can also be prepared using at least one anti-IL23 antibody encoding nucleic acid to provide transgenic animals or mammals, such as goats, cows, horses, sheep, rabbits, and the like, that produce such antibodies in their milk. Such animals can be provided using known methods. See, e.g., but not limited to, U.S. Pat. Nos. 5,827,690; 5,849,992; 4,873, 316; 5,849,992; 5,994,616; 5,565,362; 5,304,489, and the like, each of which is entirely incorporated herein by reference.

Antibodies used in the method of the present invention can additionally be prepared using at least one anti-IL23 antibody encoding nucleic acid to provide transgenic plants and cultured plant cells (e.g., but not limited to, tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., *Curr. Top. Microbol. Immunol.* 240:95-118 (1999) and references cited therein. Also, transgenic maize have been used to express mammalian proteins at commercial production levels, with biological activities equivalent to those produced in other recombinant systems or purified from natural sources. See, e.g., Hood et al., *Adv. Exp. Med. Biol.* 464:127-147 (1999) and references cited therein. Antibodies have also been produced in large amounts from transgenic plant seeds including antibody fragments, such as single chain antibodies (scFv's), including tobacco seeds and potato tubers. See, e.g., Conrad et al., *Plant Mol. Biol.* 38:101-109 (1998) and references cited therein. Thus, antibodies of the present invention can also be produced using transgenic plants, according to known methods. See also, e.g., Fischer et al., *Biotechnol. Appl. Biochem.* 30:99-108 (October, 1999), Ma et al., *Trends Biotechnol.* 13:522-7 (1995); Ma et al., *Plant Physiol.* 109:341-6 (1995); Whitelam et al., *Biochem. Soc. Trans.* 22:940-944 (1994); and references cited therein. Each of the above references is entirely incorporated herein by reference.

The antibodies used in the method of the invention can bind human IL-23 with a wide range of affinities ($K_D$). In a preferred embodiment, a human mAb can optionally bind human IL-23 with high affinity. For example, a human mAb can bind human IL-23 with a $K_D$ equal to or less than about $10^{-7}$ M, such as but not limited to, 0.1-9.9 (or any range or value therein)$\times 10^{-7}$, $10^{-8}$, $10^{-9}$, $10^{-10}$, $10^{-11}$, $10^{-12}$, $10^{-13}$ or any range or value therein.

The affinity or avidity of an antibody for an antigen can be determined experimentally using any suitable method. (See, for example, Berzofsky, et al., "Antibody-Antigen Interactions," In *Fundamental Immunology*, Paul, W. E., Ed., Raven Press: New York, NY (1984); Kuby, *Janis Immunology*, W. H. Freeman and Company: New York, NY (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer, such as the buffer described herein.

Nucleic Acid Molecules

Using the information provided herein, for example, the nucleotide sequences encoding at least 70-100% of the contiguous amino acids of at least one of the light or heavy chain variable or CDR regions described herein, among other sequences disclosed herein, specified fragments, variants or consensus sequences thereof, or a deposited vector comprising at least one of these sequences, a nucleic acid molecule of the present invention encoding at least one anti-IL-23 antibody can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules used in the method of the present invention can include nucleic acid molecules comprising an open reading frame (ORF), optionally, with one or more introns, e.g., but not limited to, at least one specified portion of at least one CDR, such as CDR1, CDR2 and/or CDR3 of at least one heavy chain or light chain; nucleic acid molecules comprising the coding sequence for an anti-IL-23 antibody or variable region; and nucleic acid molecules which comprise a nucleotide sequence substantially different from those described above but which, due to the degeneracy of the genetic code, still encode at least one anti-IL-23 antibody as described herein and/or as known in the art. Of course, the genetic code is well known in the art. Thus, it would be routine for one skilled in the art to generate such degenerate nucleic acid variants that code for specific anti-IL-23 antibodies used in the method of the present invention. See, e.g., Ausubel, et al., supra, and such nucleic acid variants are included in the present invention. Non-limiting examples of isolated nucleic acid molecules include nucleic acids encoding HC CDR1, HC CDR2, HC CDR3, LC CDR1, LC CDR2, and LC CDR3, respectively.

As indicated herein, nucleic acid molecules which comprise a nucleic acid encoding an anti-IL-23 antibody can include, but are not limited to, those encoding the amino acid sequence of an antibody fragment, by itself, the coding sequence for the entire antibody or a portion thereof; the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example, ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

Polynucleotides Selectively Hybridizing to a Polynucleotide as Described Herein

The method of the present invention uses isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably, at least 85% or 90% full-length sequences, and, more preferably, at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides will encode at least a portion of an antibody. The polynucleotides embrace nucleic acid sequences that can be employed for selective hybridization to a polynucleotide encoding an antibody of the present invention. See, e.g., Ausubel, supra; Colligan, supra, each entirely incorporated herein by reference.

Construction of Nucleic Acids

The isolated nucleic acids can be made using (a) recombinant methods, (b) synthetic techniques, (c) purification techniques, and/or (d) combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention, excluding the coding sequence, is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra)

Recombinant Methods for Constructing Nucleic Acids

The isolated nucleic acid compositions, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, are well known to those of ordinary skill in the art. (See, e.g., Ausubel, supra; or Sambrook, supra)

Nucleic Acid Screening and Isolation Methods

A cDNA or genomic library can be screened using a probe based upon the sequence of a polynucleotide used in the method of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent, such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides used in the method of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., *PCR Protocols A Guide to Methods and Applications, Eds.*, Academic Press Inc., San Diego, CA (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids

The isolated nucleic acids used in the method of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The present invention uses recombinant expression cassettes comprising a nucleic acid. A nucleic acid sequence, for example, a cDNA or a genomic sequence encoding an antibody used in the method of the present invention, can be used to construct a recombinant expression cassette that can be introduced into at least one desired host cell. A recombinant expression cassette will typically comprise a polynucleotide operably linked to transcriptional initiation regulatory sequences that will direct the transcription of the polynucleotide in the intended host cell. Both heterologous and non-heterologous (i.e., endogenous) promoters can be employed to direct expression of the nucleic acids.

In some embodiments, isolated nucleic acids that serve as promoter, enhancer, or other elements can be introduced in the appropriate position (upstream, downstream or in the intron) of a non-heterologous form of a polynucleotide of the present invention so as to up or down regulate expression of a polynucleotide. For example, endogenous promoters can be altered in vivo or in vitro by mutation, deletion and/or substitution.

Vectors and Host Cells

The present invention also relates to vectors that include isolated nucleic acid molecules, host cells that are genetically engineered with the recombinant vectors, and the production of at least one anti-IL-23 antibody by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but are not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827,739) resistance for eukaryotic cell culture, and tetracycline or ampicillin resistance genes for culturing in *E. coli* and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

At least one antibody used in the method of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein used in the method of the present invention. Alternatively, nucleic acids can be expressed in a host cell by turning on (by manipulation) in a host cell that contains endogenous DNA encoding an antibody. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va (www.atcc.org). Preferred host cells include cells of lymphoid origin, such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or a SP2/0-Ag14 cell.

Expression vectors for these cells can include one or more of the following expression control sequences, such as, but not limited to, an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., *J. Virol.* 45:773-781 (1983)). Additionally, gene sequences to control replication in the host cell can be incorporated into the vector, as known in the art.

Purification of an Antibody

An anti-IL-23 antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, *Current Protocols in Immunology*, or *Current Protocols in Protein Science*, John Wiley & Sons, NY, NY, (1997-2001), e.g., Chapters 1, 4, 6, 8, 9, 10, each entirely incorporated herein by reference.

Antibodies used in the method of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Anti-IL-23 Antibodies

An anti-IL-23 antibody according to the present invention includes any protein or peptide containing molecule that comprises at least a portion of an immunoglobulin molecule, such as but not limited to, at least one ligand binding portion (LBP), such as but not limited to, a complementarity determining region (CDR) of a heavy or light chain or a ligand binding portion thereof, a heavy chain or light chain variable region, a framework region (e.g., FR1, FR2, FR3, FR4 or fragment thereof, further optionally comprising at least one substitution, insertion or deletion), a heavy chain or light chain constant region, (e.g., comprising at least one $C_H1$, hinge1, hinge2, hinge3, hinge4, $C_H2$, or $C_H3$ or fragment thereof, further optionally comprising at least one substitution, insertion or deletion), or any portion thereof, that can be incorporated into an antibody. An antibody can include or be derived from any mammal, such as but not limited to, a human, a mouse, a rabbit, a rat, a rodent, a primate, or any combination thereof, and the like.

The isolated antibodies used in the method of the present invention comprise the antibody amino acid sequences disclosed herein encoded by any suitable polynucleotide, or any isolated or prepared antibody. Preferably, the human antibody or antigen-binding fragment binds human IL-23 and, thereby, partially or substantially neutralizes at least one biological activity of the protein. An antibody, or specified portion or variant thereof, that partially or preferably substantially neutralizes at least one biological activity of at least one IL-23 protein or fragment can bind the protein or fragment and thereby inhibit activities mediated through the binding of IL-23 to the IL-23 receptor or through other IL-23-dependent or mediated mechanisms. As used herein, the term "neutralizing antibody" refers to an antibody that can inhibit an IL-23-dependent activity by about 20-120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an anti-IL-23 antibody to inhibit an IL-23-dependent activity is preferably assessed by at least one suitable IL-23 protein or receptor assay, as described herein and/or as known in the art. A human antibody can be of any class (IgG, IgA, IgM, IgE, IgD, etc.) or isotype and can comprise a kappa or lambda light chain. In one embodiment, the human antibody comprises an IgG heavy chain or defined fragment, for example, at least one of isotypes, IgG1, IgG2, IgG3 or IgG4 (e.g., γ1, γ2, γ3, γ4). Antibodies of this type can be prepared by employing a transgenic mouse or other trangenic non-human mammal comprising at least one human light chain (e.g., IgG, IgA, and IgM) transgenes as described herein and/or as known in the art. In another embodiment, the anti-IL-23 human antibody comprises an IgG1 heavy chain and an IgG1 light chain.

An antibody binds at least one specified epitope specific to at least one IL-23 protein, subunit, fragment, portion or any combination thereof. The at least one epitope can comprise at least one antibody binding region that comprises at least one portion of the protein, which epitope is preferably comprised of at least one extracellular, soluble, hydrophillic, external or cytoplasmic portion of the protein.

Generally, the human antibody or antigen-binding fragment will comprise an antigen-binding region that comprises at least one human complementarity determining region (CDR1, CDR2 and CDR3) or variant of at least one heavy chain variable region and at least one human complementarity determining region (CDR1, CDR2 and CDR3) or variant of at least one light chain variable region. The CDR sequences may be derived from human germline sequences or closely match the germline sequences. For example, the CDRs from a synthetic library derived from the original non-human CDRs can be used. These CDRs may be formed by incorporation of conservative substitutions from the original non-human sequence. In another particular embodiment, the antibody or antigen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3.

Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method.

The anti-IL-23 specific antibody can comprise at least one of a heavy or light chain variable region having a defined amino acid sequence. For example, in a preferred embodiment, the anti-IL-23 antibody comprises at least one of at least one heavy chain variable region, optionally having the amino acid sequence of SEQ ID NO:106 and/or at least one light chain variable region, optionally having the amino acid sequence of SEQ ID NO:116. Antibodies that bind to human IL-23 and that comprise a defined heavy or light chain variable region can be prepared using suitable methods, such as phage display (Katsube, Y., et al., *Int J Mol. Med,* 1(5):863-868 (1998)) or methods that employ transgenic animals, as known in the art and/or as described herein. For example, a transgenic mouse, comprising a functionally rearranged human immunoglobulin heavy chain transgene and a transgene comprising DNA from a human immunoglobulin light chain locus that can undergo functional rearrangement, can be immunized with human IL-23 or a fragment thereof to elicit the production of antibodies. If desired, the antibody producing cells can be isolated and hybridomas or other immortalized antibody-producing cells can be prepared as described herein and/or as known in the art. Alternatively, the antibody, specified portion or variant can be expressed using the encoding nucleic acid or portion thereof in a suitable host cell.

The invention also relates to antibodies, antigen-binding fragments, immunoglobulin chains and CDRs comprising amino acids in a sequence that is substantially the same as an amino acid sequence described herein. Preferably, such antibodies or antigen-binding fragments and antibodies comprising such chains or CDRs can bind human IL-23 with high affinity (e.g., $K_D$ less than or equal to about $10^{-9}$ M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include, without limitation, replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Amino Acid Codes

The amino acids that make up anti-IL-23 antibodies of the present invention are often abbreviated. The amino acid designations can be indicated by designating the amino acid by its single letter code, its three letter code, name, or three nucleotide codon(s) as is well understood in the art (see Alberts, B., et al., *Molecular Biology of The Cell*, Third Ed., Garland Publishing, Inc., New York, 1994):

| SINGLE LETTER CODE | THREE LETTER CODE | NAME | THREE NUCLEOTIDE CODON(S) |
|---|---|---|---|
| A | Ala | Alanine | GCA, GCC, GCG, GCU |
| C | Cys | Cysteine | UGC, UGU |
| D | Asp | Aspartic acid | GAC, GAU |
| E | Glu | Glutamic acid | GAA, GAG |
| F | Phe | Phenylanine | UUC, UUU |
| G | Gly | Glycine | GGA, GGC, GGG, GGU |
| H | His | Histidine | CAC, CAU |
| I | Ile | Isoleucine | AUA, AUC, AUU |
| K | Lys | Lysine | AAA, AAG |
| L | Leu | Leucine | UUA, UUG, CUA, CUC, CUG, CUU |
| M | Met | Methionine | AUG |
| N | Asn | Asparagine | AAC, AAU |
| P | Pro | Proline | CCA, CCC, CCG, CCU |
| Q | Gln | Glutamine | CAA, CAG |
| R | Arg | Arginine | AGA, AGG, CGA, CGC, CGG, CGU |
| S | Ser | Serine | AGC, AGU, UCA, UCC, UCG, UCU |
| T | Thr | Threonine | ACA, ACC, ACG, ACU |
| V | Val | Valine | GUA, GUC, GUG, GUU |
| W | Trp | Tryptophan | UGG |
| Y | Tyr | Tyrosine | UAC, UAU |

An anti-IL-23 antibody used in the method of the present invention can include one or more amino acid substitutions, deletions or additions, either from natural mutations or human manipulation, as specified herein.

The number of amino acid substitutions a skilled artisan would make depends on many factors, including those described above. Generally speaking, the number of amino acid substitutions, insertions or deletions for any given anti-IL-23 antibody, fragment or variant will not be more than 40, 30, 20, 19, 18, 17, 16, 15, 14, 13, 12, 11, 10, 9, 8, 7, 6, 5, 4, 3, 2, 1, such as 1-30 or any range or value therein, as specified herein.

Amino acids in an anti-IL-23 specific antibody that are essential for function can be identified by methods known in the art, such as site-directed mutagenesis or alanine-scanning mutagenesis (e.g., Ausubel, supra, Chapters 8, 15; Cunningham and Wells, *Science* 244:1081-1085 (1989)). The latter procedure introduces single alanine mutations at every residue in the molecule. The resulting mutant molecules are then tested for biological activity, such as, but not limited to, at least one IL-23 neutralizing activity. Sites that are critical for antibody binding can also be identified by structural analysis, such as crystallization, nuclear magnetic resonance or photoaffinity labeling (Smith, et al., *J. Mol. Biol.* 224:899-904 (1992) and de Vos, et al., *Science* 255: 306-312 (1992)).

Anti-IL-23 antibodies can include, but are not limited to, at least one portion, sequence or combination selected from 5 to all of the contiguous amino acids of at least one of SEQ ID NOS: 5, 20, 44, 50, 56, and 73.

IL-23 antibodies or specified portions or variants can include, but are not limited to, at least one portion, sequence or combination selected from at least 3-5 contiguous amino acids of the SEQ ID NOs above; 5-17 contiguous amino acids of the SEQ ID NOs above, 5-10 contiguous amino acids of the SEQ ID NOs above, 5-11 contiguous amino acids of the SEQ ID NOs above, 5-7 contiguous amino acids of the SEQ ID NOs above; 5-9 contiguous amino acids of the SEQ ID NOs above.

An anti-IL-23 antibody can further optionally comprise a polypeptide of at least one of 70-100% of 5, 17, 10, 11, 7, 9, 119, or 108 contiguous amino acids of the SEQ ID NOs above. In one embodiment, the amino acid sequence of an immunoglobulin chain, or portion thereof (e.g., variable region, CDR) has about 70-100% identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or any range or value therein) to the amino acid sequence of the corresponding chain of at least one of the SEQ ID NOs above. For example, the amino acid sequence of a light chain variable region can be compared with the sequence of the SEQ ID NOs above, or the amino acid sequence of a heavy chain CDR3 can be compared with the SEQ ID NOs above. Preferably, 70-100% amino acid identity (i.e., 90, 91, 92, 93, 94, 95, 96, 97, 98, 99, 100 or any range or value therein) is determined using a suitable computer algorithm, as known in the art.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" and "similarity" can be readily calculated by known methods, including, but not limited to, those described in *Computational Molecular Biology*, Lesk, A. M., ed., Oxford University Press, New York, 1988; Biocomputing:Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; *Sequence Analysis in Molecular Biology*, von Heinje, G., Academic Press, 1987; and Sequence Analysis Primer, Gribskov, M. and Devereux, J., eds., M Stockton Press, New York, 1991; and Carillo, H., and Lipman, D., Siam *J. Applied Math.*, 48:1073 (1988). In addition, values for percentage identity can be obtained from amino acid and nucleotide sequence alignments generated using the default settings for the AlignX component of Vector NTI Suite 8.0 (Informax, Frederick, MD).

Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Atschul, S. F. et al., *J. Molec. Biol.* 215:403-410 (1990)). The BLAST X program is publicly available from NCBI and other sources (*BLAST Manual*, Altschul, S., et al., *NCBI NLM NIH Bethesda, Md.* 20894: Altschul, S., et al., *J. Mol. Biol.* 215:403-410 (1990). The well-known Smith Waterman algorithm may also be used to determine identity.

Preferred parameters for polypeptide sequence comparison include the following: (1) Algorithm: Needleman and Wunsch, *J. Mol Biol.* 48:443-453 (1970) Comparison matrix: BLOSSUM62 from Hentikoff and Hentikoff, *Proc. Natl. Acad. Sci, USA.* 89:10915-10919 (1992)

Gap Penalty: 12

Gap Length Penalty: 4

A program useful with these parameters is publicly available as the "gap" program from Genetics Computer Group, Madison Wis. The aforementioned parameters are the default parameters for peptide sequence comparisons (along with no penalty for end gaps).

Preferred parameters for polynucleotide comparison include the following:

(1) Algorithm: Needleman and Wunsch, *J. Mol Biol.* 48:443-453 (1970)

Comparison matrix: matches=+10, mismatch=0

Gap Penalty: 50

Gap Length Penalty: 3

Available as: The "gap" program from Genetics Computer Group, Madison Wis. These are the default parameters for nucleic acid sequence comparisons.

By way of example, a polynucleotide sequence may be identical to another sequence, that is 100% identical, or it may include up to a certain integer number of nucleotide alterations as compared to the reference sequence. Such alterations are selected from the group consisting of at least one nucleotide deletion, substitution, including transition and transversion, or insertion, and wherein the alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the sequence by the numerical percent of the respective percent identity (divided by 100) and subtracting that product from the total number of nucleotides in the sequence, or:

$n_n \le x_n - (x_n \cdot y)$, wherein $n_n$ is the number of nucleotide alterations, $x_n$ is the total number of nucleotides in sequence, and y is, for instance, 0.70 for 70%, 0.80 for 80%, 0.85 for 85%, 0.90 for 90%, 0.95 for 95%, etc., and wherein any non-integer product of $x_n$ and y is rounded down to the nearest integer prior to subtracting from $x_n$.

Alterations of a polynucleotide sequence encoding the SEQ ID NOs above may create nonsense, missense or frameshift mutations in this coding sequence and thereby alter the polypeptide encoded by the polynucleotide following such alterations. Similarly, a polypeptide sequence may be identical to the reference sequence of the SEQ ID NOs above, that is be 100% identical, or it may include up to a certain integer number of amino acid alterations as compared to the reference sequence such that the percentage identity is less than 100%. Such alterations are selected from the group consisting of at least one amino acid deletion, substitution, including conservative and non-conservative substitution, or insertion, and wherein the alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the SEQ ID NOs above by the numerical percent of the respective percent identity (divided by 100) and then subtracting that product from the total number of amino acids in the SEQ ID NOs above, or:

$n_a \le x_a - (x_a \cdot y)$, wherein $n_a$ is the number of amino acid alterations, $x_a$ is the total number of amino acids in the SEQ ID NOs above, and y is, for instance 0.70 for 70%, 0.80 for 80%, 0.85 for 85% etc., and wherein any non-integer produce of $x_a$ and y is rounded down to the nearest integer prior to subtracting it from $x_a$.

Exemplary heavy chain and light chain variable regions sequences and portions thereof are provided in the SEQ ID NOs above. The antibodies of the present invention, or specified variants thereof, can comprise any number of contiguous amino acid residues from an antibody of the present invention, wherein that number is selected from the group of integers consisting of from 10-100% of the number of contiguous residues in an anti-IL-23 antibody. Optionally, this subsequence of contiguous amino acids is at least about 10, 20, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, or 5.

As those of skill will appreciate, the present invention includes at least one biologically active antibody of the present invention. Biologically active antibodies have a specific activity at least 20%, 30%, or 40%, and, preferably, at least 50%, 60%, or 70%, and, most preferably, at least 80%, 90%, or 95%-100% or more (including, without limitation, up to 10 times the specific activity) of that of the native (non-synthetic), endogenous or related and known antibody. Methods of assaying and quantifying measures of enzymatic activity and substrate specificity are well known to those of skill in the art.

In another aspect, the invention relates to human antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example, $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N, N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-$\Delta$9-octadecanoate ($C_{18}$, oleate), all cis-$\Delta$5, 8, 11, 14-eicosatetraenoate ($C_{20}$, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably, one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups, such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., *Bioconjugate Techniques*, Academic Press: San Diego, CA (1996)). An activating group can be bonded directly to the organic group (e.g., hydrophilic polymer, fatty acid, fatty acid ester), or through a linker moiety, for example, a divalent $C_1$-$C_{12}$ group wherein one or more carbon atoms can be replaced by a heteroatom, such as oxygen, nitrogen or sulfur. Suitable linker moieties include, for example, tetraethylene glycol, —$(CH_2)_3$—, —NH—$(CH_2)_6$—NH—, —$(CH_2)_2$—NH— and —$CH_2$—O—$CH_2$—$CH_2$—O—$CH_2$—$CH_2$—O—$C_H$—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate, as described, or can be reacted with maleic anhydride and the resulting product cyclized to produce an activated maleimido derivative of the fatty acid. (See, for example, Thompson, et al., WO 92/16221, the entire teachings of which are incorporated herein by reference.) The modified antibodies can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention.

Modified human antibodies and antigen-binding fragments comprising an organic moiety that is bonded to specific sites of an antibody of the present invention can be prepared using suitable methods, such as reverse proteolysis (Fisch et al., *Bioconjugate Chem.*, 3:147-153 (1992); Werlen et al., *Bioconjugate Chem.*, 5:411-417 (1994); Kumaran et al., *Protein Sci.* 6(10):2233-2241 (1997); Itoh et al., *Bioorg. Chem.*, 24(1): 59-68 (1996); Capellas et al., *Biotechnol. Bioeng.*, 56(4):456-463 (1997)), and the methods described in Hermanson, G. T., *Bioconjugate Techniques*, Academic Press: San Diego, CA (1996).

The method of the present invention also uses an anti-IL-23 antibody composition comprising at least one, at least two, at least three, at least four, at least five, at least six or more anti-IL-23 antibodies thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the anti-IL-23 antibody amino acid sequence selected from the group consisting of 70-100% of the contiguous amino acids of the SEQ ID NOs above, or specified fragments, domains or variants thereof. Preferred anti-IL-23 antibody compositions include at least one or two full length, fragments, domains or variants as at least one CDR or LBP containing portions of the anti-IL-23 antibody sequence described herein, for example, 70-100% of the SEQ ID NOs above, or specified fragments, domains or variants thereof. Further preferred compositions comprise, for example, 40-99% of at least one of 70-100% of the SEQ ID NOs above, etc., or specified fragments, domains or variants thereof. Such composition percentages are by weight, volume, concentration, molarity, or molality as liquid or dry solutions, mixtures, suspension, emulsions, particles, powder, or colloids, as known in the art or as described herein.

Antibody Compositions Comprising Further Therapeutically Active Ingredients

The antibody compositions used in the method of the invention can optionally further comprise an effective amount of at least one compound or protein selected from at least one of an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplastic, an immunomodulation drug, an ophthalmic, otic or nasal drug, a topical drug, a nutritional drug or the like. Such drugs are well known in the art, including formulations, indications, dosing and administration for each presented herein (see, e.g., *Nursing* 2001 *Handbook of Drugs*, 21$^{st}$ edition, Springhouse Corp., Springhouse, P A, 2001; *Health Professional's Drug Guide* 2001, ed., Shannon, Wilson, Stang, Prentice-Hall, Inc, Upper Saddle River, NJ; *Pharmcotherapy Handbook*, Wells et al., ed., Appleton & Lange, Stamford, CT, each entirely incorporated herein by reference).

By way of example of the drugs that can be combined with the antibodies for the method of the present invention, the anti-infective drug can be at least one selected from amebicides or at least one antiprotozoals, anthelmintics, antifungals, antimalarials, antituberculotics or at least one antileprotics, aminoglycosides, penicillins, cephalosporins, tetracyclines, sulfonamides, fluoroquinolones, antivirals, macrolide anti-infectives, and miscellaneous anti-infectives. The hormonal drug can be at least one selected from corticosteroids, androgens or at least one anabolic steroid, estrogen or at least one progestin, gonadotropin, antidiabetic drug or at least one glucagon, thyroid hormone, thyroid hormone antagonist, pituitary hormone, and parathyroid-like drug. The at least one cephalosporin can be at least one selected from cefaclor, cefadroxil, cefazolin sodium, cefdinir, cefepime hydrochloride, cefixime, cefmetazole sodium, cefonicid sodium, cefoperazone sodium, cefotaxime sodium, cefotetan disodium, cefoxitin sodium, cefpodoxime proxetil, cefprozil, ceftazidime, ceftibuten, ceftizoxime sodium, ceftriaxone sodium, cefuroxime axetil, cefuroxime sodium, cephalexin hydrochloride, cephalexin monohydrate, cephradine, and loracarbef.

The at least one coricosteroid can be at least one selected from betamethasone, betamethasone acetate or betamethasone sodium phosphate, betamethasone sodium phosphate, cortisone acetate, dexamethasone, dexamethasone acetate, dexamethasone sodium phosphate, fludrocortisone acetate, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, prednisolone, prednisolone acetate, prednisolone sodium phosphate, prednisolone tebutate, prednisone, triamcinolone, triamcinolone acetonide, and triamcinolone diacetate. The at least one androgen or anabolic steroid can be at least one selected from danazol, fluoxymesterone, methyltestosterone, nandrolone decanoate, nandrolone phenpropionate, testosterone, testosterone cypionate, testosterone enanthate, testosterone propionate, and testosterone transdermal system.

The at least one immunosuppressant can be at least one selected from azathioprine, basiliximab, cyclosporine, daclizumab, lymphocyte immune globulin, muromonab-CD3, mycophenolate mofetil, mycophenolate mofetil hydrochloride, sirolimus, and tacrolimus.

The at least one local anti-infective can be at least one selected from acyclovir, amphotericin B, azelaic acid cream, bacitracin, butoconazole nitrate, clindamycin phosphate, clotrimazole, econazole nitrate, erythromycin, gentamicin sulfate, ketoconazole, mafenide acetate, metronidazole (topical), miconazole nitrate, mupirocin, naftifine hydrochloride, neomycin sulfate, nitrofurazone, nystatin, silver sulfadiazine, terbinafine hydrochloride, terconazole, tetracycline hydrochloride, tioconazole, and tolnaftate. The at least one scabicide or pediculicide can be at least one selected from crotamiton, lindane, permethrin, and pyrethrins. The at least one topical corticosteroid can be at least one selected from betamethasone dipropionate, betamethasone valerate, clobetasol propionate, desonide, desoximetasone, dexamethasone, dexamethasone sodium phosphate, diflorasone diacetate, fluocinolone acetonide, fluocinonide, flurandrenolide, fluticasone propionate, halcionide, hydrocortisone, hydrocortisone acetate, hydrocortisone butyrate, hydrocorisone valerate, mometasone furoate, and triamcinolone acetonide. (See, e.g., pp. 1098-1136 of *Nursing* 2001 *Drug Handbook.*)

Anti-IL-23 antibody compositions can further comprise at least one of any suitable and effective amount of a composition or pharmaceutical composition comprising at least one anti-IL-23 antibody contacted or administered to a cell, tissue, organ, animal or patient in need of such modulation, treatment or therapy, optionally further comprising at least one selected from at least one TNF antagonist (e.g., but not limited to a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, eternacept, CDP-571, CDP-870, afelimomab, lenercept, and the like), an antirheumatic (e.g., methotrexate, auranofin, aurothioglucose, azathioprine, etanercept, gold sodium thiomalate, hydroxychloroquine sulfate, leflunomide, sulfasalzine), an immunization, an immunoglobulin, an immunosuppressive (e.g., basiliximab, cyclosporine, daclizumab), a cytokine or a cytokine antagonist. Non-limiting examples of such cytokines include, but are not limited to, any of IL-1 to IL-23 et al. (e.g., IL-1, IL-2, etc.). Suitable dosages are well known in the art. See, e.g., Wells et al., eds., *Pharmacotherapy Handbook,* 2$^{nd}$ Edition, Appleton and Lange, Stamford, CT (2000); PDR Pharmacopoeia, *Tarascon Pocket Pharmacopoeia* 2000, Deluxe Edition, *Tarascon Publishing, Loma Linda, CA* (2000), each of which references are entirely incorporated herein by reference.

Anti-IL-23 antibody compounds, compositions or combinations used in the method of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., *Remington's Pharmaceutical Sciences,* 18$^{th}$ Edition, Mack Publishing Co. (Easton, PA) 1990. Pharmaceutically acceptable carriers can be routinely selected that are suitable for the mode of administration, solubility and/or stability of the anti-IL-23 antibody, fragment or variant composition as well known in the art or as described herein.

Pharmaceutical excipients and additives useful in the present composition include, but are not limited to, proteins, peptides, amino acids, lipids, and carbohydrates (e.g., sugars, including monosaccharides, di-, tri-, tetra-, and oligosaccharides; derivatized sugars, such as alditols, aldonic acids, esterified sugars and the like; and polysaccharides or sugar polymers), which can be present singly or in combination, comprising alone or in combination 1-99.99% by weight or volume. Exemplary protein excipients include serum albumin, such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-IL-23 antibody compositions can also include a buffer or a pH adjusting agent; typically, the buffer is a salt prepared from an organic acid or base. Representative buffers include organic acid salts, such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts, such as citrate.

Additionally, anti-IL-23 antibody compositions can include polymeric excipients/additives, such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates, such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the anti-IL-23 antibody, portion or variant compositions according to the invention are known in the art, e.g., as listed in "Remington: The Science & Practice of Pharmacy," 19th ed., Williams & Williams, (1995), and in the "Physician's Desk Reference," 52nd ed., Medical Economics, Montvale, NJ (1998), the disclosures of which are entirely incorporated herein by reference. Preferred carrier or excipient materials are carbohydrates (e.g., saccharides and alditols) and buffers (e.g., citrate) or polymeric agents. An exemplary carrier molecule is the mucopolysaccharide, hyaluronic acid, which may be useful for intraarticular delivery.

Formulations

As noted above, the invention provides for stable formulations, which preferably comprise a phosphate buffer with saline or a chosen salt, as well as preserved solutions and formulations containing a preservative as well as multi-use preserved formulations suitable for pharmaceutical or veterinary use, comprising at least one anti-IL-23 antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3, 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the method of the invention uses an article of manufacture, comprising packaging material and at least one vial comprising a solution of at least one anti-IL-23 specific antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further uses an article of manufacture, comprising packaging material, a first vial comprising lyophilized anti-IL-23 specific antibody, and a second vial comprising an aqueous diluent of prescribed buffer or preservative, wherein said packaging material comprises a label that instructs a patient to reconstitute the anti-IL-23 specific antibody in the aqueous diluent to form a solution that can be held over a period of twenty-four hours or greater.

The anti-IL-23 specific antibody used in accordance with the present invention can be produced by recombinant means, including from mammalian cell or transgenic preparations, or can be purified from other biological sources, as described herein or as known in the art.

The range of the anti-IL-23 specific antibody includes amounts yielding upon reconstitution, if in a wet/dry system, concentrations from about 1.0 µg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an anti-microbial effect. Such concentrations are dependent on the preservative selected and are readily determined by the skilled artisan.

Other excipients, e.g., isotonicity agents, buffers, antioxidants, and preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably, the formulations of the present invention have a pH between about 6.8 and about 7.8. Preferred buffers include phosphate buffers, most preferably, sodium phosphate, particularly, phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants, such as polysorbate 20 or 80 or poloxamer 184 or 188, Pluronic® polyls, other block copolymers, and chelators, such as EDTA and EGTA, can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations can be prepared by a process which comprises mixing at least one anti-IL-23 specific antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-IL-23 specific antibody and preservative in an aqueous diluent is carried out using conventional dissolution and mixing procedures. To prepare a suitable formulation, for example, a measured amount of at least one anti-IL-23 specific antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The formulations can be provided to patients as clear solutions or as dual vials comprising a vial of lyophilized anti-IL-23 specific antibody that is reconstituted with a second vial containing water, a preservative and/or excipients, preferably, a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present articles of manufacture are useful for administration over a period ranging from immediate to twenty-four hours or greater. Accordingly, the presently claimed articles of manufacture offer significant advantages to the patient. Formulations of the invention can optionally be safely stored at temperatures of from about 2° C. to about 40° C. and retain the biologically activity of the protein for extended periods of time, thus allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The solutions of anti-IL-23 specific antibody can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and, optionally, a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one anti-IL-23 specific antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one anti-IL-23 specific antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising single vial systems include pen-injector devices for delivery of a solution, such as BD Pens, BD Autojector®, Humaject®NovoPen®, B-D®Pen, AutoPen®, and OptiPen®, GenotropinPen®, Genotronorm Pen®, Humatro Pen®, Reco-Pen®, Roferon Pen®, Biojector®, Iject®, J-tip Needle-Free Injector®, Intraject®, Medi-Ject®, Smartject® e.g., as made or developed by Becton Dickensen (Franklin Lakes, NJ, www.bectondickenson.com), Disetronic (Burgdorf, Switzerland, www.disetronic.com; Bioject, Portland, Oregon (www.bioject.com); National Medical Products, Weston Medical (Peterborough, UK, www.weston-medical.com), Medi-Ject Corp (Minneapolis, MN, www.mediject.com), and similary suitable devices. Recognized devices comprising a dual vial system include those pen-injector systems for reconstituting a lyophilized drug in a cartridge for delivery of the reconstituted solution, such as the HumatroPen®. Examples of other devices suitable include pre-filled syringes, auto-injectors, needle free injectors, and needle free IV infusion sets.

The products may include packaging material. The packaging material provides, in addition to the information required by the regulatory agencies, the conditions under which the product can be used. The packaging material of the present invention provides instructions to the patient, as applicable, to reconstitute the at least one anti-IL-23 antibody in the aqueous diluent to form a solution and to use the solution over a period of 2-24 hours or greater for the two vial, wet/dry, product. For the single vial, solution product, pre-filled syringe or auto-injector, the label indicates that such solution can be used over a period of 2-24 hours or greater. The products are useful for human pharmaceutical product use.

The formulations used in the method of the present invention can be prepared by a process that comprises mixing an anti-IL-23 antibody and a selected buffer, preferably, a phosphate buffer containing saline or a chosen salt. Mixing the anti-IL-23 antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The method of the invention provides pharmaceutical compositions comprising various formulations useful and acceptable for administration to a human or animal patient. Such pharmaceutical compositions are prepared using water at "standard state" as the diluent and routine methods well known to those of ordinary skill in the art. For example, buffering components such as histidine and histidine monohydrochloride hydrate, may be provided first followed by the addition of an appropriate, non-final volume of water diluent, sucrose and polysorbate 80 at "standard state." Isolated antibody may then be added. Last, the volume of the pharmaceutical composition is adjusted to the desired final volume under "standard state" conditions using water as the diluent. Those skilled in the art will recognize a number of other methods suitable for the preparation of the pharmaceutical compositions.

The pharmaceutical compositions may be aqueous solutions or suspensions comprising the indicated mass of each constituent per unit of water volume or having an indicated pH at "standard state." As used herein, the term "standard state" means a temperature of 25° C.+/−2° C. and a pressure of 1 atmosphere. The term "standard state" is not used in the art to refer to a single art recognized set of temperatures or pressure, but is instead a reference state that specifies temperatures and pressure to be used to describe a solution or suspension with a particular composition under the reference "standard state" conditions. This is because the volume of a solution is, in part, a function of temperature and pressure. Those skilled in the art will recognize that pharmaceutical compositions equivalent to those disclosed here can be produced at other temperatures and pressures.

Whether such pharmaceutical compositions are equivalent to those disclosed here should be determined under the "standard state" conditions defined above (e.g. 25° C.+/−2° C. and a pressure of 1 atmosphere).

Importantly, such pharmaceutical compositions may contain component masses "about" a certain value (e.g. "about 0.53 mg L-histidine") per unit volume of the pharmaceutical composition or have pH values about a certain value. A component mass present in a pharmaceutical composition or pH value is "about" a given numerical value if the isolated antibody present in the pharmaceutical composition is able to bind a peptide chain while the isolated antibody is present in the pharmaceutical composition or after the isolated antibody has been removed from the pharmaceutical composition (e.g., by dilution). Stated differently, a value, such as a component mass value or pH value, is "about" a given numerical value when the binding activity of the isolated antibody is maintained and detectable after placing the isolated antibody in the pharmaceutical composition.

Competition binding analysis is performed to determine if the IL-23 specific mAbs bind to similar or different epitopes and/or compete with each other. Abs are individually coated on ELISA plates. Competing mAbs are added, followed by the addition of biotinylated hrIL-23. For positive control, the same mAb for coating may be used as the competing mAb ("self-competition"). IL-23 binding is detected using streptavidin. These results demonstrate whether the mAbs recognize similar or partially overlapping epitopes on IL-23.

One aspect of the method of the invention administers to a patient a pharmaceutical composition comprising In one embodiment of the pharmaceutical compositions, the isolated antibody concentration is from about 77 to about 104 mg per ml of the pharmaceutical composition. In another embodiment of the pharmaceutical compositions the pH is from about 5.5 to about 6.5.

The stable or preserved formulations can be provided to patients as clear solutions or as dual vials comprising a vial of lyophilized at least one anti-IL-23 antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

Other formulations or methods of stabilizing the anti-IL-23 antibody may result in other than a clear solution of lyophilized powder comprising the antibody. Among non-clear solutions are formulations comprising particulate suspensions, said particulates being a composition containing the anti-IL-23 antibody in a structure of variable dimension and known variously as a microsphere, microparticle, nanoparticle, nanosphere, or liposome. Such relatively homogenous, essentially spherical, particulate formulations containing an active agent can be formed by contacting an aqueous phase containing the active agent and a polymer and a nonaqueous phase followed by evaporation of the nonaqueous phase to cause the coalescence of particles from the aqueous phase as taught in U.S. Pat. No. 4,589,330. Porous microparticles can be prepared using a first phase containing active agent and a polymer dispersed in a continuous solvent and removing said solvent from the suspension by freeze-drying or dilution-extraction-precipitation as taught in U.S. Pat. No. 4,818,542. Preferred polymers for such preparations are natural or synthetic copolymers or polymers selected from the group consisting of gleatin agar, starch, arabinogalactan, albumin, collagen, polyglycolic acid, polylactic aced, glycolide-L(−) lactide poly(episilon-caprolactone, poly(epsilon-caprolactone-CO-lactic acid), poly(epsilon-caprolactone-CO-glycolic acid), poly(8-hydroxy butyric acid), polyethylene oxide, polyethylene, poly(alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate). Particularly preferred polymers are polyesters, such as polyglycolic acid, polylactic aced, glycolide-L(−) lactide poly(episilon-caprolactone, poly(epsilon-caprolactone-CO-lactic acid), and poly(epsilon-caprolactone-CO-glycolic acid. Solvents useful for dissolving the polymer and/or the active include: water, hexafluoroisopropanol, methylenechloride, tetrahydrofuran, hexane, benzene, or hexafluoroacetone sesquihydrate. The process of dispersing the active containing phase with a second phase may include pressure forcing said first phase through an orifice in a nozzle to affect droplet formation.

Dry powder formulations may result from processes other than lyophilization, such as by spray drying or solvent extraction by evaporation or by precipitation of a crystalline composition followed by one or more steps to remove aqueous or nonaqueous solvent. Preparation of a spray-dried antibody preparation is taught in U.S. Pat. No. 6,019,968. The antibody-based dry powder compositions may be produced by spray drying solutions or slurries of the antibody and, optionally, excipients, in a solvent under conditions to provide a respirable dry powder. Solvents may include polar compounds, such as water and ethanol, which may be readily dried. Antibody stability may be enhanced by performing the spray drying procedures in the absence of oxygen, such as under a nitrogen blanket or by using nitrogen as the drying gas. Another relatively dry formulation is a dispersion of a plurality of perforated microstructures dispersed in a suspension medium that typically comprises a hydrofluoroalkane propellant as taught in WO 9916419. The stabilized dispersions may be administered to the lung of a patient using a metered dose inhaler. Equipment useful in the commercial manufacture of spray dried medicaments are manufactured by Buchi Ltd. or Niro Corp.

An anti-IL-23 antibody in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Therapeutic Applications

The present invention also provides a method for modulating or treating Crohn's disease, in a cell, tissue, organ, animal, or patient, as known in the art or as described herein, using at least one IL-23 antibody of the present invention, e.g., administering or contacting the cell, tissue, organ, animal, or patient with a therapeutic effective amount of IL-23 specific antibody.

Any method of the present invention can comprise administering an effective amount of a composition or pharmaceutical composition comprising an anti-IL-23 antibody to a cell, tissue, organ, animal or patient in need of such modulation, treatment or therapy. Such a method can optionally further comprise co-administration or combination therapy for treating such diseases or disorders, wherein the administering of said at least one anti-IL-23 antibody, specified portion or variant thereof, further comprises administering, before concurrently, and/or after, at least one selected from at least one TNF antagonist (e.g., but not limited to, a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, eternacept (Enbrel™), adalimulab (Humira™), CDP-571, CDP-870, afelimomab, lenercept, and the like), an antirheumatic (e.g., methotrexate, auranofin, aurothioglucose, azathioprine, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Suitable dosages are well known in the art. See, e.g., Wells et al., eds., *Pharmacotherapy Handbook, 2nd* Edition, Appleton and Lange, Stamford, CT (2000); PDR Pharmacopoeia, *Tarascon Pocket Pharmacopoeia* 2000, Deluxe Edition, *Tarascon Publishing, Loma Linda, C A* (2000); *Nursing* 2001 *Handbook of Drugs*, 21$^{st}$ edition, Springhouse Corp., Springhouse, P A, 2001; *Health Professional's Drug Guide* 2001, ed., Shannon, Wilson, Stang, Prentice-Hall, Inc, Upper Saddle River, NJ, each of which references are entirely incorporated herein by reference.

Therapeutic Treatments

Typically, treatment of Crohn's disease is affected by administering an effective amount or dosage of an anti-IL-23 antibody composition that total, on average, a range from at least about 0.01 to 500 milligrams of an anti-IL-23 antibody per kilogram of patient per dose, and, preferably, from at least about 0.1 to 100 milligrams antibody/kilogram of patient per single or multiple administration, depending upon the specific activity of the active agent contained in the composition. Alternatively, the effective serum concentration can comprise 0.1-5000 μg/ml serum concentration per single or multiple administrations. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 μg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and, preferably, 0.1 to 10 milligrams per kilogram per administration or in sustained release form is effective to obtain desired results.

As a non-limiting example, treatment of humans or animals can be provided as a one-time or periodic dosage of at least one antibody of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or, alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or, alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.001 milligram to about 500 milligrams of active ingredient per unit or container. In these pharmaceutical compositions the active ingredient will ordinarily be present in an amount of about 0.5-99.999% by weight based on the total weight of the composition.

For parenteral administration, the antibody can be formulated as a solution, suspension, emulsion, particle, powder, or lyophilized powder in association, or separately provided, with a pharmaceutically acceptable parenteral vehicle. Examples of such vehicles are water, saline, Ringer's solution, dextrose solution, and 1-10% human serum albumin. Liposomes and nonaqueous vehicles, such as fixed oils, can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Alternative Administration

Many known and developed modes can be used according to the present invention for administering pharmaceutically effective amounts of an anti-IL-23 antibody. While pulmonary administration is used in the following description, other modes of administration can be used according to the present invention with suitable results. IL-23 specific antibodies of the present invention can be delivered in a carrier, as a solution, emulsion, colloid, or suspension, or as a dry powder, using any of a variety of devices and methods suitable for administration by inhalation or other modes described here within or known in the art.

Parenteral Formulations and Administration

Formulations for parenteral administration can contain as common excipients sterile water or saline, polyalkylene glycols, such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent, such as aqueous solution, a sterile injectable solution or suspension in a solvent. As the usable vehicle or solvent, water, Ringer's solution, isotonic saline, etc. are allowed; as an ordinary solvent or suspending solvent, sterile involatile oil can be used. For these purposes, any kind of involatile oil and fatty acid can be used, including natural or synthetic or semisynthetic fatty oils or fatty acids; natural or synthetic or semi-synthtetic mono- or di- or tri-glycerides. Parental administration is known in the art and includes, but is not limited to, conventional means of injections, a gas pressured needleless injection device as described in U.S. Pat. No. 5,851,198, and a laser perforator device as described in U.S. Pat. No. 5,839,446 entirely incorporated herein by reference.

Alternative Delivery

The invention further relates to the administration of an anti-IL-23 antibody by parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal means. An anti-IL-23 antibody composition can be prepared for use for parenteral (subcutaneous, intramuscular or intravenous) or any other administration particularly in the form of liquid solutions or suspensions; for use in vaginal or rectal administration particularly in semisolid forms, such as, but not limited to, creams and suppositories; for buccal, or sublingual administration, such as, but not limited to, in the form of tablets or capsules; or intranasally, such as, but not limited to, the form of powders, nasal drops or aerosols or certain agents; or transdermally, such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement;" Hsieh, D. S., Eds., pp. 59-90 (Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways, such as electroporation, or to increase the mobility of charged drugs through the skin, such as iontophoresis, or application of ultrasound, such as sonophoresis (U.S. Pat. Nos. 4,309,989 and 4,767,402) (the above publications and patents being entirely incorporated herein by reference).

Having generally described the invention, the same will be more readily understood by reference to the following Examples, which are provided by way of illustration and are not intended as limiting. Further details of the invention are illustrated by the following non-limiting Examples. The disclosures of all citations in the specification are expressly incorporated herein by reference.

Example 1

Preclinical Evidence Implicating IL-23 as a Target in Crohn's Disease

Genetic and animal model studies have explored the contribution of IL-12 and IL-23 in driving the pathophysiology of Crohn's disease. The results indicate that IL-23 plays a predominant role in inflammatory bowel disease (IBD) and emerging evidence suggests that blocking IL-23 alone may be a more effective strategy than blocking both IL-12 and IL-23.

Initial observations from genetic and animal model data suggest that Crohn's disease is mediated by IL-12 and/or IL-23, potentially through the Th1 and Th17 pathways they induce, respectively. However, increasing evidence suggests a predominant role for IL-23 in Crohn's disease. Genome-wide association studies identified polymorphisms in the IL-23R gene that are associated with Crohn's disease. The role of IL-23 in driving intestinal inflammation has been shown in several mouse models. Mice treated with anti-IL-23 antibodies exhibited attenuated inflammation, and mice with a genetic deletion of the p19 subunit of IL-23 are protected in several models of intestinal inflammation.

Clinical Evidence Establishing Proof of Concept for Targeting IL-23 in Crohn's Disease The potential therapeutic role of IL-23 in Crohn's disease was first established by clinical studies of IL-12/23p40 antagonists (briakinumab and ustekinumab). Ustekinumab (STELARA®) was recently approved for the treatment of moderately to severely active Crohn's disease. While these programs demonstrated that blockade of both IL-12 and IL-23 is effective in treating Crohn's disease, they could not ascertain the relative contributions of the 2 cytokines.

More recent studies of 2 anti-IL-23 antagonists, risankizumab (previously BI-655066) and brazikumab (formerly MEDI2070, AMG 139), reported Phase 2 results demonstrating efficacy of IL-23 blockade in participants with moderately to severely active Crohn's disease. The magnitude of efficacy observed in each of these studies suggests the potential for improved efficacy compared with ustekinumab (anti-IL-12/23), recognizing the limitations of cross-study comparisons as well as the comparatively small size of the IL-23 Phase 2 studies.

Clinical Experience with IL-12/23-Targeted Therapy (Ustekinumab) in Crohn's Disease The ustekinumab Phase 3 program in Crohn's disease included two 8-week studies evaluating the efficacy and safety of ustekinumab intravenous (IV) induction, and one maintenance study evaluating the efficacy and safety of ustekinumab subcutaneous (SC) maintenance, for a total duration of 52 weeks of treatment. Ustekinumab was evaluated in the full spectrum of biologic-eligible patients with Crohn's disease, ie, those who were conventional therapy failures and those who were biologic therapy failures. After a single ustekinumab ~6 mg/kg IV induction dose at Week 0, approximately 21% and 40% of BIO-failure and CON-failure participants, respectively (versus approximately 7% and 20% of placebo-treated participants, respectively), achieved clinical remission at Week 8 (as evaluated by the Crohn's Disease Activity Index [CDAI]). Among participants who responded to ustekinumab IV induction and were rerandomized to receive ustekinumab SC maintenance 90 mg every 8 weeks (q8w) or 90 mg every 12 weeks (q12w), approximately 53% and 49% of participants were in clinical remission at Week 52, respectively, compared with 36% of participants who received placebo maintenance.

Clinical Experience with IL-23-Targeted Therapy in Crohn's Disease

Recent Phase 2 studies of 2 IL-23 mAbs, risankizumab and brazikumab, demonstrated their efficacy in improving clinical signs and symptoms, reducing inflammatory biomarkers, and improving endoscopic findings in participants primarily with biologic-refractory Crohn's disease.

Cross-study comparisons of clinical remission rates with the IL-23 blockers suggest the potential for improved efficacy compared with ustekinumab. It is notable that the induction doses used in the studies of both risankizumab (200 and 600 mg IV at Weeks 0, 4, 8) and brazikumab (700 mg IV at Weeks 0, 4) were considerably higher than approved ustekinumab dosing (~6 mg/kg IV at Week 0). A cross-compound meta-analysis suggests that the risankizumab dosing, in particular, may be at the higher end of the dose-response curve.

Furthermore, the Phase 2 study with risankizumab also suggested the potential that response rates may not reach maximum until after 6 months of treatment. With doses of 600 mg IV every 4 weeks (q4w) for up to 6 months, clinical remission rates of approximately 50% were observed in all-treated patients, substantially higher than remission rates previously reported for other agents, including ustekinumab, in similar study populations at similar follow-up time points. Of those participants who were in remission at 6 months and who continued risankizumab maintenance treatment (180 mg SC q8w), approximately 70% were in remission at 1 year.

Overall Rationale for Guselkumab in Crohn's Disease

In summary, the collective genetic and preclinical evidence implicates the prominent role of selectively targeting IL-23 in modulating the underlying pathophysiology of IBD. The available clinical experience of 2 IL-23 antagonists and the established evidence from an approved IL-12/23 antagonist (ustekinumab) have demonstrated proof of mechanism and proof of concept, respectively, for targeting IL-23 in the treatment of Crohn's disease. Together, the available evidence provide support for investigating guselkumab in the treatment of Crohn's disease.

Primary Endpoint

The primary endpoint is clinical remission at Week 12 (defined as CDAI score <150). For this endpoint, comparisons of each guselkumab group with placebo will be made.

Major Secondary Endpoints

The major secondary endpoints are described below.

Clinical remission at Week 48 (defined as CDAI<150)

Durable clinical remission at Week 48 (defined as CDAI<150 for ≥80% of all visits between Week 12 and Week 48 [ie, at least 8 of 10 visits], which must include Week 48)

Corticosteroid-free clinical remission at Week 48 (defined as CDAI score <150 at Week 48 and not receiving corticosteroids at Week 48)

PRO-2 remission at Week 12 (defined as an AP mean daily score at or below 1 AND SF mean daily score at or below 3, ie, AP≤1 and SF≤3)

PRO-2 remission at Week 48

Endoscopic response at Week 12 (defined as at least 50% improvement from baseline in SES-CD score or SES-CD score ≤2)

Endoscopic response at Week 48

Fatigue response at Week 12 (based on the PROMIS Fatigue Short Form 7a; to be defined in the SAP)

The short-term endpoints at Week 12 will be based on comparisons of each guselkumab group with the placebo group, and the long-term endpoints at Week 48 will be based on comparisons of each guselkumab group with the ustekinumab group.

From a nonclinical perspective, the risk to Crohn's disease patients is considered low when guselkumab is administered IV once every 4 weeks at doses up to 1200 mg (approximately 16 mg/kg in humans) followed by the proposed maintenance doses of up to 200 mg SC q4w, based on no adverse findings observed in cynomolgus monkeys following 5 weeks of once-weekly subchronic IV dosing at 50 mg/kg and 24 weeks of chronic once-weekly SC dosing. As summarized above, the actual exposure data (area under the serum concentration versus time curve [AUC]) achieved in monkeys relative to the predicted Week 8 to Week 12 IV clinical induction dosing interval AUC, or steady-state SC maintenance interval AUC (both normalized to weekly dosing to compare with the monkey dosing interval) provide ample exposure margins for the proposed clinical doses. This is further supported by the fact that guselkumab is a late-stage biotherapeutic with a good clinical safety profile in participants with plaque psoriasis, with data generated primarily at 100 mg SC, but also at doses up to 300 mg SC and 10 mg/kg IV in a limited number of patients with plaque psoriasis and in healthy normal volunteers, respectively, during Phase 1 of clinical development. Lastly, risankizumab (an IL-23 inhibitor with clinical potency comparable to guselkumab) has been studied in patients with Crohn's disease at up to 600 mg IV given q4w for 6 months and was reported to be well-tolerated.

Guselkumab has undergone extensive nonclinical and clinical development. The collective efficacy and safety results of the Phase 1, Phase 2, and Phase 3 clinical studies in healthy volunteers and patients with plaque psoriasis and the recent regulatory approval for the plaque psoriasis indication established a favorable benefit-risk profile for guselkumab in the treatment of plaque psoriasis. This clinical experience provided support to the ongoing development of guselkumab in other inflammatory diseases such as PsA, GPP, EP, and PPP.

Available animal and human data support the critical role of IL-23 in the pathogenesis of Crohn's disease, and studies with other anti-IL-23 mAbs suggest that selective targeting of IL-23 may achieve higher levels of efficacy than that observed with other mechanisms of action, including ustekinumab, in patients with moderately to severely active Crohn's disease.

Clinical data with ustekinumab and other anti-IL-23 mAbs suggest that maximum efficacy in Crohn's disease may require higher doses and exposures than those used in psoriasis. For example, initial dosing of ustekinumab in Crohn's disease (~6 mg/kg IV in a 70 kg patient) is approximately 4-fold higher than in psoriasis (45 mg SC at Week 0 and Week 4). Therefore, induction doses up to 1200 mg IV given q4w for 3 doses and maintenance doses up to 200 mg SC q4w will be studied in the Phase 2 portion of this trial to evaluate whether higher doses and exposures of guselkumab are needed for maximum efficacy in Crohn's disease. Data from non-clinical toxicology studies provide adequate exposure margins for the proposed clinical doses in this protocol. In addition, comparable doses/exposures have been previously evaluated in the Phase 2 studies of 2 other anti-IL-23 mAbs, and no significant safety concerns have been reported after treatment through 1 year.

The approved dose regimen of guselkumab in psoriasis (100 mg SC at Week 0 and Week 4, and then q8w) has been demonstrated to have a favorable safety profile, and dose regimens as high as 200 mg SC q8w have been shown to have favorable safety in a Phase 2 trial in rheumatoid arthritis. The main risk is infection. Other potential safety concerns, also described in greater detail in the guselkumab IB, are based on guselkumab being an immunomodulatory mAb and include malignancy and hypersensitivity. Since the higher dose regimens of guselkumab (as proposed in this protocol) have not been previously studied, safety will be evaluated in an initial cohort of 25 patients by an independent Data Monitoring Committee (DMC).

The early safety evaluation of the initial cohort will ensure acceptable safety for continued study of the proposed Phase 2 and Phase 3 dose regimens in larger numbers of patients, and the ongoing unblinded safety assessments by the DMC throughout the Phase 2 and 3 studies will ensure patient safety in the overall development program.

Active Comparator: Ustekinumab

Ustekinumab (STELARA) is the active comparator in this protocol. Ustekinumab is a human IgG1 kappa mAb that binds with high affinity and specificity to the p40 subunit common to both human IL-12 and human IL-23. Ustekinumab is an approved treatment for moderately to severely active Crohn's disease in adult patients in several countries including the US, Canada, and the EU; submissions for regulatory approval of the Crohn's disease indication are currently under review in a number of countries globally. The proposed induction and maintenance dosing of ustekinumab in this protocol is consistent with the currently approved country labels globally, and is consistent with the dose regimens evaluated in the ustekinumab Phase 3 clinical development program in Crohn's disease that established the efficacy and safety of ustekinumab in patients with moderately to severely active Crohn's disease.

Phase 2 Dose-Ranging Study (GALAXI 1)
Objectives
Primary Objectives
    To evaluate the clinical efficacy of guselkumab in participants with Crohn's disease
    To evaluate the safety of guselkumab
Secondary Objectives
    To evaluate the dose-response of guselkumab to inform dose selection for the Phase 3 portion of this protocol
    To evaluate the efficacy of guselkumab on endoscopic improvement
    To evaluate the pharmacokinetics (PK), immunogenicity, and pharmacodynamics (PD) of guselkumab therapy, including changes in C-reactive protein (CRP) and fecal calprotectin
Other Objectives
    To evaluate the impact of guselkumab on health-related quality of life (HRQOL) and health economics outcome measures
    To evaluate the efficacy of guselkumab on histologic improvement
    To evaluate the impact of treatment with guselkumab on intestinal mucosal gene expression profiles and cellular composition associated with Crohn's disease
Endpoints The primary endpoint and major secondary endpoints evaluate the short-term efficacy of guselkumab versus placebo. These endpoints are described below.

Primary Endpoint
    Change from baseline in the CDAI score at Week 12.
Major Secondary Endpoints
    Clinical remission at Week 12 (defined as CDAI score <150).
    Clinical response at Week 12 (defined as ≥100-point reduction from baseline in CDAI score or CDAI score <150).
    PRO-2 remission at Week 12 (defined as an abdominal pain [AP] mean daily score at or below 1 AND stool frequency [SF] mean daily score at or below 3, ie, AP≤1 and SF≤3).
    Clinical-biomarker response at Week 12 (clinical response based on CDAI score and >50% reduction from baseline in CRP or fecal calprotectin).
    Endoscopic response at Week 12 (defined as at least 50% improvement from baseline in the Simple Endoscopic Score for Crohn's Disease [SES-CD] or SES-CD score ≤2)
Hypothesis The primary hypothesis for GALAXI 1 is that guselkumab is superior to placebo in inducing a reduction from baseline in CDAI score in participants with moderately to severely active Crohn's disease.

Phase 3 Dose-Confirming Studies (GALAXI 2 and GALAXI 3)

GALAXI 2 and GALAXI 3 are identical studies and have the same objectives and endpoints, as
Objectives
Primary Objectives
    To evaluate the clinical efficacy of guselkumab in participants with Crohn's disease
    To evaluate the safety of guselkumab
Secondary Objectives
    To evaluate the efficacy of guselkumab on endoscopic improvement
    To evaluate the impact of guselkumab on HRQOL
    To evaluate the PK, immunogenicity, and PD of guselkumab therapy, including changes in CRP and fecal calprotectin
Other Objectives
    To evaluate the impact of guselkumab on health economics outcome measures
    To evaluate the efficacy of guselkumab on histologic improvement
    To evaluate the impact of treatment with guselkumab on intestinal mucosal gene expression profiles and cellular composition associated with Crohn's disease Endpoints
Primary Endpoint The primary endpoint is clinical remission at Week 12 (defined as CDAI score <150). For this endpoint, comparisons of each guselkumab group with placebo will be made.

Major Secondary Endpoints

The major secondary endpoints are described below.

Clinical remission at Week 48 (defined as CDAI<150)

Durable clinical remission at Week 48 (defined as CDAI<150 for ≥80% of all visits between Week 12 and Week 48 [ie, at least 8 of 10 visits], which must include Week 48)

Corticosteroid-free clinical remission at Week 48 (defined as CDAI score <150 at Week 48 and not receiving corticosteroids at Week 48)

PRO-2 remission at Week 12 (defined as an AP mean daily score at or below 1 AND SF mean daily score at or below 3, ie, AP≤1 and SF≤3)

PRO-2 remission at Week 48

Endoscopic response at Week 12 (defined as at least 50% improvement from baseline in SES-CD score or SES-CD score ≤2)

Endoscopic response at Week 48

Fatigue response at Week 12 (based on the PROMIS Fatigue Short Form 7a; to be defined in the SAP)

The short-term endpoints at Week 12 will be based on comparisons of each guselkumab group with the placebo group, and the long-term endpoints at Week 48 will be based on comparisons of each guselkumab group with the ustekinumab group.

Hypothesis

The primary hypothesis for both GALAXI 2 and GALAXI 3 is that guselkumab is superior to placebo in achieving clinical remission at Week 12 in participants with moderately to severely active Crohn's disease.

GALAXI 2 and GALAXI 3 will also evaluate the relative performance of long-term treatment with guselkumab versus ustekinumab. For the major secondary hypotheses for comparison with ustekinumab, while the ultimate goal is to demonstrate that the efficacy of guselkumab is superior to ustekinumab, an initial test for non-inferiority will also be performed because the overall profile of guselkumab may be favorable compared with ustekinumab (in terms of overall efficacy and safety), even if final results only indicate the relative efficacy is non-inferior to ustekinumab for a certain endpoint.

Study Design
Overall Design

The clinical development program for guselkumab in Crohn's disease will be conducted under this single protocol: a Phase 2/3, randomized, double-blind, placebo- and active-controlled (ustekinumab), parallel-group, multicenter protocol to evaluate the safety and efficacy of guselkumab in participants with moderately to severely active Crohn's disease who have demonstrated an inadequate response or failure to tolerate previous conventional therapy or biologic therapy.

An overview of this clinical development program is described briefly below. Under this protocol, there are 3 separate studies: a 48-week Phase 2 dose-ranging study (ie, GALAXI 1) and 2 identical 48-week Phase 3 confirmatory studies (ie, GALAXI 2 and GALAXI 3). All 3 studies will be conducted using a treat-through study design, ie, participants are randomized to treatment regimens at Week 0 and will remain on that treatment regimen through at least Week 48 of each study, unless otherwise indicated.

In the Phase 2 dose-ranging study (ie, GALAXI 1), the safety and efficacy of guselkumab dose regimens spanning a wide induction and maintenance dose range will be evaluated to support the selection of induction and maintenance dose regimens for confirmatory evaluation in Phase 3. It is estimated that 250 to 500 participants may be required to select the dose regimens that will be evaluated in Phase 3 (GALAXI 2 and GALAXI 3). Therefore, the first 250 participants in GALAXI 1 will be enrolled into an Initial Dose Decision Cohort; an interim analysis (IA) primarily based on this cohort will occur once these participants reach Week 12 (or terminate study participation prior to Week 12). Since data from more participants may be required to inform the dose decision, enrollment will continue and newly enrolled participants (i.e., starting from participant #251) will be randomized into a Transition Cohort while data from the Initial Dose Decision Cohort are being collected and analyzed. The purpose of the Transition Cohort will be to continue accruing safety and efficacy data on the Phase 2 dose regimens without interrupting the study, thereby increasing the size of the overall safety database as well as possibly contributing additional information in making a dose decision should there be uncertainty on dose selection based on the results from the Initial Dose Decision Cohort. It is anticipated that up to 500 participants will be enrolled into GALAXI 1 (ie, 250 in the Initial Dose Decision Cohort and up to 250 in the Transition Cohort) prior to the dose decision. If a dose decision for Phase 3 is not made by the time the $500^{th}$ patient is randomized, enrollment will be paused until a decision for Phase 3 dosing, or a decision to terminate the development program, is made.

This is an operationally seamless protocol, ie, there will be no break in enrollment between the Phase 2 and Phase 3 studies if a dose decision can be made before 500 patients are randomized. Transition from the Phase 2 portion to the Phase 3 portion of the protocol will occur once the dose decision for Phase 3 has been made and implemented. All participants randomized after the dose decision has been implemented will be part of the Phase 3 studies.

In the Phase 3 dose-confirming studies (i.e., GALAXI 2 and GALAXI 3), the safety and efficacy of the selected guselkumab dose regimens will be evaluated. A target of 770 participants will be enrolled in each of the Phase 3 studies, for a total target sample size of 1,540 participants in the Phase 3 portion of the protocol.

Participants who complete the 48-week Phase 2 or Phase 3 studies may be eligible to enter the LTE to receive approximately 2 additional years of treatment.

The overall GALAXI Phase 2/3 protocol will enroll a total of approximately 2,000 participants, with a total duration for each participant of up to approximately 3 years.

Target Population

The target population in all 3 studies under this protocol will be identical and will consist of men or women ≥18 years of age at the time of informed consent with moderately to severely active Crohn's disease (of at least 3 months' duration). Participants must have colitis, ileitis, or ileocolitis previously confirmed by radiography, histology, and/or endoscopy.

Active Disease Criteria

At baseline, participants must have active Crohn's disease, defined as follows:

Clinically Active Crohn's Disease
  a. CDAI score ≥220 but ≤450
  AND EITHER
  b. Mean daily SF count >3, based on the unweighted CDAI component of the number of liquid or very soft stools
  OR
  c. Mean daily AP score >1, based on the unweighted CDAI component of abdominal pain
  AND
2. Endoscopic evidence of ileocolonic Crohn's disease A SES-CD score ≥3, as assessed by central endoscopy reading at the screening endoscopy, which indicates the presence of at least one large ulcer (in the ileum, colon, or both) that results in:
  a. a minimum score of 2 for the component of "size of ulcers"
  AND
  b. a minimum score of 1 for the component of "ulcerated surface".

Within each of the studies, a maximum of 10% of the total enrolled population will be participants who have baseline scores for SES-CD<4 (ie, for participants with isolated ileal disease), or SES-CD<7 (ie, for participants with colonic or ileocolonic disease).

Medication History Criteria

In addition, a broad participant population eligible for systemic therapy will be evaluated in this protocol and will include participants who have demonstrated an inadequate response or failed to tolerate previous conventional therapy or biologic therapy.

Note that participants with prior exposure to IL-12/23 or IL-23 agents are ineligible for entry into this protocol, with the exception of participants who have had limited exposure to and who have not demonstrated failure or intolerance to ustekinumab.

Conventional Therapy Failure or Intolerance (CON-Failure)

Participants must have demonstrated an inadequate response to, or have failed to tolerate, at least 1 of the following conventional Crohn's disease therapies: oral corticosteroids (including prednisone, budesonide, and beclomethasone dipropionate) or the immunomodulators azathioprine (AZA), 6-mercaptopurine (6-MP) or methotrexate (MTX). Participants who have demonstrated corticosteroid dependence (ie, an inability to successfully taper corticosteroids without a return of the symptoms of Crohn's disease) are also eligible. Participants may be naïve to biologic therapy (ie, a TNF antagonist or vedolizumab or ustekinumab) or may have been exposed to biologic therapy but have not demonstrated inadequate response or intolerance.

Within each of the studies, a minimum of 25% and a maximum of 50% of the total enrolled population will be participants who are CON-Failures.

Biologic Therapy Failure or Intolerance (BIO-Failure)

Participants must have demonstrated an inadequate response to, or have failed to tolerate, at least 1 or more biologic therapies (ie, TNF antagonists or vedolizumab) at a dose approved for the treatment of Crohn's disease. Inadequate response is defined as: Primary non-response (i.e., no initial response) or Secondary non-response (i.e., response initially but subsequently lost response). Participants who have demonstrated an inadequate response to, or have failed to tolerate ustekinumab are not eligible.

The use of concomitant and prohibited therapies is described below. In general, concomitant therapies should maintain stable dosing (except for steroid tapering) and new concomitant therapies should not be initiated unless considered medically necessary by the investigator. Corticosteroids will be tapered beginning at Week 12. Initiation of prohibited therapies will result in study intervention discontinuation (SID). Finally, in the event of persistent inadequate response or clinically significant Crohn's disease worsening, discontinuation of study intervention should be strongly considered.

Evaluations

Throughout the 3 studies, efficacy, PK, biomarkers, and safety will be assessed at time points indicated in the appropriate Schedule of Activities.

A pharmacogenomic blood sample will be collected from participants who consent to this component of the protocol (where local regulations permit). Participation in pharmacogenomic research is optional. Deoxyribonucleic acid (DNA) samples will be analyzed for identification of genetic factors that may be associated with clinical response.

An external independent DMC, with defined roles and responsibilities as governed by a DMC charter, will assess the safety of participants across the 3 studies. The DMC's initial responsibility will be careful review of the safety data from the first 25 participants randomized and treated in GALAXI 1. After that, ongoing safety data reviews will continue as specified in the DMC charter. After each review, the DMC will make recommendations to the sponsor about the continuation of the studies.

Phase 2 Dose-Ranging Study (GALAXI 1)

Overview of Phase 2 Study Design and Dose Decision for Phase 3

At Week 0, participants will be randomized in a 1:1:1:1:1 ratio to receive 1 of 3 dose regimens of guselkumab, ustekinumab, or placebo. Participants will be allocated to a treatment group using a permuted block randomization with baseline CDAI score (≤300 or >300) and prior BIO-Failure status (Yes/No) as the stratification variables. A minimum of 25% and a maximum of 50% of the total enrolled population will be CON-Failure participants. In addition, a maximum of 10% of the total enrolled population will have baseline scores for SES-CD<4 (ie, for participants with isolated ileal disease), or SES-CD<7 (ie, for participants with colonic or ileocolonic disease). Allocation to treatment group will be performed using a central randomization center by means of an interactive web response system (IWRS).

It is anticipated that up to 500 participants will be enrolled into GALAXI 1 (i.e., 250 in the Initial Dose Decision Cohort and up to 250 in the Transition Cohort) prior to the dose decision for Phase 3. If a dose decision for Phase 3 is not made by the time the 500$^{th}$ patient is randomized, enrollment will be paused until a decision for Phase 3 dosing, or a decision to terminate the development program, is made.

Interim analyses are planned at Week 12 (and at Week 24, if necessary) after all participants from the Initial Dose Decision Cohort have either completed the Week 12 (or Week 24) visit or terminated study participation prior to the Week 12 (or Week 24) visit to inform the dose decision for Phase 3. At the time of each IA, all available data from both the Initial Dose Decision Cohort and the Transition Cohort will be analyzed, including any data beyond Week 12. Additional data transfers and analyses may be performed at other time points if needed to enable the dose decision for Phase 3. The goal is to select 2 guselkumab dose regimens for confirmatory evaluation in Phase 3.

Treatment Groups

An overview of the 5 treatment groups and their corresponding dosing schemes from Week 0 through Week 48 of the Phase 2 study is provided below.

Dosing Schemes for the 5 Treatment Groups from Week 0 to Week 48 in Phase 2 (Ie, GALAXI 1)

All participants in the Phase 2 study (i.e., Initial Dose Decision Cohort and Transition Cohort) will be randomized to 1 of 5 treatment groups as described below. Participants will remain on their assigned treatment regimens through the end of the 48-week study, except for the Placebo group as outlined below.

Group 1: Guselkumab Regimen 1 (1200 mg IV q4w×3→200 mg SC q4w)

Participants will receive guselkumab 1200 mg IV induction q4w from Week 0 through Week 8 (i.e., total of 3 IV doses). At Week 12, participants will continue treatment with guselkumab 200 mg SC maintenance q4w through Week 44.

Group 2: Guselkumab Regimen 2 (600 mg IV q4w×3→200 mg SC q4w)

Participants will receive guselkumab 600 mg IV induction q4w from Week 0 through Week 8 (ie, total of 3 IV doses). At Week 12, participants will continue treatment with guselkumab 200 mg SC maintenance q4w through Week 44.

Group 3: Guselkumab Regimen 3 (200 mg IV q4w×3→100 mg SC q8w)

Participants will receive guselkumab 200 mg IV induction q4w from Week 0 through Week 8 (ie, total of 3 IV doses). At Week 16, participants will continue treatment with guselkumab 100 mg SC maintenance q8w through Week 40.

Group 4: Active Control, Ustekinumab (~6 mg/kg IV→90 mg SC q8w)

Participants will receive a single ustekinumab IV induction dose at Week 0 (weight-based IV doses approximating 6 mg/kg as outlined below). At Week 8, participants will receive ustekinumab SC maintenance (90 mg SC q8w) through Week 40.

Ustekinumab 260 mg (weight ≤55 kg)
Ustekinumab 390 mg (weight >55 kg and 85 kg)
Ustekinumab 520 mg (weight >85 kg)

Group 5: Placebo→Placebo or Ustekinumab Crossover

Participants will receive placebo IV q4w from Week 0 through Week 8 (ie, total of 3 IV doses). At Week 12, participants will continue treatment based on their clinical response status as follows:

Placebo responders: Continue placebo treatment q4w from Week 12 through Week 44.

Placebo nonresponders: Receive a single ustekinumab IV induction dose at Week 12 (weight-based IV doses approximating 6 mg/kg as outlined above). At Week 20, participants will receive ustekinumab SC maintenance (90 mg SC q8w) through Week 44.

Clinical response is defined as a reduction from baseline (ie, Week 0) in the CDAI score of ≥100 points or being in clinical remission (CDAI<150). To maintain the blind, participants in all treatment groups will be assessed for their clinical response status at Week 12. In addition, placebo administrations (IV and SC) will be given, as appropriate, to maintain the blind throughout the duration of the study. No dosing adjustments are planned for any of the treatment groups from Week 0 through Week 48, except for Group 5 (Placebo) at Week 12 based on clinical response status as described above.

The use of concomitant and prohibited therapies is described below. In general, concomitant therapies should maintain stable dosing (except for steroid tapering) and new concomitant therapies should not be initiated, unless considered medically necessary by the investigator. Corticosteroids will be tapered beginning at Week 12. Initiation of prohibited therapies will result in SID. Finally, in the event of persistent inadequate response or clinically significant Crohn's disease worsening, discontinuation of study intervention should be strongly considered.

All participants who complete the Week 48 evaluations may be eligible to enter the LTE and continue to receive study intervention for approximately 2 additional years (Week 48 to Week 156).

Endpoints and Evaluations

The primary endpoint is change from baseline in the CDAI score at Week 12. The major secondary endpoints are: clinical remission at Week 12, clinical response at Week 12, PRO-2 remission at Week 12, endoscopic response at Week 12, and clinical-biomarker response at Week 12. Analyses of these endpoints will be based on comparisons between each guselkumab group and the placebo group. Additional analyses of endpoints at other time points, including comparisons of guselkumab with ustekinumab at Week 48, will also be performed.

Efficacy, PK, and PD parameters, biomarkers, and safety will be assessed.

Database locks (DBLs) are planned for Week 12 and Week 48. Additional DBLs (e.g., Week 24) may be added as necessary.

Phase 3 Dose-Confirming Studies (GALAXI 2 and GALAXI 3)

Overview of Phase 3 Design

At Week 0, a target of 1,540 participants will be randomly allocated to GALAXI 2 (n=770) or GALAXI 3 (n=770), using a permuted block randomization with baseline CDAI score (≤300 or >300), baseline SES-CD score (≤12 or >12), prior BIO-Failure status (Yes/No), and baseline corticosteroid use (Yes/No) as the stratification variables. Within each stratum, participants in each study will be randomized in a 2:2:2:1 ratio to receive 1 of 2 dose regimens of guselkumab, ustekinumab, or placebo. Within each study (GALAXI 2 and GALAXI 3), a minimum of 25% and a maximum of 50% of the total enrolled population will be participants who are CON-Failures. In addition, a maximum of 10% of the total enrolled population will have baseline scores for SES-CD<4 (ie, for participants with isolated ileal disease) or SES-CD<7 (ie, for participants with colonic or ileocolonic disease). Allocation to treatment groups will be performed using a central randomization center by means of an IWRS.

Groups

The Phase 3 guselkumab dose regimens will be selected based on the efficacy and safety of the induction dose range (i.e., from 200 mg to 1200 mg IV) and maintenance dose range (i.e., from 100 mg SC q8w to 200 SC q4w) evaluated in the Phase 2 study.

Based on the Phase 2 data, 2 guselkumab dose regimens (i.e., IV induction→SC maintenance) will have been selected for confirmatory evaluation in Phase 3. Identical dose regimens are to be evaluated in both Phase 3 studies.

An overview of the 4 treatment groups in the 2 Phase 3 studies and their corresponding dosing schemes from Week 0 through Week 48 are summarized below. Participants will remain on their assigned treatment regimens through the end of the 48-week study, except for the Placebo group as outlined below.

Dosing Schemes for the 4 Treatment Groups from Week 0 to Week 48 in the Phase 3 Studies (i.e., GALAXI 2 and GALAXI 3)

Group 1 and Group 2: Guselkumab Regimen 1 and Guselkumab Regimen 2

Participants will receive guselkumab IV induction q4w from Week 0 through Week 8 (i.e., total of 3 IV doses). Depending on whether the selected SC maintenance dose is given q4w and/or q8w, participants will continue treatment with guselkumab SC maintenance starting at Week 12 through Week 44 (i.e., if q4w regimen) or starting at Week 16 through Week 40 (i.e., if q8w regimen).

Group 3: Active Control—Ustekinumab (~6 mg/kg IV→90 mg SC q8w)

Participants will receive a single ustekinumab IV induction dose at Week 0 (weight-based IV dose approximating 6 mg/kg as outlined below). At Week 8, participants will receive ustekinumab SC maintenance (90 mg SC q8w) through Week 40.

Ustekinumab 260 mg (weight ≤55 kg)
Ustekinumab 390 mg (weight >55 kg and ≤85 kg)
Ustekinumab 520 mg (weight >85 kg)

Group 4: Placebo→Placebo or Ustekinumab Crossover

Participants will receive placebo IV q4w from Week 0 through Week 8 (i.e., total of 3 IV doses). At Week 12, participants will continue treatment based on their clinical response status as follows:

Placebo responders: Continue placebo treatment from Week 12 through Week 44.

Placebo nonresponders: Receive a single ustekinumab IV induction dose at Week 12 (weight-based IV doses approximating 6 mg/kg as outlined above). At Week 20, participants will receive ustekinumab SC maintenance (90 mg SC q8w) through Week 44.

Clinical response is defined as a reduction from baseline (ie, Week 0) in the CDAI score of ≥100 points or being in clinical remission (CDAI<150). To maintain the blind, participants in all treatment groups will be assessed for their clinical response status at Week 12.

In addition, placebo administrations (IV and SC) will be given, as appropriate, to maintain the blind throughout the duration of the study. No dosing adjustments are planned for any of the treatment groups from Week 0 through Week 48, except for Group 4 (Placebo) at Week 12 based on clinical response status as described above.

The use of concomitant and prohibited therapies is described below. In general, concomitant therapies should maintain stable dosing (except for steroid tapering) and new concomitant therapies should not be initiated; unless considered medically necessary by the investigator. Corticosteroids will be tapered beginning at Week 12. Initiation of prohibited therapies will result in SID. Finally, in the event of persistent inadequate response or clinically significant Crohn's disease worsening, discontinuation of study intervention should be strongly considered.

All participants who complete the Week 48 evaluations may be eligible to enter the LTE and continue to receive approximately 2 additional years of treatment.

Endpoints and Evaluations

Both GALAXI 2 and GALAXI 3 have the same primary and major secondary endpoints.

The primary endpoint is clinical remission at Week 12, based on comparisons between guselkumab and placebo. The major secondary endpoints of clinical remission at Week 48, durable clinical remission at Week 48, corticosteroid-free clinical remission at Week 48, PRO-2 remission at Week 48, and endoscopic response at Week 48 are based on comparisons between guselkumab and ustekinumab. The major secondary endpoints of PRO-2 remission at Week 12, endoscopic response at Week 12, and fatigue response at Week 12 are based on comparisons between each guselkumab treatment group and the placebo group.

Efficacy, PK, and PD parameters, biomarkers, and safety will be assessed.

A DBL is planned for Week 48. Additional DBLs may be added if necessary and will be specified in the SAP.

Long-Term Extension

The LTE will be conducted for approximately 2 years, from Week 48 through Week 156.

At Week 48 of GALAXI 1, GALAXI 2, or GALAXI 3, all participants who, in the opinion of the investigator, will continue to benefit from treatment (i.e., based on Week 48 clinical and endoscopic evaluations) are eligible to enter the LTE to receive approximately 2 additional years of treatment, during which time the longer-term efficacy and safety of guselkumab will be evaluated. All participants will be assessed. The final efficacy and safety follow-up (FES) visit of the LTE will occur at approximately Week 156 (i.e., approximately 16 weeks after their last study intervention administration at Week 140).

Participants who are not eligible to enter the LTE at Week 48 are to return for a FES visit 16 weeks after their last study intervention administration.

During the LTE, all participants will continue to receive the same treatment regimen (ie, guselkumab, ustekinumab, or placebo) that they were receiving at the end of GALAXI 1, GALAXI 2, or GALAXI 3. The first study intervention administration in the LTE will occur at Week 48 and the last study intervention administration will occur at Week 140. Treatment adjustment for inadequate response is permitted between Week 52 and Week 80 of the LTE.

Beginning at Week 48, at the discretion of the investigator and participant, and after appropriate and documented training, participants may self-administer study intervention at the investigative site. A caregiver may also be trained to administer study intervention. After receiving training at Week 48, participants who are eligible for self-(or caregiver) administration of study intervention will be supplied with study intervention for at-home administration and will have their first at-home administration at Week 52. Participants who are unable or unwilling to have study intervention administered away from the investigative site will continue administration at the investigative site.

All participants will continue to receive active or placebo study intervention administration in the LTE in a blinded fashion until study unblinding, which will occur after the Week 48 DBL and the Week 48 analyses have been completed for the Phase 2 study (for participants entering the LTE from GALAXI 1) or for the Phase 3 studies (for participants entering the LTE from GALAXI 2 or GALAXI 3).

After study unblinding, all participants who are on active treatment (i.e., guselkumab or ustekinumab) will continue to receive their assigned active treatment for the remaining duration of the LTE through Week 140. Participants who are on placebo will be discontinued from study intervention upon study unblinding, and will have an FES visit at that time.

Treatment Adjustment for Inadequate Response

Participants from all treatment groups (i.e., guselkumab, ustekinumab, and placebo) who meet inadequate response criteria between Week 52 (i.e., the first visit at which treatment adjustment is permitted) and Week 80 (i.e., the last visit at which treatment adjustment is permitted) will be eligible for a single treatment adjustment (i.e., the first-time inadequate response criteria are met).

Inadequate response is defined as not being in clinical response AND having a CDAI score of at least 220 points. Clinical response is defined as a reduction from baseline (ie, Week 0) in the CDAI score of ≥100 points or being in clinical remission (CDAI<150).

Participants (who are receiving placebo, ustekinumab, or the lower SC maintenance dose of guselkumab) will be eligible to receive a single, blinded, treatment adjustment to the highest guselkumab SC maintenance dose as defined in the Phase 2 or the Phase 3 portion of the protocol in which they are enrolled. Participants who are already receiving the highest guselkumab SC maintenance dose will receive a single, blinded, sham treatment adjustment. Participants who have received treatment adjustments will remain on their new treatment regimen through Week 92.

At Week 96, the benefit of treatment adjustment will be evaluated. Continued participation in the remaining duration of the LTE will be decided on investigator's clinical judgment of the results of the Week 96 clinical and endoscopic evaluations. Discontinuation of study intervention should be considered in participants with persistent unsatisfactory response or clinically significant worsening Crohn's disease where continuation of the study intervention is not in the best interest of the participant.

Endpoints and Evaluations

Through Week 156, the longer-term efficacy and safety of guselkumab will be evaluated. In addition, the benefit of treatment adjustment will be evaluated based on descriptive analysis of various efficacy endpoints (to be specified in the SAP).

Database locks are planned at Week 96 and when the final participant has completed the final efficacy and safety visit in the LTE. Additional DBLs may be added if necessary, and will be specified in the Phase 3 SAP.

Use of Placebo- and Active-Control

The inclusion of both placebo and active controls in the same protocol has several advantages. A short-term placebo-control period facilitates the evaluation of the short-term efficacy and safety of a new treatment compared with placebo within a timeframe for which the use of placebo in participants with active disease is considered clinically acceptable in support of scientific research. For longer-term treatment, the use of an active comparator control can alleviate the concern over the extended use of placebo and can also provide an opportunity to evaluate comparative efficacy and safety in a randomized-controlled setting. There is significant clinical value to determine whether a new treatment option will provide similar or greater benefit to patients compared with an approved treatment option.

Ustekinumab was selected as the active comparator because it targets an overlapping mechanism of action (i.e., both IL-12/23 blockade) and the preclinical evidence suggests the potential for improved efficacy with more specific targeting of IL-23. Further, the proposed dosing of ustekinumab in this protocol is the highest currently approved induction-maintenance dose regimen and was one of the dose regimens evaluated in the ustekinumab Phase 3 clinical development program in Crohn's disease. Therefore, the inclusion of ustekinumab as an active comparator in this program will provide a valuable and relevant benchmark for comparison with guselkumab.

Ustekinumab is included as an active-reference arm in the Phase 2 study to collect data that will inform treatment effect size and sample size assumptions for the Phase 3 studies. Ustekinumab is included in the 2 Phase 3 studies as an active comparator control arm to enable the randomized-controlled evaluation of the long-term efficacy and safety of the 2 guselkumab dose regimens compared with ustekinumab through approximately 1 year (i.e., Week 48) of treatment. An important objective of this development program is to determine whether the efficacy of guselkumab is superior (or, at minimum, non-inferior) to ustekinumab in achieving long-term clinical remission.

Patient-Reported Outcomes on Health-Related Quality of Life

Patient-reported outcome (PRO) evaluations (ie, IBDQ, PROMIS-29, PROMIS Fatigue 7-item Short Form, 5-level EuroQol 5 dimensions [EQ-5D-5L] instrument) will be used to assess the benefits of guselkumab treatment on disease-specific and general HRQOL.

Phase 2 Dose-Ranging Study (GALAXI 1)

The following guselkumab dose regimens will be evaluated through Week 48 of GALAXI 1:

Guselkumab Regimen 1—Induction: 1200 mg IV at Weeks 0, 4, 8; followed by Maintenance: 200 mg SC q4w (ie, at Weeks 12, 16, 20, 24, 28, 32, 36, 40, and 44)

Guselkumab Regimen 2—Induction: 600 mg IV at Weeks 0, 4, 8; followed by Maintenance: 200 mg SC q4w (ie, at Weeks 12, 16, 20, 24, 28, 32, 36, 40, and 44)

Guselkumab Regimen 3—Induction: 200 mg IV at Weeks 0, 4, 8; followed by Maintenance: 100 mg SC q8w (ie, at Weeks 16, 24, 32, and 40)

Induction Dose Regimens

Cross-study comparisons between the guselkumab and risankizumab Phase 2 studies in patients with plaque psoriasis suggest that comparable efficacy was attained at almost similar dose regimens. A model-based meta-analysis also suggests comparable clinical potency for these 2 compounds. In addition, the PK of guselkumab were found to be similar to those of risankizumab.13,23 These dose-response and PK data suggest that comparable levels of IL-23 blockade and efficacy may be achieved in Crohn's disease at similar dose regimens or systemic exposures for these 2 compounds. Furthermore, a PK/PD model of ustekinumab (an IL-12/23 blocker), which is approved in Crohn's disease was considered applicable to predict efficacy following administration of different guselkumab dose regimens.

In the Phase 2 study of risankizumab in participants with moderately to severely active Crohn's disease, dose-dependent efficacy was demonstrated with a greater proportion of participants on the higher induction dose regimen of risankizumab (ie, 600 mg IV q4w) achieving remission at Week 12 compared with those receiving the lower dose regimen (ie, 200 mg IV q4w); however, it was not clear if maximum efficacy was attained with the risankizumab 600 mg IV induction dose regimen in this Phase 2 study. Dose-dependent efficacy was further demonstrated with risankizumab as shown by an increased rate of remission in patients who switched from 200 mg IV to 600 mg IV in the second period of that study (Week 12 through Week 26). Based on these findings, along with the comparable PK and clinical potency of guselkumab and risankizumab, and coupled with the PK/PD predictions of guselkumab in Crohn' disease, induction dose regimens comprising guselkumab 600 mg IV, and 200 mg IV, each given at Weeks 0, 4, and 8, were selected for the Phase 2 dose-ranging study.

Additionally, a higher dose of guselkumab (1200 mg q4w IV) induction dose regimen will evaluate the possibility of achieving a higher level of efficacy at Week 12 than that observed with the higher risankizumab dose regimen (ie, 600 mg IV) tested in Phase 2. Overall, the 3 guselkumab IV induction dose regimens provide a 6-fold range of exposure that is likely to result in adequate separation between dose levels and consequently support guselkumab induction dose selection for Phase 3.

Regarding the safety of these higher IV induction guselkumab doses, single doses of guselkumab as high as 10 mg/kg, with the highest single dose tested being 987 mg, have been previously studied in a Phase 1 plaque psoriasis study in a limited number of participants. Additionally, guselkumab IV doses of up to 50 mg/kg weekly for 5 weeks, and guselkumab SC doses of up to 50 mg/kg weekly for 24 weeks, were well-tolerated in cynomolgus monkeys and did not result in any clinical or anatomic findings. These data suggest an acceptable exposure margin between predicted guselkumab exposures for the 1200 mg IV regimen compared with those observed in toxicology studies. Furthermore, risankizumab was well-tolerated at dose regimens up to 6 doses of 600 mg IV q4w, ie, a total of 3600 mg over a period of 26 weeks. Longer-term follow-up of these participants through Week 52 did not identify any significant safety concerns based on published data. Nonetheless, an external DMC will be commissioned to monitor the benefit-risk of guselkumab.

Maintenance Dose Regimens

The posology of other biologics in Crohn's disease suggests that once the inflammatory burden of the disease is reduced, the drug exposures required to maintain efficacy may be lower than the exposures attained with initial induction doses.

In the ustekinumab Crohn's disease Phase 3 studies, among participants who were in remission at Week 8 following an induction regimen of ~6 mg/kg IV, a 90 mg SC q8w maintenance regimen resulted in 67% of subjects maintaining remission at Week 52. In the risankizumab Crohn's disease Phase 2 study, among participants who were in remission at Week 26 after receiving up to 6 months of 600 mg IV q4w induction dosing, the long-term uncontrolled data showed that a 180 mg SC q8w regimen resulted in 71% of patients maintaining remission at Week 52.

Accordingly, in this protocol, after 12 weeks of guselkumab IV induction treatment, dose regimens providing lower guselkumab exposures will be evaluated during SC maintenance treatment through Week 48. The selected maintenance dose regimens provide reasonable maintenance: induction exposure ratios comparable to those of other biologics approved in Crohn's disease.

Regimens 1 and 2 evaluate guselkumab 1200 mg IV q4w and 600 mg IV q4w induction, respectively. For each of these regimens, a maintenance regimen of 200 mg SC q4w will be studied to evaluate if higher exposure than that tested in the risankizumab Phase 2 study (i.e., 180 mg SC q8w) is necessary to optimize efficacy in maintenance.

For Regimen 3, which evaluates guselkumab 200 mg IV q4w induction, a maintenance regimen of 100 mg SC q8w will be studied. The guselkumab 100 mg SC q8w regimen is expected to provide efficacy at least similar to, or greater than that observed with ustekinumab 90 mg SC q8w, the maintenance dose regimen for the active comparator being evaluated in this study.

Overall, the 2 guselkumab maintenance SC dose regimens provide a 4-fold range of exposure that should support dose selection for Phase 3.

No treatment adjustments are planned for any of the treatment groups from Week 0 through Week 48 of GALAXI 1, except for IV induction placebo nonresponders who will cross over to receive the ustekinumab dose regimen being evaluated in this study (i.e., ~6 mg/kg IV at Week 12 followed by 90 mg SC q8w from Week 20). Participants randomized to placebo IV who are responders at Week 12 will continue to receive SC placebo through Week 44.

Phase 3 Dose-Confirming Studies (GALAXI 2 and GALAXI 3)

Based on the Phase 2 data, 2 guselkumab dose regimens (ie, IV induction→SC maintenance) will be selected for confirmatory evaluation in Phase 3.

The goal is to select a single induction dose regimen from the induction dose range evaluated (ie, 200 mg to 1200 mg IV q4w at Week 0, Week 4, and Week 8) in the Phase 2 dose-ranging study based on the totality of the efficacy, safety, and exposure-response (E-R) data at the time of dose decision. The choice of a single induction regimen to be evaluated in the Phase 3 dose-confirming studies is based on the consideration that a sufficient amount of information will be available to establish an optimal induction dose regimen. In this scenario, the selected induction dose regimen will be paired with 2 maintenance dose regimens selected from the range of exposures obtained from the guselkumab SC dose regimens evaluated in Phase 2 (i.e., between 100 mg q8w to 200 mg q4w).

It is also possible that the Phase 2 data may support the selection of more than one induction dose regimen for Phase 3 evaluation. In this case, each selected induction dose regimen will be paired with an appropriate maintenance dose regimen.

No treatment adjustments are planned for any of the treatment groups from Week 0 through Week 48 of GALAXI 2 and GALAXI 3, except for IV induction placebo nonresponders who will cross over to receive the ustekinumab dose regimen being evaluated in this study (ie, ~6 mg/kg IV at Week 12 followed by 90 mg SC q8w from Week 20). Participants randomized to placebo IV who are responders at Week 12 will continue to receive SC placebo through Week 44.

Long Term Extension (Week 48 to Week 144)

Participants will continue on their assigned guselkumab maintenance dose during the LTE of GALAXI 1, GALAXI 2, and GALAXI 3. Participants who experience inadequate response between Week 52 through Week 80 while on the lower of the 2 maintenance dose regimens being evaluated in the respective study will be eligible for a single dose adjustment, and will receive the higher maintenance dose until the end of the LTE to assess if they can regain clinical response.

Inclusion Criteria

Each potential participant must satisfy all of the following criteria to be enrolled in the protocol:

1. Be male or female (according to their reproductive organs and functions assigned by chromosomal complement) ≥18 years of age.
2. Have Crohn's disease or fistulizing Crohn's disease of at least 3 months duration (defined as a minimum of 12 weeks), with colitis, ileitis, or ileocolitis, confirmed at any time in the past by radiography, histology, and/or endoscopy.
3. Have clinically active Crohn's disease, defined as a baseline CDAI score ≥220 but ≤450 and either:
   a. Mean daily SF count >3, based on the unweighted CDAI component of the number of liquid or very soft stools
   OR
   b. Mean daily AP score >1, based on the unweighted CDAI component of abdominal pain
4. Have endoscopic evidence of active ileocolonic Crohn's disease as assessed by central endoscopy reading at the screening endoscopy, defined as a screening SES-CD score ≥3, which indicates the presence of at least 1 large ulcer (in the ileum, colon, or both) that results in:
a. a minimum score of 2 for the component of "size of ulcers"
AND
b. a minimum score of 1 for the component of "ulcerated surface".

Within each of the studies, a maximum of 10% of the total enrolled population will be participants who have baseline scores for SES-CD<4 (i.e., for participants with isolated ileal disease) or SES-CD<7 (i.e., for participants with colonic or ileocolonic disease).

Concomitant or Previous Medical Therapies Received

5. Prior or current medication for Crohn's disease must include at least 1 of the following, and must fulfill additional criteria as described in Appendix 2 (Section 10.2), Appendix 3 (Section 10.3), and Appendix 4 (Section 10.4):
   a. Current treatment with oral corticosteroids (including budesonide and beclomethasone dipropionate) and/or immunomodulators (AZA, 6-MP, MTX)
   OR
   b. History of failure to respond to, or tolerate, at least 1 of the following therapies: oral corticosteroids (including budesonide and beclomethasone dipropionate) or immunomodulators (AZA, 6-MP, MTX).
   OR
   c. History of corticosteroid dependence (ie, an inability to successfully taper corticosteroids without a return of the symptoms of Crohn's disease).
   OR
   d. Has previously demonstrated lack of initial response (ie, primary nonresponders), responded initially but then lost response with continued therapy (i.e., secondary nonresponders), or were intolerant to 1 or more biologic agents at a dose approved for the treatment of Crohn's disease (ie, infliximab, adalimumab, certolizumab pegol, vedolizumab, or approved biosimilars for these agents).
   Note: Participants meeting criteria 5a-c may also be naïve to biologic therapy (i.e., a TNF antagonist or vedolizumab or ustekinumab) or may have been exposed to these biologic therapies but have not demonstrated inadequate response or intolerance. Participants with prior exposure to IL-12/23 or IL-23 agents are ineligible for entry into this protocol, with the exception of participants who have had limited exposure to ustekinumab at its approved labeled dosage AND have met the required wash-out criterion AND have not demonstrated failure or intolerance to ustekinumab.

6. Adhere to the following requirements for concomitant medication for the treatment of Crohn's disease. The following medications are permitted provided that doses meeting the requirements listed below are stable or have been discontinued prior to baseline within the timeframes specified below:
   a. Oral 5-aminosalicylic acid (5-ASA) compounds on stable doses for at least 2 weeks; or if recently discontinued, must have been stopped for at least 2 weeks.
   b. Oral corticosteroids at a prednisone-equivalent dose at or below 40 mg/day, or 9 mg/day of budesonide, or 5 mg/day beclomethasone dipropionate, and on stable dosing for at least 2 weeks; or if recently discontinued, must have been stopped for at least 2 weeks.
   c. Conventional immunomodulators (i.e., AZA, 6-MP, or MTX) for at least 12 weeks and have been on a stable dose for at least 4 weeks; or if recently discontinued, must have been stopped for at least 4 weeks.
   d. If receiving antibiotics as a primary treatment of Crohn's disease, doses must be stable for at least 3 weeks; or if recently discontinued, must have been stopped for at least 3 weeks.
   e. If receiving enteral nutrition as a primary treatment for Crohn's disease, must have been receiving for at least 2 weeks; or if recently discontinued, must have been stopped for at least 2 weeks.

Screening Laboratory Tests

7. Have screening laboratory test results within the following parameters, and if 1 or more of the laboratory parameters is out of range, a single retest of laboratory values is permitted during the approximately 5-week screening period:
   a. Hemoglobin ≥8.0 g/dL.
   b. White blood cells (WBCs) ≥3.5×10³/μL.
   c. Neutrophils ≥1.5×10³/μL.
   d. Platelets ≥100×10³/μL.
   e. Serum creatinine ≤1.5 mg/dL.
   f. Aspartate aminotransferase (AST) and alanine aminotransferase (ALT) concentrations must be ≤2 times the upper limit of normal (ULN) range for the laboratory conducting the test.
   g. Direct (conjugated) bilirubin <1.0 mg/dL.

Tuberculosis

8. Are considered eligible according to the following tuberculosis (TB) screening criteria:
   a. Have no history of latent or active TB prior to screening. An exception is made for participants who have a history of latent TB AND who satisfy one of the following criteria:
      currently receiving treatment for latent TB
      will initiate treatment for latent TB prior to or simultaneously with the first administration of study intervention
      OR
      have documentation of having completed appropriate treatment for latent TB within 5 years prior to the first administration of study intervention. It is the responsibility of the investigator to verify the adequacy of previous anti-tuberculous treatment and provide appropriate documentation.
   b. Have no signs or symptoms suggestive of active TB upon medical history and/or physical examination.
   c. Have had no recent close contact with a person with active TB or, if there has been such contact, will be referred to a physician specializing in TB to undergo additional evaluation and, if warranted, receive appropriate treatment for latent TB prior to or simultaneously with the first administration of study intervention.
   d. Within 8 weeks prior to the first administration of study intervention, have a negative QuantiFERON®-TB Gold test result, or have a newly identified positive QuantiFERON-TB Gold test in which active TB has been ruled out and for which appropriate treatment for latent TB has been initiated either prior to or simultaneously with the first study intervention administration.
   Note: A negative tuberculin skin test result is additionally required if the QuantiFERON-TB Gold test is not approved/registered in the country in which this protocol is being conducted. In Ukraine, while the QuantiFERON-TB gold test is not approved/registered, it is acceptable, and an additional tuberculin skin test is not required. The QuantiFERON-TB Gold test and the tuberculin skin test are not required at screening for participants with a history of latent TB, if active TB has been ruled out, and if appropriate treatment has been initiated/completed as described above in Inclusion Criterion 8a.
  e. Have a chest radiograph (both posterior-anterior and lateral views, or per country regulations where applicable), taken ≤12 weeks before the first administration of study intervention and read by a qualified radiologist, with no evidence of current, active TB or old, inactive TB.

Contraception

Contraceptive (birth control) use by men or women should be consistent with local regulations regarding the acceptable methods of contraception for those participating in clinical studies. Typical use failure rates may differ from those when used consistently and correctly. Use should be consistent with local regulations regarding the use of contraceptive methods for participants in clinical studies.
  9. A female participant of childbearing potential must have a negative urine pregnancy test result at screening and baseline.
  10. Before randomization, a female participant must be:
  a. Not of childbearing potential
  b. Of childbearing potential and:
  c. Practicing a highly effective method of contraception (failure rate of <1% per year when used consistently and correctly) and agrees to remain on a highly effective method while receiving study intervention and until 16 weeks after last dose (ie, the end of relevant systemic exposure); however, the method selected must meet local/regional regulations/guidelines for highly effective contraception.
  Note: If a participant's childbearing potential changes after start of the study (e.g., a premenarchal woman experiences menarche) or the risk of pregnancy changes (e.g., a woman who is not heterosexually active becomes active), a woman must begin using a highly effective method of contraception, as described throughout the inclusion and exclusion criteria.
  11. A woman must agree not to donate eggs (ova, oocytes) for the purposes of assisted reproduction during the study and for a period of 16 weeks after the last administration of study intervention.
  12. During the study and for at least 16 weeks after the last administration of study intervention, a male participant
  a. who is sexually active with a female of childbearing potential must agree to use a barrier method of contraception (eg, condom with spermicidal foam/gel/film/cream/suppository).
  b. who is sexually active with a pregnant female must use a condom.
  c. must agree not to donate sperm for the purpose of reproduction.

General
  13. Be willing and able to adhere to the lifestyle restrictions specified in this protocol.
  14. Must sign an informed consent form (ICF) indicating that he or she understands the purpose of, and procedures required for, the study and is willing to participate in the study.
  15. Must sign a separate ICF if he or she agrees to provide an optional DNA sample for research (where local regulations permit). Refusal to give consent for the optional DNA research sample does not exclude a participant from participation in the study.

5.2. Exclusion Criteria

Any potential participant who meets any of the following criteria will be excluded from participating in the protocol:
  1. Has complications of Crohn's disease, such as symptomatic strictures or stenoses, short gut syndrome, or any other manifestation, that might be anticipated to require surgery, could preclude the use of the CDAI to assess response to therapy, or would possibly confound the ability to assess the effect of treatment with guselkumab or ustekinumab.
  2. Currently has or is suspected to have an abscess. Recent cutaneous and perianal abscesses are not exclusionary if drained and adequately treated at least 3 weeks before baseline, or 8 weeks before baseline for intra-abdominal abscesses, provided that there is no anticipated need for any further surgery. Participants with active fistulas may be included if there is no anticipation of a need for surgery and no abscesses are currently identified.
  3. Has had any kind of bowel resection within 6 months, or any other intra-abdominal or other major surgery (eg, requiring general anesthesia) within 12 weeks, before baseline.
  4. Has a draining (ie, functioning) stoma or ostomy.
  5. Has a stool culture or other examination positive for an enteric pathogen, including *Clostridium difficile* toxin, in the previous 4 months, unless a repeat examination is negative and there are no signs of ongoing infection with that pathogen.

Concomitant or Previous Medical Therapies Received
  6. Has received any of the following prescribed medications or therapies within the specified period:
  a. IV corticosteroids received within 3 weeks of baseline
  b. Cyclosporine, tacrolimus, sirolimus, or mycophenolate mofetil received within 8 weeks of baseline
  c. 6-thioguanine (6-TG) received within 4 weeks of baseline
  d. Biologic agents:
  1) Anti-TNF therapy (eg, infliximab, etanercept, certolizumab pegol, adalimumab, golimumab) received within 8 weeks of baseline
  2) Vedolizumab received within 16 weeks of baseline
  3) Ustekinumab received within 16 weeks of baseline
  4) Other immunomodulatory biologic agents received within 12 weeks of baseline or within 5 half-lives of baseline, whichever is longer.
  e. Any investigational intervention received within 4 weeks of baseline or within 5 half-lives of baseline, whichever is longer.
  f. Nonautologous stem cell therapy (eg, Prochymal), natalizumab, efalizumab, or biologic agents that deplete B- or T-cells (eg, rituximab, alemtuzumab, or visilizumab) received within 12 months of baseline.
  g. Treatment with apheresis (eg, Adacolumn apheresis) or total parenteral nutrition for Crohn's disease within 3 weeks of baseline.
  7. Has previously received a biologic agent targeting IL-12/23 or IL-23, including but not limited to briakinumab, brazikumab, guselkumab, mirakizumab (formerly LY2525623), and risankizumab.
  Exception: Participants who have had limited exposure to ustekinumab at its approved labeled dosage AND have met the required wash-out criterion AND have not demonstrated failure or intolerance to ustekinumab are not excluded from this protocol provided that other inclusion criteria have been satisfied and no other exclusion criteria are met.

Infections or Predisposition to Infections:
8. Has a history of, or ongoing, chronic or recurrent infectious disease, including but not limited to, chronic renal infection, chronic chest infection (e.g., bronchiectasis), recurrent urinary tract infection (e.g., recurrent pyelonephritis or chronic nonremitting cystitis), or open, draining, or infected skin wounds or ulcers.
9. Has current signs or symptoms of a clinically significant infection. Established non-serious infections (e.g., acute upper respiratory tract infection, simple urinary tract infection) need not be considered exclusionary at the discretion of the investigator.
10. Has a history of serious infection (e.g., hepatitis, sepsis, pneumonia, or pyelonephritis), including any infection requiring hospitalization or IV antibiotics, for 8 weeks before baseline.
11. Has evidence of a herpes zoster infection within 8 weeks before baseline.
12. Has a history of latent or active granulomatous infection, including histoplasmosis or coccidioidomycosis, prior to screening. Participants with radiographic evidence of possible prior histoplasmosis or coccidioidomycosis will be excluded.
13. Has a chest radiograph within 12 weeks prior to the first administration of study intervention that shows an abnormality suggestive of a malignancy or current active infection, including TB.
14. Has or has had a nontuberculous mycobacterial infection or clinically significant opportunistic infection (e.g., cytomegalovirus colitis, pneumocystosis, invasive aspergillosis).
15. Participants must undergo screening for human immunodeficiency virus (HIV). Any participant who has a history of HIV antibody positivity, or tests positive for HIV at screening, is not eligible for this study.
16. Participants who are seropositive for antibodies to hepatitis C virus (HCV), unless they have 2 negative HCV RNA test results at least 6 months apart after completing antiviral treatment and prior to screening, and have a third negative HCV RNA test result at screening.
17. Tests positive for hepatitis B virus (HBV) infection.
Note: For participants who are not eligible for this study due to HIV, HCV, HBV, or TB test results, consultation with a physician with expertise in the treatment of those infections is recommended.
18. Has received, or is expected to receive, any live virus or bacterial vaccination within 12 weeks before the first administration of study intervention. For Bacille Calmette-Guerin (BCG) vaccine, see Exclusion Criterion 14.
19. Has had a BCG vaccination within 12 months of screening.

Malignancy or Increased Potential for Malignancy
20. Currently has a malignancy or has a history of malignancy within 5 years before screening (with the exception of a nonmelanoma skin cancer that has been adequately treated with no evidence of recurrence for at least 3 months [defined as a minimum of 12 weeks] before the first study intervention administration or cervical carcinoma in situ that has been treated with no evidence of recurrence for at least 3 months before the first study intervention administration).
21. Has a known history of lymphoproliferative disease, including monoclonal gammopathy of unknown significance, lymphoma, or signs and symptoms suggestive of possible lymphoproliferative disease, such as lymphadenopathy, hepatomegaly, or splenomegaly, or monoclonal gammopathy of undetermined significance.

Coexisting Medical Conditions or Past Medical History
22. Has a history of severe, progressive, or uncontrolled renal, genitourinary, hepatic, hematologic, endocrine, cardiac, vascular, pulmonary, rheumatologic, neurologic, psychiatric, or metabolic disturbances, or signs and symptoms thereof.
23. Has a transplanted organ (with exception of a corneal transplant >12 weeks before screening).
24. Is unable or unwilling to undergo multiple venipunctures because of poor tolerability or lack of adequate venous access.
25. Is known to have had a history of drug or alcohol abuse according to Diagnostic and Statistical Manual of Disorders ($5^{th}$ edition) (DSM-V) criteria within 12 months before baseline.
26. Has unstable suicidal ideation or suicidal behavior in the last 6 months that may be defined as a Columbia-Suicide Severity Rating Scale (C-SSRS) rating at screening of: Suicidal Ideation with Intention to Act ("Ideation level 4"), Suicidal Ideation with Specific Plan and Intent ("Ideation level 5"), or suicidal behavior (actual suicide attempt, interrupted suicide attempt, aborted suicide attempt, or preparatory behaviors for making a suicide attempt), and is considered to be at risk by the investigator based on an evaluation by a mental health professional. In addition, participants with C-SSRS ratings of Wish to be Dead ("Ideation level 1"), Non-Specific Active Suicidal Thoughts ("Ideation level 2"), Active Suicidal Ideation with Any Methods (Not Plan) without Intent to Act ("Ideation level 3") or non-suicidal self-injurious behavior who are determined to be at risk by the investigator may not be randomized.
27. Has known allergies, hypersensitivity, or intolerance to guselkumab or ustekinumab or any of their excipients (see guselkumab IB and ustekinumab IB).
28. Is a woman who is pregnant, or breastfeeding, or planning to become pregnant while enrolled in this study or within 16 weeks after the last administration of study intervention.
29. Is a man who plans to father a child while enrolled in this study or within 16 weeks after the last administration of study intervention.

General
30. Is currently enrolled in or intends to participate in any other study using an investigational agent or procedure during participation in this study.
31. Has any condition for which, in the opinion of the investigator, participation would not be in the best interest of the participant (eg, compromise the well-being) or that could prevent, limit, or confound the protocol-specified assessments.
32. Is an employee of the investigator or study site, with direct involvement in the proposed study or other studies under the direction of that investigator or study site, as well as family members of the employees or the investigator.
NOTE: Investigators should ensure that all study enrollment criteria have been met at screening. If a participant's clinical status changes (including any available laboratory results or receipt of additional medical records) after screening but before the first dose of study intervention is given such that he or she no longer meets all eligibility criteria, then the participant should be excluded from participation in the study.

Study Interventions Administered

In both the Phase 2 and Phase 3 portions of the protocol:
All participants will receive 2 IV infusions at Week 0 (either active or placebo) and 1 IV infusion at Weeks 4, 8, and 12 (either active or placebo).

All participants will receive 1 SC injection (either active or placebo) at Week 8 and up to 3 SC injections (either active or placebo) at each visit from Week 12 to Week 140.

Intravenous study intervention should be administered over a period of not less than 1 hour, and not more than 2 hours. The infusion should be completed within 6 hours of preparation. Since multiple SC injections may be administered within the administration visit, each injection of study intervention should be given at a different location of the body.

Concomitant Medications

Participants who are receiving oral 5-ASA compounds, oral corticosteroids, conventional immunomodulators (ie, AZA, 6-MP, or MTX), antibiotics, and/or enteral nutrition for the treatment of Crohn's disease at baseline should maintain a stable dose for the specified period before baseline, as defined in the Inclusion Criteria.

In general, participants who are receiving these medications for Crohn's disease at baseline (i.e., Week 0) of all 3 studies should maintain a stable dose through Week 48, with the exception of oral corticosteroids. Therapies can only be discontinued or reduced in dose after Week 0 if investigator judgment requires it because of toxicity or other medical necessity; even if the toxicity resolves, the therapy should not be restarted. Corticosteroids must be maintained at baseline doses through Week 12, and all participants must begin tapering corticosteroids at Week 12, unless medically not feasible.

Week 0 Through Week 48

From Week 0 through Week 48 of each study, enrolled participants should not initiate any of the following concomitant Crohn's disease-specific medical therapies:
Oral or rectal 5-ASA compounds.
Immunomodulators (ie, AZA, 6-MP, or MTX).
Oral, parenteral, or rectal corticosteroids, including budesonide and beclomethasone dipropionate.
Antibiotics as a primary treatment for Crohn's disease.
Total parenteral nutrition or enteral nutrition as a treatment for Crohn's disease.

If the above medical therapies are initiated or medication doses are changed based on medical necessity as assessed by the investigator, participants should continue to attend all study visits and have all assessments. While this does not represent a deviation from the study protocol and the participants may remain on their assigned therapy (guselkumab, ustekinumab, or placebo), it may be considered a treatment failure. Treatment failures will be defined in the SAP.

Week 12 and Through Week 48

From Week 12 through Week 48 of each study, participants may transiently use (i.e., for <4 weeks) increased doses of corticosteroids for reasons other than loss of response to treatment for Crohn's disease (eg, stress doses of corticosteroids for surgery, asthma, adrenocortical insufficiency).

During Treatment Phase of LTE (Ie, Week 48 Through Week 144):
Concomitant therapies for Crohn's disease including 5-ASAs, corticosteroids, antibiotics, and immunomodulators (ie, AZA, 6-MP, or MTX), and/or total parental or enteral nutrition may be administered and changed at the discretion of the investigator.

Oral Corticosteroids Tapering

At Week 12, all participants who were taking corticosteroids at Week 0 must begin tapering corticosteroids. This tapering is mandatory, unless not medically feasible, and should follow the recommended schedule shown in Table 6. If participants experience worsening of their disease activity while tapering corticosteroids, further dose decreases may be suspended, and/or their oral corticosteroid dose may be temporarily increased if deemed necessary by the investigator. The oral corticosteroid dose, however, may not be increased above the Week 0 dose unless due to medical necessity. For participants whose corticosteroid taper is interrupted, investigators are encouraged to resume tapering within 4 weeks. Tapering may exceed this schedule only if warranted by medical necessity (eg, participant experiencing corticosteroid-related side effects).

Prohibited Concomitant Medications

Participants who initiate the following treatments during study participation will have their study intervention discontinued:
Immunomodulatory agents other than AZA, 6-MP, or MTX (including, but not limited to, 6-TG, cyclosporine, mycophenolate mofetil, tacrolimus, and sirolimus).
Immunomodulatory biologic agents (including, but not limited to, TNF antagonists, natalizumab, ustekinumab, rituximab, vedolizumab). Ustekinumab is permitted in this study only in participants randomly assigned to ustekinumab and only as stipulated in this protocol.
Experimental Crohn's disease medications (including, but not limited to, upadacitinib, filgotinib, ozanimod, etrolizumab, brazikumab, mirakizumab [formerly LY-3074828], risankizumab, GS-5745).
Thalidomide or related agents.

Efficacy Assessments

Efficacy evaluations will include the following:
CDAI
PRO-2 (the unweighted CDAI components of the total number of liquid or very soft stools and the abdominal pain score)
Endoscopic assessments of the intestinal mucosa based on the presence and absence of mucosal ulcerations and the SES-CD, and histologic assessments based on the Global Histology Activity Score (GHAS)
Inflammatory PD markers including CRP and fecal calprotectin
Fistula assessment
Patient-reported outcome (PRO) measures to assess HRQOL outcomes (ie, IBDQ, PROMIS-29, and PROMIS Fatigue 7-item Short Form [7a], and EQ-5D-5L), and health economics outcomes (ie, WPAI-CD)
Exploratory patient-reported symptom measures including BSFS, AP-NRS, Patient's Global Impression of Severity (PGIS) of Crohn's Disease, and Patient's Global Impression of Change (PGIC) of Severity of Crohn's Disease The CDAI be assessed by collecting information on 8 different Crohn's disease-related variables: extra-intestinal manifestations, abdominal mass, weight, hematocrit, total number of liquid or very soft stools, abdominal pain/cramping, use of antidiarrheal drug(s) and/or opiates, and general well-being. The last 4 variables are scored over 7 days by the participant on a diary card that participants are to complete on a daily basis. The PRO-2 includes the unweighted CDAI components of the total number of liquid or very soft stools and the AP score.

Endoscopic assessments of the intestinal mucosa will be evaluated during ileocolonoscopy in all participants. A video ileocolonoscopic examination will be performed at Screening, Week 12, Week 48, and Week 96. An optional sub-study involving a Week 4 evaluation will be performed in consenting participants in addition to the above specified evaluations. Video endoscopies will be assessed by a central facility that will be blinded to treatment group and visit. A complete video endoscopic examination does not require assessment of the terminal ileum if it cannot be visualized. The SES-CD score will be used to evaluate Endoscopic Improvement. The SES-CD is based on the evaluation of 4 endoscopic components (presence/size of ulcers, proportion of mucosal surface covered by ulcers, proportion of mucosal surface affected by any other lesions, and presence/type of narrowing/strictures) across 5 ileocolonic segments. Each endoscopic component is scored from 0 to 3 for each segment, resulting in a total score of up to 15 for each component, except for the narrowing component which can only attain a maximum total score of 11 because by definition, the presence of a narrowing that cannot be passed can be only observed once. In summary, an overall total SES-CD score is derived from the sum of all the component scores and can range from 0 to 56). Endoscopic healing, which is traditionally defined as the resolution (absence) of mucosal ulcers in response to a therapeutic intervention, will also be assessed.

Histologic assessments will be performed using biopsy samples collected during ileocolonoscopy. Biopsy samples will be collected at screening, Week 12, Week 48, and Week 96 from each of 3 predefined anatomic locations: the terminal ileum, splenic flexure, and rectum. An optional sub-study involving a Week 4 evaluation will be performed in consenting participants in addition to the above-specified evaluations. The biopsy samples collected post-baseline will be obtained near where the screening biopsy samples were collected from each of the 3 predefined locations. Histologic assessments will be conducted by a central reader who is blinded to treatment groups and visit. The Global Histology Activity Score (GHAS) will be used to evaluate histologic improvements and healing.5 Analyses will be specified in the SAP.

Fistula assessment will be performed in all participants on an ongoing basis throughout the duration of the studies. All participants will be assessed for fistulas at baseline. For participants with fistulizing disease, fistula closure will be assessed during the studies. Enterocutaneous fistulas (eg, perianal and abdominal) will be considered no longer draining (ie, closed) when there is absence of drainage despite gentle compression. Rectovaginal fistulas will be considered closed based on either physical examination or absence of relevant symptoms (eg, passage of rectal material or flatus from the vagina).

Patient-reported outcome measures will be evaluated at visits as indicated in the Schedule of Activities (Section 1.3):

The IBDQ is a validated, 32-item, self-reported questionnaire for participants with IBD to evaluate PROs across 4 dimensions: bowel symptoms (loose stools, abdominal pain), systemic symptoms (fatigue, altered sleep pattern), social function (work attendance, need to cancel social events), and emotional function (anger, depression, irritability).11 Scores range from 32 to 224, with higher scores indicating better outcomes.

The PROMIS-29 is a validated general health profile instrument that is not disease-specific. It is a collection of short forms containing 4 items for each of 7 domains (depression, anxiety, physical function, pain interference, fatigue, sleep disturbance, and ability to participate in social roles and activities). PROMIS-29 also includes an overall average pain intensity 0-10 numeric rating scale (NRS).

The PROMIS Fatigue 7-items Short Form (PROMIS Fatigue Short Form 7a) contains 7 items evaluating fatigue-related symptoms (ie, tiredness, exhaustion, mental tiredness, and lack of energy) and associated impacts on daily activities (ie, activity limitations related to work, self-care, and exercise). PROMIS Fatigue Short Form 7a has a recall period of past 7 days. Compared to the fatigue scale of PROMIS-29, PROMIS Fatigue Short Form 7a provides additional information to evaluate severity of fatigue.

The EQ-5D-5L is a validated instrument consisting of the EuroQol five dimensions descriptive system (EQ-5D) and the EuroQol visual analog scale (EQ-VAS). The descriptive system comprises 5 dimensions (mobility, self-care, usual activities, pain/discomfort, anxiety/depression). Each dimension has 5 levels: no problems, slight problems, moderate problems, severe problems, and extreme problems. The respondent is asked to indicate his/her health state by checking the most appropriate statement in each of the 5 dimensions. The EQ-VAS records the respondent's self-rated health on a 20-cm vertical, visual analog scale with endpoints labeled 'the best health you can imagine' and 'the worst health you can imagine'. The respondents mark an "X" on the scale to indicate their health TODAY and then write the number marked on the scale in the box.

The WPAI-CD is a validated instrument created as a patient-reported quantitative assessment of the amount of absenteeism, presenteeism, and daily activity impairment attributable to Crohn's disease. The WPAI-CD consists of 6 questions to determine employment status, hours missed from work due to Crohn's disease, hours missed from work for other reasons, hours worked, the degree to which Crohn's disease affected work productivity while at work, and the degree to which Crohn's disease affected activities outside of work. Four scores are derived: percentage of absenteeism, percentage of presenteeism (reduced productivity while at work), an overall work impairment score that combines absenteeism and presenteeism, and percentage of impairment in activities performed outside of work. Higher scores indicate greater impairment.

Exploratory patient-reported symptom measures will be evaluated at visits as indicated in the Schedule of Activities:

The BSFS is a medical aid to classify the form (or consistency) of human feces into 7 categories.14 It has been used as a research tool to evaluate the effectiveness of treatments for various diseases of the bowel (eg, irritable bowel syndrome [IBS]). Participants will complete the BSFS as a daily diary entry from Week 0 through Week 48.

The AP-NRS is an 11-point (0-10) scale that will be used to evaluate abdominal pain. The score of 0 represents "no abdominal pain" and the score of 10 represents the "worst possible abdominal pain" with greater scores indicating greater pain severity and intensity. Participants will complete the AP-NRS as a daily diary entry from Week 0 through Week 48, selecting only one number that best reflects their pain at its worst.

PGIS of Crohn's Disease: Participants will rate their Crohn's disease activity at baseline and each visit using a 5-point scale ("None", "Mild", "Moderate", "Severe" and "Very Severe"). The PGIS will be used as an anchor to establish and or validate response criteria of other clinical endpoints.

PGIC of Severity of Crohn's Disease: Participants' perceived change (improvement or deterioration) in the severity of their Crohn's disease will be assessed using the PGIC. Participants will rate how their Crohn's disease has changed since the beginning of the study using a 7-point scale ranging from "a lot better now" to "a lot worse now" with a neutral center point ("neither better nor worse"). The PGIC will be used as an anchor to establish and or validate response criteria of other clinical endpoints.

Safety Assessments

Adverse events will be reported and followed by the investigator. Any clinically relevant changes occurring during the study must be recorded in the Adverse Event section of the eCRF. Any clinically significant abnormalities persisting at the end of the study/early withdrawal will be followed by the investigator until resolution or until a clinically stable endpoint is reached.

The study will include the following evaluations of safety and tolerability according to the time points specified:

Electrocardiogram

A 12-lead electrocardiogram (ECG) will be performed at screening.

During the collection of ECGs, participants should be in a quiet setting without distractions (eg, television, cell phones). Participants should rest in a supine position for at least 5 minutes before ECG collection and should refrain from talking or moving arms or legs. If blood sampling or vital sign measurement is scheduled for the same time point as ECG recording, the procedures should be performed in the following order: ECG(s), vital signs, blood draw.

Physical Examination

Physical examinations will be performed as specified in the Schedule of Activities. While assessment of the participants for safety and efficacy requires some physical examination by an investigator at all visits, a more complete, detailed physical exam will be performed at specified visits.

Height and Weight

Height and weight will be measured as specified in the Schedule of Activities. Subjects will be instructed to remove shoes and outdoor apparel and gear prior to these measurements.

Vital Signs

Vital signs (including temperature, pulse/heart rate, respiratory rate, and blood pressure) will be obtained before and approximately every 30 minutes during every IV infusion, and at approximately 30-minute intervals after completion of the final IV infusion. Vital signs should be obtained before and approximately 30 minutes after the final SC injection.

Infections

Study intervention administration should not be given to a participant with a clinically important, active infection. Investigators are required to evaluate participants for any signs or symptoms of infection at scheduled visits (see Schedule of Activities, Section 1.3). If a participant develops a serious infection, including but not limited to sepsis or pneumonia, discontinuation of study treatment (ie, no further study intervention administrations) must be considered.

Tuberculosis Evaluation(s)

Initial Tuberculosis Evaluation

Participants must undergo testing for TB and their medical history assessment must include specific questions about a history of TB or known occupational or other personal exposure to individuals with active TB. The participant should be asked about past testing for TB, including chest radiograph results and responses to tuberculin skin or other TB testing. Investigators have the option to use both the QuantiFERON-TB Gold test and the tuberculin skin test to screen for latent TB if they believe, based on their judgment, that the use of both tests is clinically indicated in order to evaluate a participant who has high risk of having latent TB. If either the QuantiFERON-TB Gold test or the tuberculin skin test is positive, the participant is considered to have latent TB infection for the purposes of eligibility for this study.

Participants with a negative QuantiFERON-TB Gold test result (and a negative tuberculin skin test result in countries in which the QuantiFERON-TB Gold test is not approved/registered or the tuberculin skin is mandated by local health authorities) are eligible to continue with pre-randomization procedures. Participants with a newly identified positive QuantiFERON-TB Gold (or tuberculin skin) test result must undergo an evaluation to rule out active TB and initiate appropriate treatment for latent TB. Appropriate treatment for latent TB is defined according to local country guidelines for immunocompromised patients. If no local country guidelines for immunocompromised patients exist, US guidelines must be followed, or the participant will be excluded from the study.

A participant whose first QuantiFERON-TB Gold test result is indeterminate should have the test repeated. In the event that the second QuantiFERON-TB Gold test result is also indeterminate, the participant may be enrolled without treatment for latent TB if active TB is ruled out, their chest radiograph shows no abnormality suggestive of TB (active or old, inactive TB) and the participant has no additional risk factors for TB as determined by the investigator. This determination must be promptly reported to the sponsor's or designee's medical monitor and recorded in the participant's source documents and initialed by the investigator.

Tuberculosis Evaluation

Early Detection of Active Tuberculosis

To aid in the early detection of TB reactivation or new TB infection during study participation, participants must be evaluated for signs and symptoms of active TB at scheduled visits or by telephone contact approximately every 8 to 12 weeks. The following series of questions is suggested for use during the evaluation:

"Have you had a new cough of >14 days' duration or a change in a chronic cough?"

"Have you had any of the following symptoms:

Persistent fever?

Unintentional weight loss?

Night sweats?"

"Have you had close contact with an individual with active TB?" (If there is uncertainty as to whether a contact should be considered "close," a physician specializing in TB should be consulted.)

If the evaluation raises suspicion that a participant may have TB reactivation or new TB infection, an immediate and thorough investigation should be undertaken, including, where possible, consultation with a physician specializing in TB. Investigators should be aware that TB reactivation in immunocompromised participants may present as disseminated disease or with extrapulmonary features. Participants with evidence of active TB should be referred for appropriate treatment. Participants who experience close contact with an individual with active TB during the conduct of the study must have a repeat chest radiograph, a repeat QuantiFERON TB Gold test, a repeat tuberculin skin test in countries in which the QuantiFERON-TB Gold test is not approved/registered or the tuberculin skin test is mandated by local health authorities, and, if possible, referral to a physician specializing in TB to determine the participant's risk of developing active TB and whether treatment for latent TB is warranted.

Study intervention administration should be interrupted during the investigation. A positive QuantiFERON-TB Gold test or tuberculin skin test result should be considered detection of latent TB. If the QuantiFERON-TB Gold test result is indeterminate, the test should be repeated as outlined in Appendix 5 (Section 10.5). Participants should be encouraged to return for all subsequent scheduled study visits according to the protocol. Subjects who discontinue treatment for latent TB prematurely or who are noncompliant with therapy must immediately discontinue further administration of study intervention and be encouraged to return for all subsequent scheduled study visits according to the Schedule of Activities (Section 1.3).

Allergic Reaction

Before any SC injection or IV infusion, appropriately trained personnel and medications must be available to treat allergic reactions, including anaphylaxis. All participants must be observed carefully for symptoms of an allergic reaction (eg, urticaria, itching, hives). If a mild or moderate allergic reaction is observed, acetaminophen, nonsteroidal anti-inflammatory drugs, and/or diphenhydramine may be administered.

In the case of a severe allergic reaction (eg, anaphylaxis), SC aqueous epinephrine, corticosteroids, respiratory assistance, and other proper resuscitative measures are essential and must be available at the study site where the injections or infusions are being administered.

Participants who experience serious adverse reactions related to an injection or infusion should be discontinued from further study intervention administrations.

Participants who experience reactions following an injection or infusion that result in bronchospasm with wheezing and/or dyspnea that requires ventilatory support, or symptomatic hypotension with a decrease in systolic blood pressure greater than 40 mm Hg will not be permitted to receive additional study intervention.

Participants who experience reactions suggestive of serum sickness-like reactions (resulting in symptoms such as myalgia and/or arthralgia with fever and/or rash that are not representative of signs and symptoms of other recognized clinical syndromes) occurring 1 to 14 days after an injection of study intervention, should be discontinued from further study intervention administrations. Note that these symptoms may be accompanied by other events including pruritus, facial, hand, or lip edema, dysphagia, urticaria, sore throat, and/or headache.

Adverse Events Temporally Related to Infusion

Any AE (except laboratory abnormalities) that occurs during or within 1 hour after the IV infusion of study intervention will be carefully evaluated. Minor infusion-related AEs may be managed by slowing the rate of the IV infusion and/or treating with antihistamines and/or acetaminophen (paracetamol) as clinically indicated. If an IV infusion of study intervention is stopped because of an AE that, in the opinion of the investigator, is not severe or does not result in a serious adverse event (SAE), the infusion may be restarted with caution.

Injection-Site Reaction

An injection-site reaction is any adverse reaction at a SC study intervention injection site. Injection sites will be evaluated for reactions and any injection-site reaction will be recorded as an AE.

Columbia-Suicide Severity Rating Scale (C-SSRS) The C-SSRS defines 5 subtypes of suicidal ideation and 4 possible suicidal behaviors, as well as non-suicidal self-injurious behavior and completed suicide. It will be used as a screening tool to prospectively evaluate suicidal ideation and behavior in this study, as part of a comprehensive evaluation of safety. The C-SSRS is an investigator-administered questionnaire. Two versions of it will be used in this study: the 'Baseline/Screening' version of the C-SSRS will be conducted during the screening visit and the 'Since Last Visit' version of the C-SSRS will be completed at all other visits through the end of the study.

The investigator or trained study-site personnel will interview the participant and complete the C-SSRS. The C-SSRS will be provided in the local languages in accordance with local guidelines.

At screening, the C-SSRS will be the first assessment performed, before any other study procedure. At all subsequent visits, the C-SSRS will be performed according to the assessment schedule and should be performed after other PROs but before any other study procedure. Participants will be interviewed by the investigator or trained study-site personnel in a private, quiet place.

At the conclusion of each assessment, the trained personnel administering the C-SSRS will determine the level of suicidal ideation or behavior, if any. They will then determine the next course of action if any level of suicidal ideation or behavior is reported. The participant should not be released from the site until the C-SSRS has been reviewed by the investigator and the participant's risk has been assessed and follow-up determined, as appropriate.

At screening (within the last 6 months) and Week 0, participants with a C-SSRS rating of Suicidal Ideation with Intention to Act ("Ideation level 4"), Suicidal Ideation with Specific Plan and Intent ("Ideation level 5"), or suicidal behavior (actual suicide attempt, interrupted suicide attempt, aborted suicide attempt, or preparatory behaviors for making a suicide attempt), must be determined to not be at risk by the investigator based on an evaluation by a mental health professional (eg, psychiatrist, psychologist, or appropriately trained social worker or nurse) in order to be randomized.

Participants with C-SSRS ratings of Wish to be Dead ("Ideation level 1"), Non-Specific Active Suicidal Thoughts ("Ideation level 2"), Active Suicidal Ideation with Any Methods (Not Plan) without Intent to Act ("Ideation level 3") or non-suicidal self-injurious behavior must be determined not to be at risk by the investigator in order to be randomized. Any questions regarding eligibility of such participants should be discussed with the medical monitor or designee.

For each assessment after Week 0, the following actions should be taken, if applicable:
  No suicidal ideation or behaviors (including self-injurious behavior without suicidal intent): No further action is needed.
  Suicidal ideation levels 1-3 or non-suicidal self-injurious behavior: Participant risk is assessed by the investigator.

Suicidal ideation levels 4 or 5 or any suicidal behavior: Participant risk assessed and referral to a mental health professional.

Interruption or the discontinuation of study treatment should be considered for any participant who reports Suicidal Ideation with Intention to Act ("Ideation level 4"), Suicidal Ideation with Specific Plan and Intent ("Ideation level 5"), or suicidal behavior (actual suicide attempt, interrupted suicide attempt, aborted suicide attempt, or preparatory behaviors for making a suicide attempt) on a post-baseline C-SSRS assessment and who is deemed to be at risk by the investigator based upon evaluation by a mental health professional. If a participant can be adequately treated with psychotherapy and/or pharmacotherapy then the participant, at the discretion of the investigator, may be continued with treatment if agreed to by the medical monitor or designee. Discussion of such participants with the medical monitor or designee is required.

Any C-SSRS finding, which in the opinion of the investigator is new or considered to be a worsening and clinically significant, should be reported on the AE eCRF, Adverse Events: Definitions and Procedures for Recording, Evaluating, Follow-up, and Reporting).

Clinical Safety Laboratory Assessments

Blood samples for serum chemistry and hematology will be collected. The investigator must review the laboratory results, document this review, and record any clinically relevant changes occurring during the study in the AE section of the eCRF. The laboratory reports must be filed with the source documents.

The following tests will be performed by the central laboratory unless otherwise specified or approved by the medical monitor.

Hematology assessments will include but are not limited to the following: hemoglobin, hematocrit, platelet count, total and differential WBC count.

Blood chemistry assessments will include but are not limited to the following: chemistry panel (total and direct bilirubin, ALT, AST, alkaline phosphatase, albumin, total protein, calcium, phosphate, sodium, potassium, chloride, blood urea nitrogen/urea, and creatinine).

A medical monitor or delegate and the clinical site will be notified if pre-specified abnormal laboratory values defined in the Laboratory Manual are identified in any participant during the conduct of the study.

Serology: HIV antibody, HBV antibodies and surface antigen, and HCV antibody

Abnormal liver function tests: If laboratory testing for a subject who is enrolled in the study and receiving study intervention reveals an increase of serum aminotransferases (ALT or AST) to >3×ULN and an increase of bilirubin to >2×ULN, study agent should be suspended immediately. In addition, laboratory tests for ALT, AST, alkaline phosphatase, and total bilirubin should be confirmed by a retest within 24 hours if possible, but no later than 72 hours following notification of test results.

Pregnancy testing: Female participants of childbearing potential will undergo a urine pregnancy test at screening before each study intervention administration, at a SID visit, and at the FES visit.

Immunogenicity Assessments (Antibodies to Guselkumab and Ustekinumab)

Serum samples will be screened for antibodies binding to guselkumab or ustekinumab and the titer of confirmed positive samples will be reported as applicable. Other analyses may be performed to further characterize the immunogenicity of guselkumab or ustekinumab. Antibodies to guselkumab or ustekinumab will be evaluated on blood drawn from all participants. Additionally, samples should also be collected at the final visit for participants who terminate from the study. These samples will be tested by the sponsor or sponsor's designee. Genetic analyses will not be performed on these serum samples. Participant confidentiality will be maintained.

Evaluations

At visits where antibodies to study intervention will be evaluated in addition to serum concentration of study intervention, 1 venous blood sample of sufficient volume should be collected. Each serum sample will be divided into 3 aliquots (1 each for serum concentration of study intervention, antibodies to study intervention, and a back-up).

Analytical Procedures

The detection and characterization of antibodies to guselkumab and ustekinumab will be performed using validated assay methods by or under the supervision of the sponsor.

Medication Review

Concomitant medications will be reviewed at each visit.

Adverse Events and Serious Adverse Events

Timely, accurate, and complete reporting and analysis of safety information from clinical studies are crucial for the protection of participants, investigators, and the sponsor, and are mandated by regulatory agencies worldwide. The sponsor has established Standard Operating Procedures in conformity with regulatory requirements worldwide to ensure appropriate reporting of safety information; all clinical studies conducted by the sponsor or its affiliates will be conducted in accordance with those procedures.

Adverse events will be reported by the participant (or, when appropriate, by a caregiver, surrogate, or the participant's legally acceptable representative) for the duration of the study.

Anticipated events will be recorded and reported.

Time Period and Frequency for Collecting Adverse Event and Serious Adverse Event Information All Adverse Events All AEs and special reporting situations, whether serious or non-serious, will be reported from the time a signed and dated ICF is obtained until completion of the participant's last study-related procedure, which may include contact for follow-up of safety. Serious adverse events, including those spontaneously reported to the investigator within 16 weeks after the last dose of study intervention, must be reported using the Serious Adverse Event Form. The sponsor will evaluate any safety information that is spontaneously reported by an investigator beyond the time frame specified in the protocol.

Serious Adverse Events

All SAEs occurring during the study must be reported to the appropriate sponsor or designee contact person by study-site personnel within 24 hours of their knowledge of the event. Information regarding SAEs will be transmitted to the sponsor or designee using the Serious Adverse Event Form, which must be completed and reviewed by a physician from the study site, and transmitted to the sponsor or designee within 24 hours.

Follow-Up of Adverse Events and Serious Adverse Events

Adverse events, including pregnancy, will be followed by the investigator.

Regulatory Reporting Requirements for Serious Adverse Events

The sponsor assumes responsibility for appropriate reporting of AEs to the regulatory authorities. The sponsor will also report to the investigator (and the head of the investigational institute where required) all SUSARs. The investigator (or sponsor where required) must report SUSARs to the appropriate IEC/IRB that approved the protocol unless otherwise required and documented by the IEC/IRB. A SUSAR will be reported to regulatory authorities unblinded. Participating investigators and IEC/IRB will receive a blinded SUSAR summary, unless otherwise specified.

Pregnancy

All initial reports of pregnancy in female participants or partners of male participants must be reported to the sponsor or designee by the study-site personnel within 24 hours of their knowledge of the event using the appropriate pregnancy notification form. Abnormal pregnancy outcomes (eg, spontaneous abortion, fetal death, stillbirth, congenital anomalies, ectopic pregnancy) are considered SAEs and must be reported using the Serious Adverse Event Form. Any participant who becomes pregnant during the study must discontinue further study intervention.

Follow-up information regarding the outcome of the pregnancy and any postnatal sequelae in the infant will be required.

Events of Special Interest

Any newly identified malignancy or case of active TB occurring after the first study intervention administration(s) in participants participating in this clinical study must be reported by the investigator. Investigators are also advised that active TB is considered a reportable disease in most countries. These events are to be considered serious only if they meet the definition of an SAE.

Treatment of Overdose

For this study, any dose of study intervention greater than the highest dose at a single dosing visit specified in this protocol will be considered an overdose. The sponsor does not recommend specific intervention for an overdose.

In the event of an overdose, the investigator or treating physician should:

Contact the Medical Monitor immediately.

Closely monitor the participant for AE/SAE and laboratory abnormalities.

Document the quantity of the excess dose in the eCRF.

Decisions regarding dose interruptions or modifications will be made by the investigator in consultation with the Medical Monitor based on the clinical evaluation of the participant.

Pharmacokinetics

Serum samples will be used to evaluate the PK of guselkumab and ustekinumab. Samples collected for the analyses of serum concentrations of guselkumab and ustekinumab may additionally be used to evaluate safety or efficacy aspects that address concerns arising during or after the study period, or for the evaluation of relevant biomarkers. Genetic analyses will not be performed on these serum samples. Participant confidentiality will be maintained.

Evaluations

At visits where only serum concentration of study intervention will be evaluated (ie, no antibodies to study intervention will be evaluated), 1 venous blood sample of sufficient volume should be collected, and each serum sample should be divided into 2 aliquots (1 for serum concentration of study intervention, and a back-up). At visits where serum concentration of study intervention and antibodies to study intervention will be evaluated, 1 venous blood sample of sufficient volume should be collected. Each serum sample will be divided into 3 aliquots (1 each for serum concentration of study intervention, antibodies to study intervention, and a back-up).

Analytical Procedures

Serum samples will be analyzed to determine concentrations of guselkumab and ustekinumab using respective validated, specific, and sensitive methods by or under the supervision of the sponsor's respective assay methods.

Pharmacokinetic Parameters

Serum samples will be used to evaluate various guselkumab PK parameters based on blood drawn from all participants according to the Schedule of Activities.

Pharmacodynamics

Inflammatory PD markers will be evaluated using blood samples collected at visits Post-baseline PD test results will not be released to the investigators by the central laboratory.

CRP has been demonstrated to be useful as a marker of inflammation in patients with IBD. In Crohn's disease, elevated CRP concentrations have been associated with severe clinical activity, elevated sedimentation rate, and active disease as detected by colonoscopy. Blood samples for the measurement of CRP will be collected from all participants. CRP will be evaluated using a validated, high-sensitivity assay.

Fecal calprotectin has been demonstrated to be a sensitive and specific marker in identifying intestinal inflammation and response to treatment in patients with IBD.3 Stool samples for fecal calprotectin concentration will be collected from all participants. The assay for fecal calprotectin concentration will be performed using a validated method. Additional tests may also be performed on the stool samples for additional markers related to intestinal inflammation and treatment response such as the microbiome.

Genetics

A pharmacogenomic blood sample will be collected from participants who consent separately to this component of the study to allow for pharmacogenomic research, as necessary where local regulations permit. Participation in pharmacogenomic research is optional.

Genetic (DNA) variation may be an important contributory factor to interindividual variability in drug response and associated clinical outcomes. Genetic factors may also serve as markers for disease susceptibility and prognosis, and may identify population subgroups that respond differently to an intervention.

DNA samples will be analyzed for identification of genetic factors that may be associated with clinical response. This research may consist of the analysis of 1 or more candidate genes, assessment of Single Nucleic Polymorphisms (SNPs), or analysis of the entire genome (as appropriate) in relation to guselkumab or ustekinumab intervention and/or Crohn's disease. Whole blood samples of approximately 10 mL will be collected for genetic analyses.

Phase 2 Dose-Ranging Study (GALAXI 1)

The primary hypothesis is that guselkumab is superior to placebo as assessed by the reduction from baseline in CDAI at Week 12.

Phase 3 Dose-Confirming Studies (GALAXI 2 and GALAXI 3)

The primary hypothesis is that guselkumab treatment is superior to placebo as assessed by the proportion of participants achieving clinical remission at Week 12.

For the major secondary hypotheses for comparison with ustekinumab, while the ultimate goal is to demonstrate that the efficacy of guselkumab is superior to ustekinumab, an initial test for non-inferiority is included because the overall profile of guselkumab may be favorable compared with ustekinumab (in terms of overall efficacy and safety), even if final results only indicate the relative efficac Sample Size Determination
Assumptions Data from several sources informed the underlying assumptions for sample size determination in Phase 2 and Phase 3, as summarized in the below sections. These include the ustekinumab Crohn's disease Phase 3 program consisting of 3 studies (ie, CNTO1275CRD3001, CNTO1275CRD3002, and CNTO1275CRD3003), a program conducted by the sponsor in participants with Crohn's disease who had previously failed or were intolerant to TNF-antagonist therapy (referred to as TNF-Failure herein) or had previously failed or were intolerant to conventional therapies (referred to as CON-Failure herein), and the data from a risankizumab Crohn's disease Phase 2 study in which the majority of participants were those who had previously failed or were intolerant to biologic therapies (referred to as BIO-Failure herein).

Clinical Remission at Week 12

Assumptions for the BIO-Failure population at Week 12 were based on the following:
 In CNT01275CRD3001, the proportions of participants in clinical remission (CDAI<150) at Week 8 were 7.3% and 20.9% for placebo and ustekinumab ~6 mg/kg, respectively, for a treatment difference of 13.6%.8
 Based on a clinical remission rate of 15% for placebo at Week 12, the risankizumab Phase 2 study suggested an approximate 9% difference in clinical remission between 200 mg IV and placebo, and an approximate 21% difference between 600 mg IV and placebo at Week 12.7

Based on these data, the clinical remission rates are assumed to be 10% for placebo, 20% for guselkumab 200 mg IV, and 30% for guselkumab 600 mg IV at Week 12 in the BIO-Failure population.

Assumptions for the CON-Failure population at Week 12 were based on the following:
 In CNTO1275CRD3002, the proportions of participants in clinical remission at Week 8 were 19.6% and 40.2% for placebo and ustekinumab ~6 mg/kg, respectively, for a treatment difference of 20.6%.8
 No data are currently available for guselkumab or other anti-IL-23 agents in the CON-Failure population. Based on the data from CNTO1275CRD3002 and historical biologic studies in similar populations, it is reasonable to assume a greater treatment effect difference between active and placebo in the CON-Failure population compared with that observed in a BIO-failure population. In addition, the dose-response trend in the CON-Failure population is assumed to be similar to that observed in the BIO-Failure population.

Based on these data and assumptions, the clinical remission rates are assumed to be 20% for placebo, 40% for guselkumab 200 mg IV, and 50% for guselkumab 600 mg IV in the CON-Failure population.

In the absence of data for the 1200 mg IV dose from guselkumab or from other anti-IL-23 agents, to be conservative, the clinical remission rate for guselkumab 1200 mg IV is assumed to be similar to that for guselkumab 600 mg IV, at a minimum, for both BIO-Failure and CON-Failure populations.

Taking into account a mixed BIO-Failure/CON-Failure population, assumptions for the overall randomized population at Week 12 were based on the following:
 Based on the ratio of a minimum of 25% and up to 50% of participants in the CON-Failure patient population, the proportions of participants in clinical remission at Week 12 is expected to be approximately 12% to 15% for placebo, approximately 25% to 30% for guselkumab 200 mg IV, and approximately 35% to 40% for both guselkumab 600 mg IV and guselkumab 1200 mg IV.

Change in CDAI at Week 12

Assumptions for the BIO-Failure population and the CON-Failure population were based on the following:
 In CNTO1275CRD3001, the mean CDAI change from baseline at Week 8 was −25.1 (SD=91.41) and −78.7 (SD=91.79) for the placebo and ustekinumab 6 mg/kg groups, respectively.8
 In CNTO1275CRD3002, the mean CDAI change from baseline at Week 8 was −66.3 (SD=97.81) and −116.3 (SD=102.88) for the placebo and ustekinumab 6 mg/kg groups, respectively.8

Taking into account a mixed BIO-Failure/CON-Failure population, the mean CDAI reduction from baseline at Week 12 is expected to be approximately 45 to 50 for placebo, approximately 85 to 95 for guselkumab 200 mg IV, and approximately 105 to 115 for guselkumab 600 mg IV and guselkumab 1200 mg IV at Week 12 with a common SD of 100 (considering increased variability in a relatively smaller Phase 2 study).

Clinical Remission at Week 48

Rates for clinical remission at Week 48 were derived by combining the randomized and non-randomized population in CNT01275CRD3003, resulting in a clinical remission rate of 23% in TNF-Failure participants and 50% in CON-Failure participants for ustekinumab. As such, the overall randomized population with a minimum of 25% and up to 50% of the participants being from the CON-Failure population is expected to achieve approximately 30% to 36% clinical remission at Week 48 for ustekinumab. A meaningful difference of 15% in clinical remission between guselkumab and ustekinumab is assumed at Week 48.

Power and Sample Size Calculations

Phase 2 Dose-Ranging Study (GALAXI 1)

Power for Phase 2 was evaluated for the 2 analysis populations described below, using a 2-sample t-test (at the 0.05 level of significance) to detect a significant difference in the change from baseline in the CDAI score at Week 12 between the guselkumab high IV induction dose and placebo.

Assuming the mean CDAI reductions from baseline at Week 12 of approximately 105 to 115 in the guselkumab high IV induction dose group versus approximately 45 to 50 in the placebo group with a common SD of 100:
 For the Initial Dose Decision Cohort: 50 participants in the guselkumab high IV induction dose group and 50 participants in the placebo group will provide greater than 80% power to detect a treatment difference between guselkumab and placebo at a Type 1 error rate controlled at $\alpha=0.05$ (2-sided) (Table 8). With 5 dose groups, the total sample size for the Initial Dose Decision Cohort is 250 subjects.
 For the Total Phase 2 Population: It is anticipated that 100 to 250 participants will be enrolled into the Transition Cohort by the time a dose decision is made for Phase 3. Thus, the sample size for the total Phase 2 study is expected to range from a minimum of 350 participants (70 per dose group) up to a maximum of 500 participants (100 per dose group). The power, based on the minimum number of participants, is greater than 90% for the change from baseline in the CDAI score at Week 12 and greater than 85% for clinical remission at Week 12 (Table 8). Table 8: Power to detect a treatment effect of guselkumab versus placebo based on mean change in CDAI and proportion of participants achieving clinical remission at Week 12

Safety Analyses

Adverse Events

The verbatim terms used in the eCRF by investigators to identify AEs will be coded using the Medical Dictionary for Regulatory Activities. Treatment-emergent AEs are AEs with onset during the intervention phase or that are a consequence of a pre-existing condition that has worsened since baseline. All reported treatment-emergent AEs will be included in the analysis. For each AE, the percentage of participants who experience at least 1 occurrence of the given event will be summarized by intervention group.

The following analyses of AEs will be used to assess the safety of participants:

Frequency and type of AEs.
Frequency and type of SAEs.
Frequency and type of reasonably related AEs as assessed by the investigator.
Frequency and type of AEs leading to discontinuation of study intervention.
Frequency and type of infections.
Frequency and type of AEs temporally associated with infusion.
Frequency and type of injection-site reactions.

Summaries, listings, datasets, or participant narratives may be provided, as appropriate, for those participants who die, who discontinue intervention due to an AE, or who experience a severe or a serious AE.

Clinical Laboratory Tests

The following summaries of clinical laboratory tests will be used to assess participant safety:

Laboratory parameters and change from baseline in laboratory parameters (hematology and chemistry).
Summary of maximum NCI-CTCAE toxicity grade for post-baseline laboratory values (hematology and chemistry).
Listings of participants with any abnormal post-baseline laboratory values of NCI-CTCAE grade ≥2 will also be provided.

Suicidal Ideation and Behavior

Suicidal ideation and behavior based on the C-SSRS and AEs will be summarized descriptively.

Other Analyses

Pharmacokinetic Analyses

Descriptive statistics of the serum guselkumab and ustekinumab concentrations will be calculated at each sampling time point. These concentrations will be summarized over time for each treatment group.

All concentrations below the lowest quantifiable concentration or missing data will be labeled as such in the concentration database or data presentations. Concentrations below the lowest quantifiable concentration will be treated as zero in the summary statistics.

A population PK analysis approach using nonlinear mixed-effects modeling will be used to evaluate guselkumab PK parameters. The influence of important covariates on the population PK parameter estimates may be evaluated. Details will be provided in a population PK analysis plan and the results of the population PK analysis will be presented in a separate technical report.

Participants will be excluded from the PK analysis if their data do not allow for accurate assessment of the PK (eg, incomplete administration of the study intervention; missing time of study intervention administration). Detailed rules for the analysis will be specified in the SAPs.

Immunogenicity Analyses

The incidence and titers of antibodies to guselkumab and ustekinumab will be summarized respectively for all participants who receive a dose of guselkumab or ustekinumab and have appropriate samples for detection of antibodies to guselkumab or ustekinumab (ie, participants with at least 1 sample obtained after their first dose of guselkumab or ustekinumab).

A listing of participants who are positive for antibodies to guselkumab or ustekinumab will be provided. The maximum titers of antibodies to guselkumab or ustekinumab will be provided for participants who are positive for antibodies to guselkumab or ustekinumab.

The incidence of neutralizing antibodies (NAbs) to guselkumab or ustekinumab will be summarized for participants who are positive for antibodies to guselkumab or ustekinumab and have samples evaluable for NAbs to guselkumab or ustekinumab.

Biomarkers Analyses

Planned biomarker analyses may be deferred if emerging study data show no likelihood of providing useful scientific information. Any biomarker samples received by the contract vendor or sponsor after the cutoff date will not be analyzed, and therefore, excluded from the biomarker analysis.

Changes in serum protein analytes and whole blood RNA obtained over time will be summarized by treatment group. Associations between baseline levels and changes from baseline in select markers and response to treatment will be explored. RNA analyses will be summarized in a separate technical report.

The biomarker analyses will characterize the effects of guselkumab to identify biomarkers relevant to treatment, and to determine if these biomarkers can predict response to guselkumab. Results of serum, whole blood analyses, stool, and mucosal biopsy analyses will be reported in separate technical reports.

Pharmacokinetic/Pharmacodynamic Analyses

The relationship between serum guselkumab concentrations and efficacy measures will be analyzed graphically. If any visual trend is observed, a suitable population PK/PD model may be developed to describe the E-R relationship. Details will be provided in a population PK/PD analysis plan and results of the population PK/PD analysis will be presented in a separate technical report.

Medical Resource Utilization and Health Economics Analyses

Medical resource utilization and health economics, including work productivity, will be summarized by treatment group.

```
Sequence Listing
<210> 1
<211> 5
<212> PRT
<213> Homo sapiens
<400> 1
```

Asn Tyr Ala Ile Ser
1               5

<210> 2
<211> 5
<212> PRT
<213> Homo sapiens
<400> 2
Ser Asn Tyr Ile Ser
1               5

<210> 3
<211> 5
<212> PRT
<213> Homo sapiens
<400> 3
Asn Tyr Trp Ile Ser
1               5

<210> 4
<211> 5
<212> PRT
<213> Homo sapiens
<400> 4
Ser Tyr Trp Ile Thr
1               5

<210> 5
<211> 5
<212> PRT
<213> Homo sapiens
<400> 5
Asn Tyr Trp Ile Gly
1               5

<210> 6
<211> 5
<212> PRT
<213> Homo sapiens
<400> 6
Ser Phe Gly Met Ser
1               5

<210> 7
<211> 17
<212> PRT
<213> Homo sapiens
<400> 7
Gly Ile Ile Pro Met Phe Gly Tyr Ala Asn Tyr Ala Gln Lys Phe Gln
1               5                   10                  15
Gly <210> 8
<211> 17
<212> PRT
<213> Homo sapiens
<400> 8
Gly Ile Ile Pro Val Phe Gly Phe Thr His Tyr Ala Gln Lys Phe Gln
1               5                   10                  15
Gly <210> 9
<211> 17
<212> PRT
<213> Homo sapiens
<400> 9
Gly Ile Ile Pro Ile Phe Gly His Ala Asn Tyr Ala Gln Lys Phe Gln
1               5                   10                  15
Gly <210> 10
<211> 17
<212> PRT
<213> Homo sapiens
<400> 10
Ile Ile Ile Pro Pro Ile Gly Asn Ala Trp Tyr Ala Gln Lys Phe Gln
1               5                   10                  15
Gly

<210> 11
<211> 17

-continued

<212> PRT
<213> Homo sapiens
<400> 11
Leu Ile Asp Pro Asn Phe Gly Gly Ala Tyr Tyr Ala Gln Lys Phe Gln
1               5                   10                  15
Gly <210> 12
<211> 17
<212> PRT
<213> Homo sapiens
<400> 12
Leu Ile Asp Pro Val Phe Gly Gly Ala Tyr Tyr Ala Gln Lys Phe Gln
1               5                   10                  15
Gly <210> 13
<211> 17
<212> PRT
<213> Homo sapiens
<400> 13
Leu Ile Asp Pro Met Phe Gly Gly Ala Tyr Tyr Ala Gln Lys Phe Gln
1               5                   10                  15
Gly <210> 14
<211> 16
<212> PRT
<213> Homo sapiens
<400> 14
Ile Asn Ala His Leu Gly Gly Thr Trp Tyr Ala Gln Lys Phe Gln Gly
1               5                   10                  15

<210> 15
<211> 17
<212> PRT
<213> Homo sapiens
<400> 15
Ile Ser Pro Gly Thr Gly Ile Asn Ala Tyr Tyr Ala Gln Lys Phe Gln
1               5                   10                  15
Gly <210> 16
<211> 17
<212> PRT
<213> Artificial Sequence
<220>
<223> Synthesized human sequence
<220>
<221> unsure
<222> (1)
<223> Where Xaa can be G, I, or L
<220>
<221> unsure
<222> (2)
<223> Where Xaa can be I or S
<220>
<221> unsure
<222> (3)
<223> Where Xaa can be I, P, N, or D
<220>
<221> unsure
<222> (4)
<223> Where Xaa can be P, G, or A
<220>
<221> unsure
<222> (5)
<223> Where Xaa can be I, M, P,
<223> T, H, N, or V
<220>
<221> unsure
<222> (6)
<223> Where Xaa can be F, I, G, or L
<220>
<221> unsure
<222> (7)
<223> Where Xaa can G or I
<220>
<221> unsure
<222> (8)
<223> Where Xaa can be H, Y, N, or G

```
<220>
<221> unsure
<222> (9)
<223> Where Xaa can be A or T
<220>
<221> unsure
<222> (10)
<223> Where Xaa can be N, W, or Y
<400> 16
Xaa Xaa Xaa Xaa Xaa Xaa Xaa Xaa Xaa Tyr Ala Gln Lys Phe Gln
1               5                   10                  15
Gly <210> 17
<211> 17
<212> PRT
<213> Homo sapiens
<400> 17
Trp Ile Arg Pro Gly Asp Ser Asp Thr Arg Tyr Ser Pro Ser Phe Glu
1               5                   10                  15
Gly <210> 18
<211> 19
<212> PRT
<213> Homo sapiens
<400> 18
Val Ser Tyr Ile Ser Ser Ser Gly Ser Ser Thr Tyr Tyr Ala Asp Ser
1               5                   10                  15
Val Lys Gly <210> 19
<211> 17
<212> PRT
<213> Homo sapiens
<400> 19
Ile Ile Asp Pro Ser Asn Ser Tyr Thr Asn Tyr Ser Pro Ser Phe Gln
1               5                   10                  15
Gly <210> 20
<211> 17
<212> PRT
<213> Homo sapiens
<400> 20
Ile Ile Asp Pro Ser Asn Ser Tyr Thr Arg Tyr Ser Pro Ser Phe Gln
1               5                   10                  15
Gly <210> 21
<211> 17
<212> PRT
<213> Homo sapiens
<400> 21
Ile Ile Asp Pro Ser Asn Ser Tyr Thr Asp Tyr Ser Pro Ser Phe Gln
1               5                   10                  15
Gly <210> 22
<211> 17
<212> PRT
<213> Homo sapiens
<400> 22
Ile Ile Ser Pro Thr Gly Ser Val Thr Trp Tyr Ser Pro Ser Phe Gln
1               5                   10                  15
Gly <210> 23
<211> 17
<212> PRT
<213> Homo sapiens
<400> 23
Ile Ile Ser Pro Thr Gly Ser Ser Thr Trp Tyr Ser Pro Ser Phe Gln
1               5                   10                  15
Gly <210> 24
<211> 17
<212> PRT
<213> Homo sapiens
<400> 24
```

-continued

Phe Ile Ser Pro Asp Gly Ser His Thr Trp Tyr Ser Pro Ser Phe Gln
1               5                   10                  15
Gly

<210> 25
<211> 17
<212> PRT
<213> Homo sapiens
<400> 25
Ile Ile Ser Pro Ser Gly Ser Thr Thr Trp Tyr Ser Pro Ser Phe Gln
1               5                   10                  15
Gly <210> 26
<211> 17
<212> PRT
<213> Homo sapiens
<400> 26
Ile Ile Ser Pro Thr Gly Ser Ala Thr Trp Tyr Ser Pro Ser Phe Gln
1               5                   10                  15
Gly <210> 27
<211> 17
<212> PRT
<213> Homo sapiens
<400> 27
Ile Ile Asp Pro Val Ser Ser Trp Thr Lys Tyr Ser Pro Ser Phe Gln
1               5                   10                  15
Gly <210> 28
<211> 17
<212> PRT
<213> Artificial Sequence
<220>
<223> Synthesized human sequence
<220>
<221> unsure
<222> (3)
<223> Where Xaa can be D or S
<220>
<221> unsure
<222> (5)
<223> Where Xaa can be S, V, D, or T
<220>
<221> unsure
<222> (6)
<223> Where Xaa can be N, S, or G
<220>
<221> unsure
<222> (8)
<223> Where Xaa can be Y, W, T, H, V, S, or A
<220>
<221> unsure
<222> (10)
<223> Where Xaa can be N, D, R, K, or W
<400> 28
Ile Ile Xaa Pro Xaa Xaa Ser Xaa Thr Xaa Tyr Ser Pro Ser Phe Gln
1               5                   10                  15
Gly <210> 29
<211> 17
<212> PRT
<213> Homo sapiens
<400> 29
Asn Ile Ser Ser Ser Gly Ser Ser Thr Tyr Tyr Ala Asp Ser Val Lys
1               5                   10                  15
Gly <210> 30
<211> 19
<212> PRT
<213> Homo sapiens
<400> 30
Asn Ile Glu His Lys Tyr Leu Asn Tyr Ala Thr Tyr Tyr Ala Ala Ser
1               5                   10                  15
Val Lys Gly

<210> 31

```
<211> 19
<212> PRT
<213> Homo sapiens
<400> 31
Asn Ile Glu His Lys Phe Met Gly Tyr Thr Thr Tyr Tyr Ala Ala Gly
1               5                   10                  15
Val Lys Gly <210> 32
<211> 19
<212> PRT
<213> Homo sapiens
<400> 32
Gly Ile Glu His Lys Tyr Leu Ser Tyr Thr Thr His Tyr Ala Ala Ser
1               5                   10                  15
Val Lys Gly <210> 33
<211> 19
<212> PRT
<213> Homo sapiens
<400> 33
Ser Ile Glu His Lys Tyr Thr Gly Tyr Thr Thr Tyr Tyr Ala Ala Pro
1               5                   10                  15
Val Lys Gly <210> 34
<211> 19
<212> PRT
<213> Homo sapiens
<400> 34
Gln Ile Glu His Lys Tyr Leu Ser Tyr Thr Thr Leu Tyr Ala Ala Ser
1               5                   10                  15
Val Lys Gly <210> 35
<211> 19
<212> PRT
<213> Homo sapiens
<400> 35
Ser Ile Glu His Lys Tyr Leu Ser Tyr Thr Thr Phe Tyr Ala Ala Ser
1               5                   10                  15
Val Lys Gly <210> 36
<211> 19
<212> PRT
<213> Homo sapiens
<400> 36
Asn Ile Glu Gly Lys Tyr Thr Ser Tyr Thr Thr Tyr Tyr Ala Ala Ser
1               5                   10                  15
Val Lys Gly <210> 37
<211> 19
<212> PRT
<213> Homo sapiens
<400> 37
Gly Ile Glu His Lys Tyr Leu Ser Tyr Ala Thr Leu Tyr Ala Ala Ser
1               5                   10                  15
Val Lys Gly <210> 38
<211> 19
<212> PRT
<213> Homo sapiens
<400> 38
Asn Ile Glu His Lys Tyr Leu Gly Tyr Ala Thr Val Tyr Ala Ala Ser
1               5                   10                  15
Val Lys Gly <210> 39
<211> 19
<212> PRT
<213> Homo sapiens
<400> 39
Ser Ile Glu His Lys Tyr Leu Ser Tyr Ala Thr Tyr Tyr Ala Ala Gly
1               5                   10                  15
Val Lys Gly

<210> 40
```

-continued

<211> 8
<212> PRT
<213> Homo sapiens
<400> 40
Asp Ile Tyr Ala Gly Met Asp Val
1               5

<210> 41
<211> 18
<212> PRT
<213> Homo sapiens
<400> 41
Ser Lys Lys Gly Met Tyr Gly Gly Trp Thr Tyr Pro Leu Met Met Phe
1               5                   10                  15
Asp Leu <210> 42
<211> 7
<212> PRT
<213> Homo sapiens
<400> 42
His Tyr Tyr Gly Met Asp Tyr
1               5

<210> 43
<211> 12
<212> PRT
<213> Homo sapiens
<400> 43
Gly Thr Phe Trp Ser Phe Gly Asn Tyr Phe Ala Asn
1               5                   10

<210> 44
<211> 8
<212> PRT
<213> Homo sapiens
<400> 44
Trp Tyr Tyr Lys Pro Phe Asp Val
1               5

<210> 45
<211> 12
<212> PRT
<213> Homo sapiens
<400> 45
Tyr Trp Gly Thr Pro Tyr Leu Met Gln Phe Asp Asn
1               5                   10

<210> 46
<211> 12
<212> PRT
<213> Homo sapiens
<400> 46
Arg Ala Ser Gln Ser Val Leu Gly Asn Tyr Leu Ala
1               5                   10

<210> 47
<211> 12
<212> PRT
<213> Homo sapiens
<400> 47
Arg Ala Ser Gln Ser Val Ser Ser Asn Tyr Leu Ala
1               5                   10

<210> 48
<211> 13
<212> PRT
<213> Homo sapiens
<400> 48
Ser Gly Ser Ser Ser Asn Ile Gly Ser Tyr Tyr Val Asn
1               5                   10

<210> 49
<211> 11
<212> PRT
<213> Homo sapiens
<400> 49
Arg Ala Ser Gln Ser Ile Phe Tyr Asn Leu Ala
1               5                   10

<210> 50

```
<211> 14
<212> PRT
<213> Homo sapiens
<400> 50
Thr Gly Ser Ser Asn Ile Gly Ser Gly Tyr Asp Val His
 1               5                  10

<210> 51
<211> 14
<212> PRT
<213> Homo sapiens
<400> 51
Thr Gly Thr Ser Ser Asp Val Gly Gly Tyr Asn Ser Val Ser
 1               5                  10

<210> 52
<211> 7
<212> PRT
<213> Homo sapiens
<400> 52
Gly Ala Ser Ser Arg Ala Thr
 1               5

<210> 53
<211> 7
<212> PRT
<213> Homo sapiens
<400> 53
Tyr Ala Ser Arg Arg Ala Thr
 1               5

<210> 54
<211> 7
<212> PRT
<213> Homo sapiens
<400> 54
Gly Asn Thr His Arg Pro Ser
 1               5

<210> 55
<211> 7
<212> PRT
<213> Homo sapiens
<400> 55
Gly Ala Ser Asn Arg Ala Thr
 1               5

<210> 56
<211> 7
<212> PRT
<213> Homo sapiens
<400> 56
Gly Asn Ser Lys Arg Pro Ser
 1               5

<210> 57
<211> 7
<212> PRT
<213> Homo sapiens
<400> 57
Ser Val Ser Ser Arg Pro Ser
 1               5

<210> 58
<211> 9
<212> PRT
<213> Homo sapiens
<400> 58
His Gln Tyr Gly Ser Ile Ser Thr Thr
 1               5

<210> 59
<211> 9
<212> PRT
<213> Homo sapiens
<400> 59
Gln Gln Tyr Ser His Leu Leu Ile Thr
 1               5

<210> 60
<211> 9
```

-continued

<210> 60
<211> 8
<212> PRT
<213> Homo sapiens
<400> 60
Gln Gln Tyr Ser His Ile Ser Leu Thr
1               5

<210> 61
<211> 9
<212> PRT
<213> Homo sapiens
<400> 61
Gln Gln Phe Ala His Ile Leu Leu Thr
1               5

<210> 62
<211> 9
<212> PRT
<213> Homo sapiens
<400> 62
Gln Gln Thr Ser Asn Thr Pro Phe Thr
1               5

<210> 63
<211> 9
<212> PRT
<213> Homo sapiens
<400> 63
Gln Gln Phe Ile Thr Tyr Leu Pro Thr
1               5

<210> 64
<211> 9
<212> PRT
<213> Homo sapiens
<400> 64
Gln Gln Asp Ala Leu Ser Pro Phe Thr
1               5

<210> 65
<211> 9
<212> PRT
<213> Homo sapiens
<400> 65
Gln Gln Asp Arg Gly Thr Pro Phe Thr
1               5

<210> 66
<211> 9
<212> PRT
<213> Homo sapiens
<400> 66
Gln Gln Ser Leu Asn Ile Pro Phe Thr
1               5

<210> 67
<211> 9
<212> PRT
<213> Homo sapiens
<400> 67
Gln Gln Asp Thr Ser Ser Pro Phe Thr
1               5

<210> 68
<211> 10
<212> PRT
<213> Artificial Sequence
<220>
<223> Synthesized human sequence
<220>
<221> unsure
<222> (3)
<223> Where Xaa can be T, F, D, or S
<220>
<221> unsure
<222> (4)
<223> Where Xaa can be S, I, A, T, R, or L
<220>
<221> unsure
<222> (5)
<223> Where Xaa can be N, T, L, S, or G
<220>

```
<221> unsure
<222> (6)
<223> Where Xaa can be T, Y, S, or I
<220>
<221> unsure
<222> (7)
<223> Where Xaa can be P or L
<220>
<221> unsure
<222> (8)
<223> Where Xaa can be F or P
<400> 68
Gln Gln Xaa Xaa Xaa Xaa Xaa Xaa Phe Thr
 1               5                  10

<210> 69
<211> 11
<212> PRT
<213> Homo sapiens
<400> 69
Gln Thr Tyr Ala Ser Leu Gly Pro Gly Glu Val
 1               5                  10

<210> 70
<211> 9
<212> PRT
<213> Homo sapiens
<400> 70
Gln Gln Tyr Ser Ser Glu Pro Val Thr
 1               5

<210> 71
<211> 9
<212> PRT
<213> Homo sapiens
<400> 71
Ser Ser Trp Thr Pro Ser Ser Val Val
 1               5

<210> 72
<211> 11
<212> PRT
<213> Homo sapiens
<400> 72
Ser Ser Trp Thr Asp Thr Pro Asn Met Ile Val
 1               5                  10

<210> 73
<211> 11
<212> PRT
<213> Homo sapiens
<400> 73
Ala Ser Trp Thr Asp Gly Leu Ser Leu Val Val
 1               5                  10

<210> 74
<211> 11
<212> PRT
<213> Artificial Sequence
<220>
<223> Synthesized human sequence
<220>
<221> unsure
<222> (1)
<223> Where Xaa can be S or A
<220>
<221> unsure
<222> (6)
<223> Where Xaa can be T or G
<220>
<221> unsure
<222> (7)
<223> Where Xaa can be P or L
<220>
<221> unsure
<222> (8)
<223> Where Xaa can be S or N
<220>
<221> unsure
<222> (9)
<223> Where Xaa can be S, M, or L
```

```
<220>
<221> unsure
<222> (10)
<223> Where Xaa can be I or V
<400> 74
Xaa Ser Trp Thr Asp Xaa Xaa Xaa Xaa Val
1               5                   10

<210> 75
<211> 11
<212> PRT
<213> Homo sapiens
<400> 75
Ser Ser Tyr Asp Thr Asn Lys Pro Leu Val Val
1               5                   10

<210> 76
<211> 11
<212> PRT
<213> Homo sapiens
<400> 76
Gly Ser Tyr Asp Val Tyr Gly Arg Phe Tyr Val
1               5                   10

<210> 77
<211> 11
<212> PRT
<213> Homo sapiens
<400> 77
Ser Ser Tyr Tyr Phe Tyr Leu Gln Arg Ile Val
1               5                   10

<210> 78
<211> 11
<212> PRT
<213> Homo sapiens
<400> 78
Gln Thr Tyr Tyr Phe Ser Tyr Ser Gly Pro Val
1               5                   10

<210> 79
<211> 11
<212> PRT
<213> Homo sapiens
<400> 79
Gly Ser Trp Asp Pro Ile Phe Ser Tyr Glu Val
1               5                   10

<210> 80
<211> 117
<212> PRT
<213> Homo sapiens
<400> 80
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Asn Tyr
            20                  25                  30
Ala Ile Ser Trp Val Arg Gln Ala Pro Gly Gln Gly Leu Glu Trp Met
        35                  40                  45
Gly Gly Ile Ile Pro Met Phe Gly Tyr Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Asp Ile Tyr Ala Gly Met Asp Val Trp Gly Gln Gly Thr Leu
            100                 105                 110
Val Thr Val Ser Ser
        115

<210> 81
<211> 117
<212> PRT
<213> Homo sapiens
<400> 81
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Asn Tyr
            20                  25                  30
Ala Ile Ser Trp Val Arg Gln Ala Pro Gly Gln Gly Leu Glu Trp Met
        35                  40                  45
```

```
-continued
Gly Gly Ile Ile Pro Val Gly Phe Thr His Tyr Ala Gln Lys Phe
        50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Asp Ile Tyr Ala Gly Met Asp Val Trp Gly Gln Gly Thr Leu
            100                 105                 110
Val Thr Val Ser Ser
            115

<210> 82
<211> 108
<212> PRT
<213> Homo sapiens
<400> 82
Asp Ile Val Leu Thr Gln Ser Pro Ala Thr Leu Ser Leu Ser Pro Gly
 1               5                  10                  15
Glu Arg Ala Thr Leu Ser Cys Arg Ala Ser Gln Ser Val Leu Gly Asn
                20                  25                  30
Tyr Leu Ala Trp Tyr Gln Gln Lys Pro Gly Gln Ala Pro Arg Leu Leu
            35                  40                  45
Ile Tyr Gly Ala Ser Ser Arg Ala Thr Gly Val Pro Ala Arg Phe Ser
        50                  55                  60
Gly Ser Gly Ser Gly Thr Asp Phe Thr Leu Thr Ile Ser Ser Leu Glu
 65                  70                  75                  80
Pro Glu Asp Phe Ala Val Tyr Tyr Cys His Gln Tyr Gly Ser Ile Ser
                 85                  90                  95
Thr Thr Phe Gly Gln Gly Thr Lys Val Glu Ile Lys
            100                 105

<210> 83
<211> 108
<212> PRT
<213> Homo sapiens
<400> 83
Asp Ile Val Leu Thr Gln Ser Pro Ala Thr Leu Ser Leu Ser Pro Gly
 1               5                  10                  15
Glu Arg Ala Thr Leu Ser Cys Arg Ala Ser Gln Ser Val Leu Gly Asn
                20                  25                  30
Tyr Leu Ala Trp Tyr Gln Gln Lys Pro Gly Gln Ala Pro Arg Leu Leu
            35                  40                  45
Ile Tyr Gly Ala Ser Ser Arg Ala Thr Gly Val Pro Ala Arg Phe Ser
        50                  55                  60
Gly Ser Gly Ser Gly Thr Asp Phe Thr Leu Thr Ile Ser Ser Leu Glu
 65                  70                  75                  80
Pro Glu Asp Phe Ala Val Tyr Tyr Cys Gln Gln Tyr Ser His Ile Ser
                 85                  90                  95
Leu Thr Phe Gly Gln Gly Thr Lys Val Glu Ile Lys
            100                 105

<210> 84
<211> 108
<212> PRT
<213> Homo sapiens
<400> 84
Asp Ile Val Leu Thr Gln Ser Pro Ala Thr Leu Ser Leu Ser Pro Gly
 1               5                  10                  15
Glu Arg Ala Thr Leu Ser Cys Arg Ala Ser Gln Ser Val Leu Gly Asn
                20                  25                  30
Tyr Leu Ala Trp Tyr Gln Gln Lys Pro Gly Gln Ala Pro Arg Leu Leu
            35                  40                  45
Ile Tyr Gly Ala Ser Ser Arg Ala Thr Gly Val Pro Ala Arg Phe Ser
        50                  55                  60
Gly Ser Gly Ser Gly Thr Asp Phe Thr Leu Thr Ile Ser Ser Leu Glu
 65                  70                  75                  80
Pro Glu Asp Phe Ala Val Tyr Tyr Cys Gln Gln Tyr Ser His Leu Ile
                 85                  90                  95
Ile Thr Phe Gly Gln Gly Thr Lys Val Glu Ile Lys
            100                 105

<210> 85
<211> 108
<212> PRT
<213> Homo sapiens
<400> 85
Asp Ile Val Leu Thr Gln Ser Pro Ala Thr Leu Ser Leu Ser Pro Gly
 1               5                  10                  15
Glu Arg Ala Thr Leu Ser Cys Arg Ala Ser Gln Ser Val Leu Gly Asn
                20                  25                  30
```

```
                        -continued
Tyr Leu Ala Trp Tyr Gln Gln Lys Pro Gly Gln Ala Pro Arg Leu Leu
            35                  40                  45
Ile Tyr Gly Ala Ser Ser Arg Ala Thr Gly Val Pro Ala Arg Phe Ser
        50                  55                  60
Gly Ser Gly Ser Gly Thr Asp Phe Thr Leu Thr Ile Ser Ser Leu Glu
65                  70                  75                  80
Pro Glu Asp Phe Ala Val Tyr Tyr Cys Gln Gln Phe Ala His Ile Leu
                85                  90                  95
Leu Thr Phe Gly Gln Gly Thr Lys Val Glu Ile Lys
            100                 105

<210> 86
<211> 127
<212> PRT
<213> Homo sapiens
<400> 86
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Asn
            20                  25                  30
Tyr Ile Ser Trp Val Arg Gln Ala Pro Gly Gln Gly Leu Glu Trp Met
        35                  40                  45
Gly Gly Ile Ile Pro Ile Phe Gly His Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Lys Lys Gly Met Tyr Gly Gly Trp Thr Tyr Pro Leu Met
            100                 105                 110
Met Phe Asp Leu Trp Gly Gln Gly Thr Leu Val Thr Val Ser Ser
        115                 120                 125

<210> 87
<211> 127
<212> PRT
<213> Homo sapiens
<400> 87
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Asn
            20                  25                  30
Tyr Ile Ser Trp Val Arg Gln Ala Pro Gly Gln Gly Leu Glu Trp Met
        35                  40                  45
Gly Ile Ile Ile Pro Pro Ile Gly Asn Ala Trp Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Lys Lys Gly Met Tyr Gly Gly Trp Thr Tyr Pro Leu Met
            100                 105                 110
Met Phe Asp Leu Trp Gly Gln Gly Thr Leu Val Thr Val Ser Ser
        115                 120                 125

<210> 88
<211> 127
<212> PRT
<213> Homo sapiens
<400> 88
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Asn
            20                  25                  30
Tyr Ile Ser Trp Val Arg Gln Ala Pro Gly Gln Gly Leu Glu Trp Met
        35                  40                  45
Gly Ile Ser Pro Gly Thr Gly Ile Asn Ala Tyr Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Lys Lys Gly Met Tyr Gly Gly Trp Thr Tyr Pro Leu Met
            100                 105                 110
Met Phe Asp Leu Trp Gly Gln Gly Thr Leu Val Thr Val Ser Ser
        115                 120                 125

<210> 89
<211> 126
<212> PRT
<213> Homo sapiens
```

```
<400> 89
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Asn
                20                  25                  30
Tyr Ile Ser Trp Val Arg Gln Ala Pro Gly Gln Gly Leu Glu Trp Met
            35                  40                  45
Gly Ile Asn Ala His Leu Gly Gly Thr Trp Tyr Ala Gln Lys Phe Gln
        50                  55                  60
Gly Arg Val Thr Ile Thr Ala Asp Glu Ser Thr Ser Thr Ala Tyr Met
65                  70                  75                  80
Glu Leu Ser Ser Leu Arg Ser Glu Asp Thr Ala Val Tyr Tyr Cys Ala
                85                  90                  95
Arg Ser Lys Lys Gly Met Tyr Gly Gly Trp Thr Tyr Pro Leu Met Met
                100                 105                 110
Phe Asp Leu Trp Gly Gln Gly Thr Leu Val Thr Val Ser Ser
            115                 120                 125

<210> 90
<211> 127
<212> PRT
<213> Homo sapiens
<400> 90
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Asn
                20                  25                  30
Tyr Ile Ser Trp Val Arg Gln Ala Pro Gly Gln Gly Leu Glu Trp Met
            35                  40                  45
Gly Leu Ile Asp Pro Asn Phe Gly Gly Ala Tyr Tyr Ala Gln Lys Phe
        50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Lys Lys Gly Met Tyr Gly Gly Trp Thr Tyr Pro Leu Met
                100                 105                 110
Met Phe Asp Leu Trp Gly Gln Gly Thr Leu Val Thr Val Ser Ser
            115                 120                 125

<210> 91
<211> 127
<212> PRT
<213> Homo sapiens
<400> 91
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Asn
                20                  25                  30
Tyr Ile Ser Trp Val Arg Gln Ala Pro Gly Gln Gly Leu Glu Trp Met
            35                  40                  45
Gly Leu Ile Asp Pro Val Phe Gly Gly Ala Tyr Tyr Ala Gln Lys Phe
        50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Lys Lys Gly Met Tyr Gly Gly Trp Thr Tyr Pro Leu Met
                100                 105                 110
Met Phe Asp Leu Trp Gly Gln Gly Thr Leu Val Thr Val Ser Ser
            115                 120                 125

<210> 92
<211> 127
<212> PRT
<213> Homo sapiens
<400> 92
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Asn
                20                  25                  30
Tyr Ile Ser Trp Val Arg Gln Ala Pro Gly Gln Gly Leu Glu Trp Met
            35                  40                  45
Gly Leu Ile Asp Pro Met Phe Gly Gly Ala Tyr Tyr Ala Gln Lys Phe
        50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Lys Lys Gly Met Tyr Gly Gly Trp Thr Tyr Pro Leu Met
                100                 105                 110
```

```
Met Phe Asp Leu Trp Gly Gln Gly Thr Leu Val Thr Val Ser Ser
            115                 120                 125
```

<210> 93
<211> 108
<212> PRT
<213> *Homo sapiens*
<400> 93

```
Asp Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Asn
            20                  25                  30
Tyr Leu Ala Trp Tyr Gln Gln Lys Pro Gly Gln Ala Pro Arg Leu Leu
        35                  40                  45
Ile Tyr Tyr Ala Ser Arg Arg Ala Thr Gly Val Pro Ala Arg Phe Ser
    50                  55                  60
Gly Ser Gly Ser Gly Thr Asp Phe Thr Leu Thr Ile Ser Ser Leu Glu
65                  70                  75                  80
Pro Glu Asp Phe Ala Thr Tyr Tyr Cys Gln Gln Thr Ser Asn Thr Pro
                85                  90                  95
Phe Thr Phe Gly Gln Gly Thr Lys Val Glu Ile Lys
            100                 105
```

<210> 94
<211> 108
<212> PRT
<213> *Homo sapiens*
<400> 94

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Asn
            20                  25                  30
Tyr Leu Ala Trp Tyr Gln Gln Lys Pro Gly Gln Ala Pro Arg Leu Leu
        35                  40                  45
Ile Tyr Tyr Ala Ser Arg Arg Ala Thr Gly Val Pro Ala Arg Phe Ser
    50                  55                  60
Gly Ser Gly Ser Gly Thr Asp Phe Thr Leu Thr Ile Ser Ser Leu Glu
65                  70                  75                  80
Pro Glu Asp Phe Ala Val Tyr Tyr Cys Gln Gln Thr Ser Asn Thr Pro
                85                  90                  95
Phe Thr Phe Gly Gln Gly Thr Lys Val Glu Ile Lys
            100                 105
```

<210> 95
<211> 108
<212> PRT
<213> *Homo sapiens*
<400> 95

```
Asp Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Asn
            20                  25                  30
Tyr Leu Ala Trp Tyr Gln Gln Lys Pro Gly Gln Ala Pro Arg Leu Leu
        35                  40                  45
Ile Tyr Tyr Ala Ser Arg Arg Ala Thr Gly Val Pro Ala Arg Phe Ser
    50                  55                  60
Gly Ser Gly Ser Gly Thr Asp Phe Thr Leu Thr Ile Ser Ser Leu Glu
65                  70                  75                  80
Pro Glu Asp Phe Ala Val Tyr Tyr Cys Gln Gln Phe Ile Thr Tyr Leu
                85                  90                  95
Pro Thr Phe Gly Gln Gly Thr Lys Val Glu Ile Lys
            100                 105
```

<210> 96
<211> 108
<212> PRT
<213> *Homo sapiens*
<400> 96

```
Asp Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Asn
            20                  25                  30
Tyr Leu Ala Trp Tyr Gln Gln Lys Pro Gly Gln Ala Pro Arg Leu Leu
        35                  40                  45
Ile Tyr Tyr Ala Ser Arg Arg Ala Thr Gly Val Pro Ala Arg Phe Ser
    50                  55                  60
Gly Ser Gly Ser Gly Thr Asp Phe Thr Leu Thr Ile Ser Ser Leu Glu
65                  70                  75                  80
```

-continued

Pro Glu Asp Phe Ala Val Tyr Tyr Cys Gln Gln Asp Ala Leu Ser Pro
                85                  90                  95
Phe Thr Phe Gly Gln Gly Thr Lys Val Glu Ile Lys
            100                 105

<210> 97
<211> 108
<212> PRT
<213> Homo sapiens
<400> 97
Asp Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Asn
            20                  25                  30
Tyr Leu Ala Trp Tyr Gln Gln Lys Pro Gly Gln Ala Pro Arg Leu Leu
        35                  40                  45
Ile Tyr Tyr Ala Ser Arg Arg Ala Thr Gly Val Pro Ala Arg Phe Ser
    50                  55                  60
Gly Ser Gly Ser Gly Thr Asp Phe Thr Leu Thr Ile Ser Ser Leu Glu
65                  70                  75                  80
Pro Glu Asp Phe Ala Val Tyr Tyr Cys Gln Gln Asp Arg Gly Thr Pro
                85                  90                  95
Phe Thr Phe Gly Gln Gly Thr Lys Val Glu Ile Lys
            100                 105

<210> 98
<211> 108
<212> PRT
<213> Homo sapiens
<400> 98
Asp Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Asn
            20                  25                  30
Tyr Leu Ala Trp Tyr Gln Gln Lys Pro Gly Gln Ala Pro Arg Leu Leu
        35                  40                  45
Ile Tyr Tyr Ala Ser Arg Arg Ala Thr Gly Val Pro Ala Arg Phe Ser
    50                  55                  60
Gly Ser Gly Ser Gly Thr Asp Phe Thr Leu Thr Ile Ser Ser Leu Glu
65                  70                  75                  80
Pro Glu Asp Phe Ala Val Tyr Tyr Cys Gln Gln Ser Leu Asn Ile Pro
                85                  90                  95
Phe Thr Phe Gly Gln Gly Thr Lys Val Glu Ile Lys
            100                 105

<210> 99
<211> 116
<212> PRT
<213> Homo sapiens
<400> 99
Gln Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Thr Asn Tyr
            20                  25                  30
Trp Ile Ser Trp Val Arg Gln Ala Pro Gly Lys Gly Leu Glu Trp Met
        35                  40                  45
Gly Trp Ile Arg Pro Gly Asp Ser Asp Thr Arg Tyr Ser Pro Ser Phe
    50                  55                  60
Glu Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg His Tyr Tyr Gly Met Asp Tyr Trp Gly Gln Gly Thr Leu Val
            100                 105                 110
Thr Val Ser Ser
        115

<210> 100
<211> 110
<212> PRT
<213> Homo sapiens
<400> 100
Asp Ile Val Leu Thr Gln Pro Pro Ser Val Ser Gly Ala Pro Gly Gln
1               5                   10                  15
Arg Val Thr Ile Ser Cys Ser Gly Ser Ser Ser Asn Ile Gly Ser Tyr
            20                  25                  30
Tyr Val Asn Trp Tyr Gln Gln Leu Pro Gly Thr Ala Pro Lys Leu Leu
        35                  40                  45
Ile Tyr Gly Asn Thr His Arg Pro Ser Gly Val Pro Asp Arg Phe Ser
    50                  55                  60

```
Gly Ser Lys Ser Gly Thr Ser Ala Ser Leu Ala Ile Thr Gly Leu Gln
 65                 70                  75                  80
Ser Glu Asp Glu Ala Asp Tyr Tyr Cys Gln Thr Tyr Ala Ser Leu Gly
                 85                  90                  95
Pro Gly Glu Val Phe Gly Gly Thr Lys Leu Thr Val Leu
            100                 105                 110

<210> 101
<211> 121
<213> Homo sapiens
<400> 101
Gln Val Gln Leu Val Glu Ser Gly Gly Gly Leu Val Gln Pro Gly Gly
  1               5                  10                  15
Ser Leu Arg Leu Ser Cys Ala Ala Ser Gly Phe Thr Phe Ser Ser Tyr
                 20                  25                  30
Trp Ile Thr Trp Val Arg Gln Ala Pro Gly Lys Gly Leu Glu Trp Val
             35                  40                  45
Ser Tyr Ile Ser Ser Ser Gly Ser Ser Thr Tyr Tyr Ala Asp Ser Val
         50                  55                  60
Lys Gly Arg Phe Thr Ile Ser Arg Asp Asn Ser Lys Asn Thr Leu Tyr
 65                 70                  75                  80
Leu Gln Met Asn Ser Leu Arg Ala Glu Asp Thr Ala Val Tyr Tyr Cys
                 85                  90                  95
Ala Arg Gly Thr Phe Trp Ser Phe Gly Asn Tyr Phe Ala Asn Trp Gly
            100                 105                 110
Gln Gly Thr Leu Val Thr Val Ser Ser
        115                 120

<210> 102
<211> 107
<212> PRT
<213> Homo sapiens
<400> 102
Asp Ile Val Leu Thr Gln Ser Pro Ala Thr Leu Ser Leu Ser Pro Gly
  1               5                  10                  15
Glu Arg Ala Thr Leu Ser Cys Arg Ala Ser Gln Ser Ile Phe Tyr Asn
                 20                  25                  30
Leu Ala Trp Tyr Gln Gln Lys Pro Gly Gln Ala Pro Arg Leu Leu Ile
             35                  40                  45
Tyr Gly Ala Ser Asn Arg Ala Thr Gly Val Pro Ala Arg Phe Ser Gly
         50                  55                  60
Ser Gly Ser Gly Thr Asp Phe Thr Leu Thr Ile Ser Ser Leu Glu Pro
 65                 70                  75                  80
Glu Asp Phe Ala Thr Tyr Tyr Cys Gln Gln Tyr Ser Ser Glu Pro Val
                 85                  90                  95
Thr Phe Gly Gln Gly Thr Lys Val Glu Ile Lys
            100                 105

<210> 103
<211> 117
<212> PRT
<213> Homo sapiens
<400> 103
Gln Val Gln Leu Val Gln Ser Gly Ala Glu Val Lys Lys Pro Gly Glu
  1               5                  10                  15
Ser Leu Lys Ile Ser Cys Lys Gly Ser Gly Tyr Ser Phe Ser Asn Tyr
                 20                  25                  30
Trp Ile Gly Trp Val Arg Gln Met Pro Gly Lys Gly Leu Glu Trp Met
             35                  40                  45
Gly Ile Ile Asp Pro Ser Asn Ser Tyr Thr Asn Tyr Ser Pro Ser Phe
         50                  55                  60
Gln Gly Gln Val Thr Ile Ser Ala Asp Lys Ser Ile Ser Thr Ala Tyr
 65                 70                  75                  80
Leu Gln Trp Ser Ser Leu Lys Ala Ser Asp Thr Ala Met Tyr Tyr Cys
                 85                  90                  95
Ala Arg Trp Tyr Tyr Lys Pro Phe Asp Val Trp Gly Gln Gly Thr Leu
            100                 105                 110
Val Thr Val Ser Ser
        115

<210> 104
<211> 117
<212> PRT
<213> Homo sapiens
<400> 104
Gln Val Gln Leu Val Gln Ser Gly Ala Glu Val Lys Lys Pro Gly Glu
  1               5                  10                  15
Ser Leu Lys Ile Ser Cys Lys Gly Ser Gly Tyr Ser Phe Ser Asn Tyr
                 20                  25                  30
Trp Ile Gly Trp Val Arg Gln Met Pro Gly Lys Gly Leu Glu Trp Met
             35                  40                  45
```

```
                                            -continued
Gly Ile Ile Asp Pro Ser Asn Ser Tyr Thr Asp Tyr Ser Pro Ser Phe
        50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Trp Tyr Tyr Lys Pro Phe Asp Val Trp Gly Gln Gly Thr Leu
                100                 105                 110
Val Thr Val Ser Ser
            115

<210> 105
<211> 117
<212> PRT
<213> Homo sapiens
<400> 105
Glu Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Ser Asn Tyr
                20                  25                  30
Trp Ile Gly Trp Val Arg Gln Met Pro Gly Lys Gly Leu Glu Trp Met
            35                  40                  45
Gly Ile Ile Asp Pro Ser Asn Ser Tyr Thr Arg Tyr Ser Pro Ser Phe
        50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Trp Tyr Tyr Lys Pro Phe Asp Val Trp Gly Gln Gly Thr Leu
                100                 105                 110
Val Thr Val Ser Ser
            115

<210> 106
<211> 117
<212> PRT
<213> Homo sapiens
<400> 106
Glu Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Ser Asn Tyr
                20                  25                  30
Trp Ile Gly Trp Val Arg Gln Met Pro Gly Lys Gly Leu Glu Trp Met
            35                  40                  45
Gly Ile Ile Asp Pro Ser Asn Ser Tyr Thr Arg Tyr Ser Pro Ser Phe
        50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Trp Tyr Tyr Lys Pro Phe Asp Val Trp Gly Gln Gly Thr Leu
                100                 105                 110
Val Thr Val Ser Ser
            115

<210> 107
<211> 117
<212> PRT
<213> Homo sapiens
<400> 107
Gln Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Ser Asn Tyr
                20                  25                  30
Trp Ile Gly Trp Val Arg Gln Met Pro Gly Lys Gly Leu Glu Trp Met
            35                  40                  45
Gly Ile Ile Asp Pro Val Ser Ser Trp Thr Lys Tyr Ser Pro Ser Phe
        50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Trp Tyr Tyr Lys Pro Phe Asp Val Trp Gly Gln Gly Thr Leu
                100                 105                 110
Val Thr Val Ser Ser
            115

<210> 108
<211> 117
<212> PRT
<213> Homo sapiens
```

```
<400> 108
Gln Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Ser Asn Tyr
            20                  25                  30
Trp Ile Gly Trp Val Arg Gln Met Pro Gly Lys Gly Leu Glu Trp Met
        35                  40                  45
Gly Ile Ile Ser Pro Ser Gly Ser Thr Thr Trp Tyr Ser Pro Ser Phe
    50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Trp Tyr Tyr Lys Pro Phe Asp Val Trp Gly Gln Gly Thr Leu
            100                 105                 110
Val Thr Val Ser Ser
        115

<210> 109
<211> 117
<212> PRT
<213> Homo sapiens
<400> 109
Gln Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Ser Asn Tyr
            20                  25                  30
Trp Ile Gly Trp Val Arg Gln Met Pro Gly Lys Gly Leu Glu Trp Met
        35                  40                  45
Gly Phe Ile Ser Pro Asp Gly Ser His Thr Trp Tyr Ser Pro Ser Phe
    50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Trp Tyr Tyr Lys Pro Phe Asp Val Trp Gly Gln Gly Thr Leu
            100                 105                 110
Val Thr Val Ser Ser
        115

<210> 110
<211> 117
<212> PRT
<213> Homo sapiens
<400> 110
Gln Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Ser Asn Tyr
            20                  25                  30
Trp Ile Gly Trp Val Arg Gln Met Pro Gly Lys Gly Leu Glu Trp Met
        35                  40                  45
Gly Ile Ile Ser Pro Thr Gly Ser Val Thr Trp Tyr Ser Pro Ser Phe
    50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Trp Tyr Tyr Lys Pro Phe Asp Val Trp Gly Gln Gly Thr Leu
            100                 105                 110
Val Thr Val Ser Ser
        115

<210> 111
<211> 117
<212> PRT
<213> Homo sapiens
<400> 111
Gln Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Ser Asn Tyr
            20                  25                  30
Trp Ile Gly Trp Val Arg Gln Met Pro Gly Lys Gly Leu Glu Trp Met
        35                  40                  45
Gly Ile Ile Ser Pro Thr Gly Ser Ser Thr Trp Tyr Ser Pro Ser Phe
    50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Trp Tyr Tyr Lys Pro Phe Asp Val Trp Gly Gln Gly Thr Leu
            100                 105                 110
```

```
Val Thr Val Ser Ser
        115

<210> 112
<211> 117
<212> PRT
<213> Homo sapiens
<400> 112
Gln Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Ser Asn Tyr
            20                  25                  30
Trp Ile Gly Trp Val Arg Gln Met Pro Gly Lys Gly Leu Glu Trp Met
        35                  40                  45
Gly Ile Ile Ser Pro Thr Gly Ser Ala Thr Trp Tyr Ser Pro Ser Phe
    50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Trp Tyr Tyr Lys Pro Phe Asp Val Trp Gly Gln Gly Thr Leu
            100                 105                 110
Val Thr Val Ser Ser
        115

<210> 113
<211> 109
<212> PRT
<213> Homo sapiens
<400> 113
Asp Ile Val Leu Thr Gln Pro Pro Ser Val Ser Gly Ala Pro Gly Gln
1               5                   10                  15
Arg Val Thr Ile Ser Cys Thr Gly Ser Ser Ser Asn Ile Gly Ser Gly
            20                  25                  30
Tyr Asp Val His Trp Tyr Gln Gln Leu Pro Gly Thr Ala Pro Lys Leu
        35                  40                  45
Leu Ile Tyr Gly Asn Ser Lys Arg Pro Ser Gly Val Pro Asp Arg Phe
    50                  55                  60
Ser Gly Ser Lys Ser Gly Thr Ser Ala Ser Leu Ala Ile Thr Gly Leu
65                  70                  75                  80
Gln Ser Glu Asp Glu Ala Asp Tyr Tyr Cys Ser Ser Trp Thr Pro Ser
                85                  90                  95
Ser Val Val Phe Gly Gly Gly Thr Lys Leu Thr Val Leu
            100                 105

<210> 114
<211> 111
<212> PRT
<213> Homo sapiens
<400> 114
Asp Ile Val Leu Thr Gln Pro Pro Ser Val Ser Gly Ala Pro Gly Gln
1               5                   10                  15
Arg Val Thr Ile Ser Cys Thr Gly Ser Ser Ser Asn Ile Gly Ser Gly
            20                  25                  30
Tyr Asp Val His Trp Tyr Gln Gln Leu Pro Gly Thr Ala Pro Lys Leu
        35                  40                  45
Leu Ile Tyr Gly Asn Ser Lys Arg Pro Ser Gly Val Pro Asp Arg Phe
    50                  55                  60
Ser Gly Ser Lys Ser Gly Thr Ser Ala Ser Leu Ala Ile Thr Gly Leu
65                  70                  75                  80
Gln Ser Glu Asp Glu Ala Asp Tyr Tyr Cys Ser Ser Trp Thr Asp Thr
                85                  90                  95
Pro Asn Met Ile Val Phe Gly Gly Gly Thr Lys Leu Thr Val Leu
            100                 105                 110

<210> 115
<211> 111
<212> PRT
<213> Homo sapiens
<400> 115
Asp Ile Val Leu Thr Gln Pro Pro Ser Val Ser Gly Ala Pro Gly Gln
1               5                   10                  15
Arg Val Thr Ile Ser Cys Thr Gly Ser Ser Ser Asn Ile Gly Ser Gly
            20                  25                  30
Tyr Asp Val His Trp Tyr Gln Gln Leu Pro Gly Thr Ala Pro Lys Leu
        35                  40                  45
Leu Ile Tyr Gly Asn Ser Lys Arg Pro Ser Gly Val Pro Asp Arg Phe
    50                  55                  60
Ser Gly Ser Lys Ser Gly Thr Ser Ala Ser Leu Ala Ile Thr Gly Leu
65                  70                  75                  80
```

```
Gln Ser Glu Asp Glu Ala Asp Tyr Tyr Cys Ala Ser Trp Thr Asp Gly
                85                  90                  95
Leu Ser Leu Val Val Phe Gly Gly Gly Thr Lys Leu Thr Val Leu
            100                 105                 110

<210> 116
<211> 111
<212> PRT
<213> Homo sapiens
<400> 116
Gln Ser Val Leu Thr Gln Pro Pro Ser Val Ser Gly Ala Pro Gly Gln
1               5                   10                  15
Arg Val Thr Ile Ser Cys Thr Gly Ser Ser Ser Asn Ile Gly Ser Gly
            20                  25                  30
Tyr Asp Val His Trp Tyr Gln Gln Leu Pro Gly Thr Ala Pro Lys Leu
        35                  40                  45
Leu Ile Tyr Gly Asn Ser Lys Arg Pro Ser Gly Val Pro Asp Arg Phe
    50                  55                  60
Ser Gly Ser Lys Ser Gly Thr Ser Ala Ser Leu Ala Ile Thr Gly Leu
65                  70                  75                  80
Gln Ser Glu Asp Glu Ala Asp Tyr Tyr Cys Ala Ser Trp Thr Asp Gly
                85                  90                  95
Leu Ser Leu Val Val Phe Gly Gly Gly Thr Lys Leu Thr Val Leu
            100                 105                 110

<210> 117
<211> 121
<212> PRT
<213> Homo sapiens
<400> 117
Gln Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Phe
            20                  25                  30
Gly Met Ser Trp Val Arg Gln Ala Pro Gly Lys Gly Leu Glu Trp Val
        35                  40                  45
Ser Asn Ile Ser Ser Ser Gly Ser Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Tyr Trp Gly Thr Pro Tyr Leu Met Gln Phe Asp Asn Trp Gly
            100                 105                 110
Gln Gly Thr Leu Val Thr Val Ser Ser
        115                 120

<210> 118
<211> 123
<212> PRT
<213> Homo sapiens
<400> 118
Gln Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Phe
            20                  25                  30
Gly Met Ser Trp Val Arg Gln Ala Pro Gly Lys Gly Leu Glu Trp Val
        35                  40                  45
Ser Asn Ile Glu His Lys Phe Met Gly Tyr Thr Thr Tyr Tyr Ala Ala
    50                  55                  60
Gly Val Lys Gly Arg Phe Thr Ile Ser Arg Asp Asn Ser Lys Asn Thr
65                  70                  75                  80
Leu Tyr Leu Gln Met Asn Ser Leu Arg Ala Glu Asp Thr Ala Val Tyr
                85                  90                  95
Tyr Cys Ala Arg Tyr Trp Gly Thr Pro Tyr Leu Met Gln Phe Asp Asn
            100                 105                 110
Trp Gly Gln Gly Thr Leu Val Thr Val Ser Ser
        115                 120

<210> 119
<211> 123
<212> PRT
<213> Homo sapiens
<400> 119
Gln Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Phe
            20                  25                  30
Gly Met Ser Trp Val Arg Gln Ala Pro Gly Lys Gly Leu Glu Trp Val
        35                  40                  45
```

```
Ser Ser Ile Glu His Lys Tyr Thr Gly Tyr Thr Tyr Tyr Ala Ala
        50                  55                  60
Pro Val Lys Gly Arg Phe Thr Ile Ser Arg Asp Asn Ser Lys Asn Thr
 65                  70                  75                  80
Leu Tyr Leu Gln Met Asn Ser Leu Arg Ala Glu Asp Thr Ala Val Tyr
                    85                  90                  95
Tyr Cys Ala Arg Tyr Trp Gly Thr Pro Tyr Leu Met Gln Phe Asp Asn
                100                 105                 110
Trp Gly Gln Gly Thr Leu Val Thr Val Ser Ser
            115                 120
```

<210> 120
<211> 123
<212> PRT
<213> Homo sapiens

<400> 120
```
Gln Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Phe
                20                  25                  30
Gly Met Ser Trp Val Arg Gln Ala Pro Gly Lys Gly Leu Glu Trp Val
            35                  40                  45
Ser Asn Ile Glu His Lys Tyr Thr Ser Tyr Thr Thr Tyr Tyr Ala Ala
        50                  55                  60
Ser Val Lys Gly Arg Phe Thr Ile Ser Arg Asp Asn Ser Lys Asn Thr
 65                  70                  75                  80
Leu Tyr Leu Gln Met Asn Ser Leu Arg Ala Glu Asp Thr Ala Val Tyr
                    85                  90                  95
Tyr Cys Ala Arg Tyr Trp Gly Thr Pro Tyr Leu Met Gln Phe Asp Asn
                100                 105                 110
Trp Gly Gln Gly Thr Leu Val Thr Val Ser Ser
            115                 120
```

<210> 121
<211> 123
<212> PRT
<213> Homo sapiens

<400> 121
```
Gln Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Phe
                20                  25                  30
Gly Met Ser Trp Val Arg Gln Ala Pro Gly Lys Gly Leu Glu Trp Val
            35                  40                  45
Ser Asn Ile Glu His Lys Tyr Leu Asn Tyr Ala Thr Tyr Tyr Ala Ala
        50                  55                  60
Ser Val Lys Gly Arg Phe Thr Ile Ser Arg Asp Asn Ser Lys Asn Thr
 65                  70                  75                  80
Leu Tyr Leu Gln Met Asn Ser Leu Arg Ala Glu Asp Thr Ala Val Tyr
                    85                  90                  95
Tyr Cys Ala Arg Tyr Trp Gly Thr Pro Tyr Leu Met Gln Phe Asp Asn
                100                 105                 110
Trp Gly Gln Gly Thr Leu Val Thr Val Ser Ser
            115                 120
```

<210> 122
<211> 123
<212> PRT
<213> Homo sapiens

<400> 122
```
Gln Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Phe
                20                  25                  30
Gly Met Ser Trp Val Arg Gln Ala Pro Gly Lys Gly Leu Glu Trp Val
            35                  40                  45
Ser Asn Ile Glu His Lys Tyr Leu Gly Tyr Ala Thr Val Tyr Ala Ala
        50                  55                  60
Ser Val Lys Gly Arg Phe Thr Ile Ser Arg Asp Asn Ser Lys Asn Thr
 65                  70                  75                  80
Leu Tyr Leu Gln Met Asn Ser Leu Arg Ala Glu Asp Thr Ala Val Tyr
                    85                  90                  95
Tyr Cys Ala Arg Tyr Trp Gly Thr Pro Tyr Leu Met Gln Phe Asp Asn
                100                 105                 110
Trp Gly Gln Gly Thr Leu Val Thr Val Ser Ser
            115                 120
```

<210> 123
<211> 123
<212> PRT
<213> Homo sapiens

-continued

<400> 123

| Gln | Val | Gln | Leu | Val | Glu | Ser | Gly | Gly | Gly | Leu | Val | Gln | Pro | Gly | Gly |
|1|||||5||||10||||15||
| Ser | Leu | Arg | Leu | Ser | Cys | Ala | Ala | Ser | Gly | Phe | Thr | Phe | Ser | Ser | Phe |
|||||20||||25||||30|||
| Gly | Met | Ser | Trp | Val | Arg | Gln | Ala | Pro | Gly | Lys | Gly | Leu | Glu | Trp | Val |
|||35||||||40||||45|||
| Ser | Ser | Ile | Glu | His | Lys | Tyr | Leu | Ser | Tyr | Ala | Thr | Tyr | Tyr | Ala | Ala |
|50||||||55||||||60|||
| Gly | Val | Lys | Gly | Arg | Phe | Thr | Ile | Ser | Arg | Asp | Asn | Ser | Lys | Asn | Thr |
|65||||||70||||75||||80|
| Leu | Tyr | Leu | Gln | Met | Asn | Ser | Leu | Arg | Ala | Glu | Asp | Thr | Ala | Val | Tyr |
|||||85||||||90||||95|
| Tyr | Cys | Ala | Arg | Tyr | Trp | Gly | Thr | Pro | Tyr | Leu | Met | Gln | Phe | Asp | Asn |
||||100|||||105||||110|||
| Trp | Gly | Gln | Gly | Thr | Leu | Val | Thr | Val | Ser | Ser |
|||||115||||120|||

<210> 124
<211> 123
<212> PRT
<213> Homo sapiens
<400> 124

| Gln | Val | Gln | Leu | Val | Glu | Ser | Gly | Gly | Gly | Leu | Val | Gln | Pro | Gly | Gly |
|1|||||5||||10||||15||
| Ser | Leu | Arg | Leu | Ser | Cys | Ala | Ala | Ser | Gly | Phe | Thr | Phe | Ser | Ser | Phe |
|||||20||||25||||30|||
| Gly | Met | Ser | Trp | Val | Arg | Gln | Ala | Pro | Gly | Lys | Gly | Leu | Glu | Trp | Val |
|||35||||||40||||45|||
| Ser | Ser | Ile | Glu | His | Lys | Tyr | Leu | Ser | Tyr | Thr | Thr | Phe | Tyr | Ala | Ala |
|50||||||55||||||60|||
| Ser | Val | Lys | Gly | Arg | Phe | Thr | Ile | Ser | Arg | Asp | Asn | Ser | Lys | Asn | Thr |
|65||||||70||||75||||80|
| Leu | Tyr | Leu | Gln | Met | Asn | Ser | Leu | Arg | Ala | Glu | Asp | Thr | Ala | Val | Tyr |
|||||85||||||90||||95|
| Tyr | Cys | Ala | Arg | Tyr | Trp | Gly | Thr | Pro | Tyr | Leu | Met | Gln | Phe | Asp | Asn |
||||100|||||105||||110|||
| Trp | Gly | Gln | Gly | Thr | Leu | Val | Thr | Val | Ser | Ser |
|||||115||||120|||

<210> 125
<211> 123
<212> PRT
<213> Homo sapiens
<400> 125

| Gln | Val | Gln | Leu | Val | Glu | Ser | Gly | Gly | Gly | Leu | Val | Gln | Pro | Gly | Gly |
|1|||||5||||10||||15||
| Ser | Leu | Arg | Leu | Ser | Cys | Ala | Ala | Ser | Gly | Phe | Thr | Phe | Ser | Ser | Phe |
|||||20||||25||||30|||
| Gly | Met | Ser | Trp | Val | Arg | Gln | Ala | Pro | Gly | Lys | Gly | Leu | Glu | Trp | Val |
|||35||||||40||||45|||
| Ser | Gly | Ile | Glu | His | Lys | Tyr | Leu | Ser | Tyr | Thr | Thr | His | Tyr | Ala | Ala |
|50||||||55||||||60|||
| Ser | Val | Lys | Gly | Arg | Phe | Thr | Ile | Ser | Arg | Asp | Asn | Ser | Lys | Asn | Thr |
|65||||||70||||75||||80|
| Leu | Tyr | Leu | Gln | Met | Asn | Ser | Leu | Arg | Ala | Glu | Asp | Thr | Ala | Val | Tyr |
|||||85||||||90||||95|
| Tyr | Cys | Ala | Arg | Tyr | Trp | Gly | Thr | Pro | Tyr | Leu | Met | Gln | Phe | Asp | Asn |
||||100|||||105||||110|||
| Trp | Gly | Gln | Gly | Thr | Leu | Val | Thr | Val | Ser | Ser |
|||||115||||120|||

<210> 126
<211> 123
<212> PRT
<213> Homo sapiens
<400> 126

| Gln | Val | Gln | Leu | Val | Glu | Ser | Gly | Gly | Gly | Leu | Val | Gln | Pro | Gly | Gly |
|1|||||5||||10||||15||
| Ser | Leu | Arg | Leu | Ser | Cys | Ala | Ala | Ser | Gly | Phe | Thr | Phe | Ser | Ser | Phe |
|||||20||||25||||30|||
| Gly | Met | Ser | Trp | Val | Arg | Gln | Ala | Pro | Gly | Lys | Gly | Leu | Glu | Trp | Val |
|||35||||||40||||45|||
| Ser | Gln | Ile | Glu | His | Lys | Tyr | Leu | Ser | Tyr | Thr | Thr | Leu | Tyr | Ala | Ala |
|50||||||55||||||60|||
| Ser | Val | Lys | Gly | Arg | Phe | Thr | Ile | Ser | Arg | Asp | Asn | Ser | Lys | Asn | Thr |
|65||||||70||||75||||80|
| Leu | Tyr | Leu | Gln | Met | Asn | Ser | Leu | Arg | Ala | Glu | Asp | Thr | Ala | Val | Tyr |
|||||85||||||90||||95|
| Tyr | Cys | Ala | Arg | Tyr | Trp | Gly | Thr | Pro | Tyr | Leu | Met | Gln | Phe | Asp | Asn |
||||100|||||105||||110|||

```
Trp Gly Gln Gly Thr Leu Val Thr Val Ser Ser
        115                 120

<210> 127
<211> 123
<212> PRT
<213> Homo sapiens
<400> 127
Gln Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Phe
            20                  25                  30
Gly Met Ser Trp Val Arg Gln Ala Pro Gly Lys Gly Leu Glu Trp Val
        35                  40                  45
Ser Gly Ile Glu His Lys Tyr Leu Ser Tyr Ala Thr Leu Tyr Ala Ala
    50                  55                  60
Ser Val Lys Gly Arg Phe Thr Ile Ser Arg Asp Asn Ser Lys Asn Thr
65                  70                  75                  80
Leu Tyr Leu Gln Met Asn Ser Leu Arg Ala Glu Asp Thr Ala Val Tyr
                85                  90                  95
Tyr Cys Ala Arg Tyr Trp Gly Thr Pro Tyr Leu Met Gln Phe Asp Asn
            100                 105                 110
Trp Gly Gln Gly Thr Leu Val Thr Val Ser Ser
        115                 120

<210> 128
<211> 111
<212> PRT
<213> Homo sapiens
<400> 128
Asp Ile Ala Leu Thr Gln Pro Ala Ser Val Ser Gly Ser Pro Gly Gln
 1               5                  10                  15
Ser Ile Thr Ile Ser Cys Thr Gly Thr Ser Ser Asp Val Gly Gly Tyr
            20                  25                  30
Asn Ser Val Ser Trp Tyr Gln Gln His Pro Gly Lys Ala Pro Lys Leu
        35                  40                  45
Met Ile Tyr Ser Val Ser Ser Arg Pro Ser Gly Val Ser Asn Arg Phe
    50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Ser Ser Tyr Asp Thr Asn
                85                  90                  95
Lys Pro Leu Val Val Phe Gly Gly Gly Thr Lys Leu Thr Val Leu
            100                 105                 110

<210> 129
<211> 111
<212> PRT
<213> Homo sapiens
<400> 129
Asp Ile Ala Leu Thr Gln Pro Ala Ser Val Ser Gly Ser Pro Gly Gln
 1               5                  10                  15
Ser Ile Thr Ile Ser Cys Thr Gly Thr Ser Ser Asp Val Gly Gly Tyr
            20                  25                  30
Asn Ser Val Ser Trp Tyr Gln Gln His Pro Gly Lys Ala Pro Lys Leu
        35                  40                  45
Met Ile Tyr Ser Val Ser Ser Arg Pro Ser Gly Val Ser Asn Arg Phe
    50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Ser Ser Tyr Tyr Phe Tyr
                85                  90                  95
Leu Gln Arg Ile Val Phe Gly Gly Gly Thr Lys Leu Thr Val Leu
            100                 105                 110

<210> 130
<211> 111
<212> PRT
<213> Homo sapiens
<400> 130
Asp Ile Ala Leu Thr Gln Pro Ala Ser Val Ser Gly Ser Pro Gly Gln
 1               5                  10                  15
Ser Ile Thr Ile Ser Cys Thr Gly Thr Ser Ser Asp Val Gly Gly Tyr
            20                  25                  30
Asn Ser Val Ser Trp Tyr Gln Gln His Pro Gly Lys Ala Pro Lys Leu
        35                  40                  45
Met Ile Tyr Ser Val Ser Ser Arg Pro Ser Gly Val Ser Asn Arg Phe
    50                  55                  60
Ser Gly Ser Lys Ser Gly Asn Thr Ala Ser Leu Thr Ile Ser Gly Leu
65                  70                  75                  80
```

```
Gln Ala Glu Asp Glu Ala Asp Tyr Tyr Cys Gln Thr Tyr Phe Ser
                85                  90                  95
Tyr Ser Gly Pro Val Phe Gly Gly Gly Thr Lys Leu Thr Val Leu
            100                 105                 110
```

<210> 131
<211> 111
<212> PRT
<213> Homo sapiens
<400> 131

```
Asp Ile Ala Leu Thr Gln Pro Ala Ser Val Ser Gly Ser Pro Gly Gln
 1               5                  10                  15
Ser Ile Thr Ile Ser Cys Thr Gly Thr Ser Ser Asp Val Gly Gly Tyr
                20                  25                  30
Asn Ser Val Ser Trp Tyr Gln Gln His Pro Gly Lys Ala Pro Lys Leu
            35                  40                  45
Met Ile Tyr Ser Val Ser Arg Pro Ser Gly Val Ser Asn Arg Phe
        50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Gly Ser Tyr Asp Val Tyr
                85                  90                  95
Gly Arg Phe Tyr Val Phe Gly Gly Gly Thr Lys Leu Thr Val Leu
            100                 105                 110
```

<210> 132
<211> 111
<212> PRT
<213> Homo sapiens
<400> 132

```
Asp Ile Ala Leu Thr Gln Pro Ala Ser Val Ser Gly Ser Pro Gly Gln
 1               5                  10                  15
Ser Ile Thr Ile Ser Cys Thr Gly Thr Ser Ser Asp Val Gly Gly Tyr
                20                  25                  30
Asn Ser Val Ser Trp Tyr Gln Gln His Pro Gly Lys Ala Pro Lys Leu
            35                  40                  45
Met Ile Tyr Ser Val Ser Arg Pro Ser Gly Val Ser Asn Arg Phe
        50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Gly Ser Trp Asp Pro Ile
                85                  90                  95
Phe Ser Tyr Glu Val Phe Gly Gly Gly Thr Lys Leu Thr Val Leu
            100                 105                 110
```

<210> 133
<211> 381
<212> DNA
<213> Homo sapiens
<400> 133

```
caggtgcagc tggtgcagtc tggggctgag gtgaagaagc ctgggtcctc ggtgaaggtc   60
tcctgcaagg cttctggagg cacccttcag agcaactaca tcagctgggt gcgacaggcc  120
cctggacaag gccttgagtg gatggggatc agccctggca ccggtatcaa cgcatactac  180
gcacagaagt tccagggcag agtcacgatt accgcggacg aatccacgag cacagcctac  240
atggagctga gcagcctgag atctgaggac acggccgtgt attactgtgc gagaagcaag  300
aagggcatgt acggcggctg gacctacccc ctgatgatgt tcgacctgtg gggccagggc  360
accctggtga ccgtgagcag c                                            381
```

<210> 134
<211> 381
<212> DNA
<213> Homo sapiens
<400> 134

```
caggtgcagc tggtgcagag cggcgccgag gtgaagaagc ccggcagcag cgtgaaggtg   60
agctgcaagg ccagcggcgg cacccttcag agcaactaca tcagctgggt gcgccaggcc  120
cccggccagg gcctggagtg gatgggcatc agccccggca ccggcatcaa cgcctactac  180
gcccagaagt tccagggccg cgtgaccatc accgccgacg agagcaccag caccgcctac  240
atggagctga gcagcctgcg cagcgaggac accgccgtgt actactgcgc ccgcagcaag  300
aagggcatgt acggcggctg gacctacccc ctgatgatgt tcgacctgtg gggccagggc  360
accctggtga ccgtgagcag c                                            381
```

<210> 135
<211> 381
<212> DNA
<213> Homo sapiens
<400> 135

```
caggtgcaat tggttcagtc tggcgcggaa gtgaaaaaac cgggcagcag cgtgaaagtg   60
agctgcaaag cctccggagg cactttttct tctaattata tttcttgggt gcgccaagcc  120
cctgggcagg gtctcgagtg gatgggcatt tctcctggta ctggtattaa tgcttattat  180
gctcagaagt tccagggtcg ggtgaccatt accgcggatg aaagcaccag caccgcgtat  240
atggaactga gcagcctgcg tagcgaagat acggccgtgt attattgcgc gcgttctaag  300
```

-continued
```
aagggtatgt atggtggttg gacttatcct cttatgatgt ttgatctttg gggccaaggc    360
accctggtga cggttagctc a                                               381

<210> 136
<211> 324
<212> DNA
<213> Homo sapiens
<400> 136
gagatcgtgc tgacccagag ccccgccacc ctgagcctga gccccggcga gcgcgccacc     60
ctgagctgcc gcgccagcca gagcgtgagc agcaactacc tggcctggta ccagcagaaa    120
cccggccagg ccccccgcct gctgatctac tacgccagcc gccgcgccac cggcgtgccc    180
gcccgcttca gcggcagcgg cagcggcacc gacttcaccc tgaccatcag cagcctggag    240
cccgaggact tcgccgtgta ctactgccag cagaccagca caccccctt caccttcggc     300
cagggcacca aggggagat caag                                            324

<210> 137
<211> 324
<212> DNA
<213> Homo sapiens
<400> 137
gaaattgtgt tgacacagtc tccagccacc ctgtctttgt ctccagggga aagagccacc     60
ctctcctgca gggccagtca gagtgttagc agcaactact tagcctggta ccaacagaaa    120
cctggccagg ctcccaggct cctcatctat tacgcatccc gcagggccac tggcgtgcca    180
gccaggttca gtggcagtgg gtctgggaca gacttcactc tcaccatcag cagcctagag    240
cctgaagatt ttgcagttta ttactgtcag cagacttcta atactccttt tacctttggc    300
cagggtacga aagttgaaat taaa                                           324

<210> 138
<211> 324
<212> DNA
<213> Homo sapiens
<400> 138
gagatcgtgc tgacccagag cccggcgacc ctgagcctgt ctccgggcga acgtgcgacc     60
ctgagctgca gagcgagcca gtctgtttct tctaattatc tggcttggta ccagcagaaa    120
ccaggtcaag caccgcgtct attaatttat tatgcttctc gtcagcgaac tggggtcccg    180
gcgcgtttta gcggctctgg atccggcacg gatttacccc tgaccattag cagcctggaa    240
cctgaagact ttgcggtgta ttattgccag cagacttcta atactccttt tacctttggc    300
cagggtacga aagttgaaat taaa                                           324

<210> 139
<211> 351
<212> DNA
<213> Homo sapiens
<400> 139
gaggtgcagc tggtgcagtc tggagcagag gtgaaaaagc ccggggagtc tctgaagatc     60
tcctgtaagg gttctggata cagctttagc aactactgga tcggctgggt gcgccagatg    120
cccgggaaag gcctggagtg gatggggatc atcgaccct gcaactctta caccagatac    180
agcccgtcct tccaaggcca ggtcaccatc tcagccgaca gtccatcag caccgcctac    240
ctgcagtgga gcagcctgaa ggcctcggac accgccatgt attactgtgc gagatggtac    300
tacaagccct tcgacgtgtg gggccagggc accctggtga ccgtgagcag c             351

<210> 140
<211> 351
<212> DNA
<213> Homo sapiens
<400> 140
gaggtgcagc tggtgcagag cggcgccgag gtgaagaagc ccggcgagag cctgaagatc     60
agctgcaagg gcagcggcta cagcttcagc aactactgga tcggctgggt gcgccagatg    120
cccggcaagg gcctggagtg gatgggcatc atcgaccca gcaacagcta caccgctac     180
agccccagct ccagggcca ggtgaccatc agcgccgaca gagcatcag caccgcctac    240
ctgcagtgga gcagcctgaa ggccagcgac accgccatgt actactgcgc cgctggtac    300
tacaagccct tcgacgtgtg gggccagggc accctggtga ccgtgagcag c             351

<210> 141
<211> 351
<212> DNA
<213> Homo sapiens
<400> 141
gaggtgcaat tggttcagag cggcgcggaa gtgaaaaaac cggcgaaag cctgaaaatt      60
agctgcaaag gttccggata ttcctttcct aattattgga ttggttgggt gcgccagatg    120
cctgggaagg gtctcgagtg gatgggcatt atcgatccgt ctaatagcta tacccgtat    180
tctccgagct ttcagggcca ggtgaccatt agcgcgata aaagcattag caccgcgtat    240
cttcaatgga gcagcctgaa agcgagcgat acggccatgt attattgcgc gcgttggtat    300
tataagcctt ttgatgtttg gggccaaggc accctggtga cggttagctc a             351

<210> 142
<211> 336
<212> DNA
<213> Homo sapiens
```

```
<400> 142
cagtctgtgc tgacgcagcc gccctcagtg tctggggccc cagggcagag ggtcaccatc    60
tcctgcactg ggagcagctc caacatcggg agcggttatg atgtacactg gtaccagcag   120
cttccaggaa cagcccccaa actcctcatc tatggtaaca gcaagcggcc ctcagggatc   180
cctgaccgat tctctggctc caagtctggc acctcagcct ccctggccat cactgggctc   240
cagagcgagg atgaggctga ttattactgc gccagctgga ccgacggcct gagcctggtg   300
gtgttcggcg gcggcaccaa gctgaccgtg ctgggc                              336

<210> 143
<211> 336
<212> DNA
<213> Homo sapiens
<400> 143
cagagcgtgc tgacccagcc ccccagcgtg agcggcgccc ccggccagcg cgtgaccatc    60
agctgcaccg gcagcagcag caacatcggg agcggctacg acgtgcactg gtaccagcag   120
ctgcccggca ccgcccccaa gctgctgatc tacggcaaca gcaagcgccc cagcggcgtg   180
cccgaccgct tcagcggcag caagagcggc accagcgcca gcctggccat caccggcctc   240
cagagcgagg acgaggccga ctactactgt gccagctgga ccgacggcct gagcctggtg   300
gtgttcggcg gcggcaccaa gctgaccgtg ctgggc                              336

<210> 144
<211> 336
<212> DNA
<213> Homo sapiens
<400> 144
cagagcgtgc tgacccagcc gccttcagtg agtggcgcac caggtcagcg tgtgaccatc    60
tcgtgtacgg gcagcagcag caacattggt tctggttatg atgtgcattg gtaccagcag   120
ttgcccggga cggcgccgaa acttctgatt tatggtaatt ctaagcgtcc ctcaggcgtg   180
ccggatcgtt ttagcggatc caaaagcggc accagcgcga ccttgcgat tacgggcctg    240
caaagcgaag acgaagcgga ttattattgc gcttcttgga ctgatggtct ttctcttgtt   300
gtgtttggcg gcggcacgaa gttaaccgtt cttggc                              336

<210> 145
<211> 189
<212> PRT
<213> Homo sapiens
<400> 145
Met Leu Gly Ser Arg Ala Val Met Leu Leu Leu Leu Pro Trp Thr
1               5                   10                  15
Ala Gln Gly Arg Ala Val Pro Gly Gly Ser Ser Pro Ala Trp Thr Gln
                20                  25                  30
Cys Gln Gln Leu Ser Gln Lys Leu Cys Thr Leu Ala Trp Ser Ala His
            35                  40                  45
Pro Leu Val Gly His Met Asp Leu Arg Glu Glu Gly Asp Glu Glu Thr
        50                  55                  60
Thr Asn Asp Val Pro His Ile Gln Cys Gly Asp Gly Cys Asp Pro Gln
65                  70                  75                  80
Gly Leu Arg Asp Asn Ser Gln Phe Cys Leu Gln Arg Ile His Gln Gly
                85                  90                  95
Leu Ile Phe Tyr Glu Lys Leu Leu Gly Ser Asp Ile Phe Thr Gly Glu
                100                 105                 110
Pro Ser Leu Leu Pro Asp Ser Pro Val Ala Gln Leu His Ala Ser Leu
            115                 120                 125
Leu Gly Leu Ser Gln Leu Leu Gln Pro Glu Gly His His Trp Glu Thr
        130                 135                 140
Gln Gln Ile Pro Ser Leu Ser Pro Ser Gln Pro Trp Gln Arg Leu Leu
145                 150                 155                 160
Leu Arg Phe Lys Ile Leu Arg Ser Leu Gln Ala Phe Val Ala Val Ala
                165                 170                 175
Ala Arg Val Phe Ala His Gly Ala Ala Thr Leu Ser Pro
            180                 185

<210> 146
<211> 19
<212> PRT
<213> Homo sapiens
<400> 146
Asn Ile Glu His Lys Tyr Leu Gly Tyr Ala Thr Ser Tyr Ala Ala Ser
1               5                   10                  15
Val Lys Gly <210> 147
<211> 123
<212> PRT
<213> Homo sapiens
<400> 147
Gln Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Phe
                20                  25                  30
```

```
Gly Met Ser Trp Val Arg Gln Ala Pro Gly Lys Gly Leu Glu Trp Val
            35                  40                  45
Ser Asn Ile Glu His Lys Tyr Leu Gly Tyr Ala Thr Ser Tyr Ala Ala
 50                  55                  60
Ser Val Lys Gly Arg Phe Thr Ile Ser Arg Asp Asn Ser Lys Asn Thr
 65                  70                  75                  80
Leu Tyr Leu Gln Met Asn Ser Leu Arg Ala Glu Asp Thr Ala Val Tyr
                 85                  90                  95
Tyr Cys Ala Arg Tyr Trp Gly Thr Pro Tyr Leu Met Gln Phe Asp Asn
                100                 105                 110
Trp Gly Gln Gly Thr Leu Val Thr Val Ser Ser
            115                 120
```

<210> 148
<211> 12
<212> PRT
<213> Homo sapiens
<400> 148

```
His Gln Gly Leu Ile Phe Tyr Glu Lys Leu Leu
 1               5                  10
```

SEQUENCE LISTING

<160> NUMBER OF SEQ ID NOS: 148

<210> SEQ ID NO 1
<211> LENGTH: 5
<212> TYPE: PRT
<213> ORGANISM: Homo sapiens

<400> SEQUENCE: 1

```
Asn Tyr Ala Ile Ser
 1               5
```

<210> SEQ ID NO 2
<211> LENGTH: 5
<212> TYPE: PRT
<213> ORGANISM: Homo sapiens

<400> SEQUENCE: 2

```
Ser Asn Tyr Ile Ser
 1               5
```

<210> SEQ ID NO 3
<211> LENGTH: 5
<212> TYPE: PRT
<213> ORGANISM: Homo sapiens

<400> SEQUENCE: 3

```
Asn Tyr Trp Ile Ser
 1               5
```

<210> SEQ ID NO 4
<211> LENGTH: 5
<212> TYPE: PRT
<213> ORGANISM: Homo sapiens

<400> SEQUENCE: 4

```
Ser Tyr Trp Ile Thr
 1               5
```

<210> SEQ ID NO 5
<211> LENGTH: 5
<212> TYPE: PRT
<213> ORGANISM: Homo sapiens

<400> SEQUENCE: 5

Asn Tyr Trp Ile Gly
1               5

<210> SEQ ID NO 6
<211> LENGTH: 5
<212> TYPE: PRT
<213> ORGANISM: Homo sapiens

<400> SEQUENCE: 6

Ser Phe Gly Met Ser
1               5

<210> SEQ ID NO 7
<211> LENGTH: 17
<212> TYPE: PRT
<213> ORGANISM: Homo sapiens

<400> SEQUENCE: 7

Gly Ile Ile Pro Met Phe Gly Tyr Ala Asn Tyr Ala Gln Lys Phe Gln
1               5                   10                  15

Gly

<210> SEQ ID NO 8
<211> LENGTH: 17
<212> TYPE: PRT
<213> ORGANISM: Homo sapiens

<400> SEQUENCE: 8

Gly Ile Ile Pro Val Phe Gly Phe Thr His Tyr Ala Gln Lys Phe Gln
1               5                   10                  15

Gly

<210> SEQ ID NO 9
<211> LENGTH: 17
<212> TYPE: PRT
<213> ORGANISM: Homo sapiens

<400> SEQUENCE: 9

Gly Ile Ile Pro Ile Phe Gly His Ala Asn Tyr Ala Gln Lys Phe Gln
1               5                   10                  15

Gly

<210> SEQ ID NO 10
<211> LENGTH: 17
<212> TYPE: PRT
<213> ORGANISM: Homo sapiens

<400> SEQUENCE: 10

Ile Ile Ile Pro Pro Ile Gly Asn Ala Trp Tyr Ala Gln Lys Phe Gln
1               5                   10                  15

Gly

<210> SEQ ID NO 11
<211> LENGTH: 17
<212> TYPE: PRT
<213> ORGANISM: Homo sapiens

<400> SEQUENCE: 11

Leu Ile Asp Pro Asn Phe Gly Gly Ala Tyr Tyr Ala Gln Lys Phe Gln
1               5                   10                  15

Gly

<210> SEQ ID NO 12
<211> LENGTH: 17
<212> TYPE: PRT
<213> ORGANISM: Homo sapiens

<400> SEQUENCE: 12

Leu Ile Asp Pro Val Phe Gly Gly Ala Tyr Tyr Ala Gln Lys Phe Gln
1               5                   10                  15

Gly

<210> SEQ ID NO 13
<211> LENGTH: 17
<212> TYPE: PRT
<213> ORGANISM: Homo sapiens

<400> SEQUENCE: 13

Leu Ile Asp Pro Met Phe Gly Gly Ala Tyr Tyr Ala Gln Lys Phe Gln
1               5                   10                  15

Gly

<210> SEQ ID NO 14
<211> LENGTH: 16
<212> TYPE: PRT
<213> ORGANISM: Homo sapiens

<400> SEQUENCE: 14

Ile Asn Ala His Leu Gly Gly Thr Trp Tyr Ala Gln Lys Phe Gln Gly
1               5                   10                  15

<210> SEQ ID NO 15
<211> LENGTH: 17
<212> TYPE: PRT
<213> ORGANISM: Homo sapiens

<400> SEQUENCE: 15

Ile Ser Pro Gly Thr Gly Ile Asn Ala Tyr Tyr Ala Gln Lys Phe Gln
1               5                   10                  15

Gly

<210> SEQ ID NO 16
<211> LENGTH: 17
<212> TYPE: PRT
<213> ORGANISM: Artificial Sequence
<220> FEATURE:
<223> OTHER INFORMATION: Synthesized human sequence
<220> FEATURE:
<221> NAME/KEY: unsure
<222> LOCATION: (1)
<223> OTHER INFORMATION: Where Xaa can be G, I, or L
<220> FEATURE:
<221> NAME/KEY: unsure
<222> LOCATION: (2)
<223> OTHER INFORMATION: Where Xaa can be I or S
<220> FEATURE:
<221> NAME/KEY: unsure
<222> LOCATION: (3)
<223> OTHER INFORMATION: Where Xaa can be I, P, N, or D
<220> FEATURE:
<221> NAME/KEY: unsure -continued

```
<222> LOCATION: (4)
<223> OTHER INFORMATION: Where Xaa can be P, G, or A
<220> FEATURE:
<221> NAME/KEY: unsure
<222> LOCATION: (5)
<223> OTHER INFORMATION: Where Xaa can be I, M, P,
<223> OTHER INFORMATION: T, H, N, or V
<220> FEATURE:
<221> NAME/KEY: unsure
<222> LOCATION: (6)
<223> OTHER INFORMATION: Where Xaa can be F, I, G, or L
<220> FEATURE:
<221> NAME/KEY: unsure
<222> LOCATION: (7)
<223> OTHER INFORMATION: Where Xaa can G or I
<220> FEATURE:
<221> NAME/KEY: unsure
<222> LOCATION: (8)
<223> OTHER INFORMATION: Where Xaa can be H, Y, N, or G
<220> FEATURE:
<221> NAME/KEY: unsure
<222> LOCATION: (9)
<223> OTHER INFORMATION: Where Xaa can be A or T
<220> FEATURE:
<221> NAME/KEY: unsure
<222> LOCATION: (10)
<223> OTHER INFORMATION: Where Xaa can be N, W, or Y

<400> SEQUENCE: 16

Xaa Xaa Xaa Xaa Xaa Xaa Xaa Xaa Xaa Xaa Tyr Ala Gln Lys Phe Gln
1               5                   10                  15

Gly

<210> SEQ ID NO 17
<211> LENGTH: 17
<212> TYPE: PRT
<213> ORGANISM: Homo sapiens

<400> SEQUENCE: 17

Trp Ile Arg Pro Gly Asp Ser Asp Thr Arg Tyr Ser Pro Ser Phe Glu
1               5                   10                  15

Gly

<210> SEQ ID NO 18
<211> LENGTH: 19
<212> TYPE: PRT
<213> ORGANISM: Homo sapiens

<400> SEQUENCE: 18

Val Ser Tyr Ile Ser Ser Ser Gly Ser Ser Thr Tyr Tyr Ala Asp Ser
1               5                   10                  15

Val Lys Gly

<210> SEQ ID NO 19
<211> LENGTH: 17
<212> TYPE: PRT
<213> ORGANISM: Homo sapiens

<400> SEQUENCE: 19

Ile Ile Asp Pro Ser Asn Ser Tyr Thr Asn Tyr Ser Pro Ser Phe Gln
1               5                   10                  15

Gly

<210> SEQ ID NO 20
<211> LENGTH: 17
<212> TYPE: PRT
<213> ORGANISM: Homo sapiens
```

```
<400> SEQUENCE: 20

Ile Ile Asp Pro Ser Asn Ser Tyr Thr Arg Tyr Ser Pro Ser Phe Gln
1               5                   10                  15

Gly

<210> SEQ ID NO 21
<211> LENGTH: 17
<212> TYPE: PRT
<213> ORGANISM: Homo sapiens

<400> SEQUENCE: 21

Ile Ile Asp Pro Ser Asn Ser Tyr Thr Asp Tyr Ser Pro Ser Phe Gln
1               5                   10                  15

Gly

<210> SEQ ID NO 22
<211> LENGTH: 17
<212> TYPE: PRT
<213> ORGANISM: Homo sapiens

<400> SEQUENCE: 22

Ile Ile Ser Pro Thr Gly Ser Val Thr Trp Tyr Ser Pro Ser Phe Gln
1               5                   10                  15

Gly

<210> SEQ ID NO 23
<211> LENGTH: 17
<212> TYPE: PRT
<213> ORGANISM: Homo sapiens

<400> SEQUENCE: 23

Ile Ile Ser Pro Thr Gly Ser Ser Thr Trp Tyr Ser Pro Ser Phe Gln
1               5                   10                  15

Gly

<210> SEQ ID NO 24
<211> LENGTH: 17
<212> TYPE: PRT
<213> ORGANISM: Homo sapiens

<400> SEQUENCE: 24

Phe Ile Ser Pro Asp Gly Ser His Thr Trp Tyr Ser Pro Ser Phe Gln
1               5                   10                  15

Gly

<210> SEQ ID NO 25
<211> LENGTH: 17
<212> TYPE: PRT
<213> ORGANISM: Homo sapiens

<400> SEQUENCE: 25

Ile Ile Ser Pro Ser Gly Ser Thr Thr Trp Tyr Ser Pro Ser Phe Gln
1               5                   10                  15

Gly

<210> SEQ ID NO 26
<211> LENGTH: 17
<212> TYPE: PRT
<213> ORGANISM: Homo sapiens
```

```
<400> SEQUENCE: 26

Ile Ile Ser Pro Thr Gly Ser Ala Thr Trp Tyr Ser Pro Ser Phe Gln
1               5                   10                  15
Gly

<210> SEQ ID NO 27
<211> LENGTH: 17
<212> TYPE: PRT
<213> ORGANISM: Homo sapiens

<400> SEQUENCE: 27

Ile Ile Asp Pro Val Ser Ser Trp Thr Lys Tyr Ser Pro Ser Phe Gln
1               5                   10                  15
Gly

<210> SEQ ID NO 28
<211> LENGTH: 17
<212> TYPE: PRT
<213> ORGANISM: Artificial Sequence
<220> FEATURE:
<223> OTHER INFORMATION: Synthesized human sequence
<220> FEATURE:
<221> NAME/KEY: unsure
<222> LOCATION: (3)
<223> OTHER INFORMATION: Where Xaa can be D or S
<220> FEATURE:
<221> NAME/KEY: unsure
<222> LOCATION: (5)
<223> OTHER INFORMATION: Where Xaa can be S, V, D, or T
<220> FEATURE:
<221> NAME/KEY: unsure
<222> LOCATION: (6)
<223> OTHER INFORMATION: Where Xaa can be N, S, or G
<220> FEATURE:
<221> NAME/KEY: unsure
<222> LOCATION: (8)
<223> OTHER INFORMATION: Where Xaa can be Y, W, T, H, V, S, or A
<220> FEATURE:
<221> NAME/KEY: unsure
<222> LOCATION: (10)
<223> OTHER INFORMATION: Where Xaa can be N, D, R, K, or W

<400> SEQUENCE: 28

Ile Ile Xaa Pro Xaa Xaa Ser Xaa Thr Xaa Tyr Ser Pro Ser Phe Gln
1               5                   10                  15
Gly

<210> SEQ ID NO 29
<211> LENGTH: 17
<212> TYPE: PRT
<213> ORGANISM: Homo sapiens

<400> SEQUENCE: 29

Asn Ile Ser Ser Ser Gly Ser Ser Thr Tyr Tyr Ala Asp Ser Val Lys
1               5                   10                  15
Gly

<210> SEQ ID NO 30
<211> LENGTH: 19
<212> TYPE: PRT
<213> ORGANISM: Homo sapiens
```

<400> SEQUENCE: 30

Asn Ile Glu His Lys Tyr Leu Asn Tyr Ala Thr Tyr Tyr Ala Ala Ser
1               5                   10                  15

Val Lys Gly

<210> SEQ ID NO 31
<211> LENGTH: 19
<212> TYPE: PRT
<213> ORGANISM: Homo sapiens

<400> SEQUENCE: 31

Asn Ile Glu His Lys Phe Met Gly Tyr Thr Thr Tyr Tyr Ala Ala Gly
1               5                   10                  15

Val Lys Gly

<210> SEQ ID NO 32
<211> LENGTH: 19
<212> TYPE: PRT
<213> ORGANISM: Homo sapiens

<400> SEQUENCE: 32

Gly Ile Glu His Lys Tyr Leu Ser Tyr Thr Thr His Tyr Ala Ala Ser
1               5                   10                  15

Val Lys Gly

<210> SEQ ID NO 33
<211> LENGTH: 19
<212> TYPE: PRT
<213> ORGANISM: Homo sapiens

<400> SEQUENCE: 33

Ser Ile Glu His Lys Tyr Thr Gly Tyr Thr Thr Tyr Tyr Ala Ala Pro
1               5                   10                  15

Val Lys Gly

<210> SEQ ID NO 34
<211> LENGTH: 19
<212> TYPE: PRT
<213> ORGANISM: Homo sapiens

<400> SEQUENCE: 34

Gln Ile Glu His Lys Tyr Leu Ser Tyr Thr Thr Leu Tyr Ala Ala Ser
1               5                   10                  15

Val Lys Gly

<210> SEQ ID NO 35
<211> LENGTH: 19
<212> TYPE: PRT
<213> ORGANISM: Homo sapiens

<400> SEQUENCE: 35

Ser Ile Glu His Lys Tyr Leu Ser Tyr Thr Thr Phe Tyr Ala Ala Ser
1               5                   10                  15

Val Lys Gly

<210> SEQ ID NO 36
<211> LENGTH: 19
<212> TYPE: PRT
<213> ORGANISM: Homo sapiens

<400> SEQUENCE: 36

Asn Ile Glu Gly Lys Tyr Thr Ser Tyr Thr Tyr Tyr Ala Ala Ser
1               5                   10                  15

Val Lys Gly

<210> SEQ ID NO 37
<211> LENGTH: 19
<212> TYPE: PRT
<213> ORGANISM: Homo sapiens

<400> SEQUENCE: 37

Gly Ile Glu His Lys Tyr Leu Ser Tyr Ala Thr Leu Tyr Ala Ala Ser
1               5                   10                  15

Val Lys Gly

<210> SEQ ID NO 38
<211> LENGTH: 19
<212> TYPE: PRT
<213> ORGANISM: Homo sapiens

<400> SEQUENCE: 38

Asn Ile Glu His Lys Tyr Leu Gly Tyr Ala Thr Val Tyr Ala Ala Ser
1               5                   10                  15

Val Lys Gly

<210> SEQ ID NO 39
<211> LENGTH: 19
<212> TYPE: PRT
<213> ORGANISM: Homo sapiens

<400> SEQUENCE: 39

Ser Ile Glu His Lys Tyr Leu Ser Tyr Ala Thr Tyr Tyr Ala Ala Gly
1               5                   10                  15

Val Lys Gly

<210> SEQ ID NO 40
<211> LENGTH: 8
<212> TYPE: PRT
<213> ORGANISM: Homo sapiens

<400> SEQUENCE: 40

Asp Ile Tyr Ala Gly Met Asp Val
1               5

<210> SEQ ID NO 41
<211> LENGTH: 18
<212> TYPE: PRT
<213> ORGANISM: Homo sapiens

<400> SEQUENCE: 41

Ser Lys Lys Gly Met Tyr Gly Gly Trp Thr Tyr Pro Leu Met Met Phe
1               5                   10                  15

Asp Leu

<210> SEQ ID NO 42
<211> LENGTH: 7
<212> TYPE: PRT
<213> ORGANISM: Homo sapiens

<400> SEQUENCE: 42

His Tyr Tyr Gly Met Asp Tyr
1               5

<210> SEQ ID NO 43
<211> LENGTH: 12
<212> TYPE: PRT
<213> ORGANISM: Homo sapiens

<400> SEQUENCE: 43

Gly Thr Phe Trp Ser Phe Gly Asn Tyr Phe Ala Asn
1               5                   10

<210> SEQ ID NO 44
<211> LENGTH: 8
<212> TYPE: PRT
<213> ORGANISM: Homo sapiens

<400> SEQUENCE: 44

Trp Tyr Tyr Lys Pro Phe Asp Val
1               5

<210> SEQ ID NO 45
<211> LENGTH: 12
<212> TYPE: PRT
<213> ORGANISM: Homo sapiens

<400> SEQUENCE: 45

Tyr Trp Gly Thr Pro Tyr Leu Met Gln Phe Asp Asn
1               5                   10

<210> SEQ ID NO 46
<211> LENGTH: 12
<212> TYPE: PRT
<213> ORGANISM: Homo sapiens

<400> SEQUENCE: 46

Arg Ala Ser Gln Ser Val Leu Gly Asn Tyr Leu Ala
1               5                   10

<210> SEQ ID NO 47
<211> LENGTH: 12
<212> TYPE: PRT
<213> ORGANISM: Homo sapiens

<400> SEQUENCE: 47

Arg Ala Ser Gln Ser Val Ser Ser Asn Tyr Leu Ala
1               5                   10

<210> SEQ ID NO 48
<211> LENGTH: 13
<212> TYPE: PRT
<213> ORGANISM: Homo sapiens

<400> SEQUENCE: 48

Ser Gly Ser Ser Ser Asn Ile Gly Ser Tyr Tyr Val Asn
1               5                   10

<210> SEQ ID NO 49
<211> LENGTH: 11
<212> TYPE: PRT
<213> ORGANISM: Homo sapiens

<400> SEQUENCE: 49

Arg Ala Ser Gln Ser Ile Phe Tyr Asn Leu Ala
1               5                   10

<210> SEQ ID NO 50
<211> LENGTH: 14
<212> TYPE: PRT
<213> ORGANISM: Homo sapiens

<400> SEQUENCE: 50

Thr Gly Ser Ser Ser Asn Ile Gly Ser Gly Tyr Asp Val His
1               5                   10

<210> SEQ ID NO 51
<211> LENGTH: 14
<212> TYPE: PRT
<213> ORGANISM: Homo sapiens

<400> SEQUENCE: 51

Thr Gly Thr Ser Ser Asp Val Gly Gly Tyr Asn Ser Val Ser
1               5                   10

<210> SEQ ID NO 52
<211> LENGTH: 7
<212> TYPE: PRT
<213> ORGANISM: Homo sapiens

<400> SEQUENCE: 52

Gly Ala Ser Ser Arg Ala Thr
1               5

<210> SEQ ID NO 53
<211> LENGTH: 7
<212> TYPE: PRT
<213> ORGANISM: Homo sapiens

<400> SEQUENCE: 53

Tyr Ala Ser Arg Arg Ala Thr
1               5

<210> SEQ ID NO 54
<211> LENGTH: 7
<212> TYPE: PRT
<213> ORGANISM: Homo sapiens

<400> SEQUENCE: 54

Gly Asn Thr His Arg Pro Ser
1               5

<210> SEQ ID NO 55
<211> LENGTH: 7
<212> TYPE: PRT
<213> ORGANISM: Homo sapiens

<400> SEQUENCE: 55

Gly Ala Ser Asn Arg Ala Thr
1               5

<210> SEQ ID NO 56
<211> LENGTH: 7
<212> TYPE: PRT
<213> ORGANISM: Homo sapiens

<400> SEQUENCE: 56

Gly Asn Ser Lys Arg Pro Ser
1               5

<210> SEQ ID NO 57
<211> LENGTH: 7
<212> TYPE: PRT
<213> ORGANISM: Homo sapiens

<400> SEQUENCE: 57

Ser Val Ser Ser Arg Pro Ser
1               5

<210> SEQ ID NO 58
<211> LENGTH: 9
<212> TYPE: PRT
<213> ORGANISM: Homo sapiens

<400> SEQUENCE: 58

His Gln Tyr Gly Ser Ile Ser Thr Thr
1               5

<210> SEQ ID NO 59
<211> LENGTH: 9
<212> TYPE: PRT
<213> ORGANISM: Homo sapiens

<400> SEQUENCE: 59

Gln Gln Tyr Ser His Leu Leu Ile Thr
1               5

<210> SEQ ID NO 60
<211> LENGTH: 9
<212> TYPE: PRT
<213> ORGANISM: Homo sapiens

<400> SEQUENCE: 60

Gln Gln Tyr Ser His Ile Ser Leu Thr
1               5

<210> SEQ ID NO 61
<211> LENGTH: 9
<212> TYPE: PRT
<213> ORGANISM: Homo sapiens

<400> SEQUENCE: 61

Gln Gln Phe Ala His Ile Leu Leu Thr
1               5

<210> SEQ ID NO 62
<211> LENGTH: 9
<212> TYPE: PRT
<213> ORGANISM: Homo sapiens

<400> SEQUENCE: 62

Gln Gln Thr Ser Asn Thr Pro Phe Thr
1               5

<210> SEQ ID NO 63
<211> LENGTH: 9
<212> TYPE: PRT
<213> ORGANISM: Homo sapiens

```
<400> SEQUENCE: 63

Gln Gln Phe Ile Thr Tyr Leu Pro Thr
1               5

<210> SEQ ID NO 64
<211> LENGTH: 9
<212> TYPE: PRT
<213> ORGANISM: Homo sapiens

<400> SEQUENCE: 64

Gln Gln Asp Ala Leu Ser Pro Phe Thr
1               5

<210> SEQ ID NO 65
<211> LENGTH: 9
<212> TYPE: PRT
<213> ORGANISM: Homo sapiens

<400> SEQUENCE: 65

Gln Gln Asp Arg Gly Thr Pro Phe Thr
1               5

<210> SEQ ID NO 66
<211> LENGTH: 9
<212> TYPE: PRT
<213> ORGANISM: Homo sapiens

<400> SEQUENCE: 66

Gln Gln Ser Leu Asn Ile Pro Phe Thr
1               5

<210> SEQ ID NO 67
<211> LENGTH: 9
<212> TYPE: PRT
<213> ORGANISM: Homo sapiens

<400> SEQUENCE: 67

Gln Gln Asp Thr Ser Ser Pro Phe Thr
1               5

<210> SEQ ID NO 68
<211> LENGTH: 10
<212> TYPE: PRT
<213> ORGANISM: Artificial Sequence
<220> FEATURE:
<223> OTHER INFORMATION: Synthesized human sequence
<220> FEATURE:
<221> NAME/KEY: unsure
<222> LOCATION: (3)
<223> OTHER INFORMATION: Where Xaa can be T, F, D, or S
<220> FEATURE:
<221> NAME/KEY: unsure
<222> LOCATION: (4)
<223> OTHER INFORMATION: Where Xaa can be S, I, A, T, R, or L
<220> FEATURE:
<221> NAME/KEY: unsure
<222> LOCATION: (5)
<223> OTHER INFORMATION: Where Xaa can be N, T, L, S, or G
<220> FEATURE:
<221> NAME/KEY: unsure
<222> LOCATION: (6)
<223> OTHER INFORMATION: Where Xaa can be T, Y, S, or I
<220> FEATURE:
<221> NAME/KEY: unsure
<222> LOCATION: (7)
<223> OTHER INFORMATION: Where Xaa can be P or L
<220> FEATURE:
<221> NAME/KEY: unsure
```

<222> LOCATION: (8)
<223> OTHER INFORMATION: Where Xaa can be F or P

<400> SEQUENCE: 68

Gln Gln Xaa Xaa Xaa Xaa Xaa Xaa Phe Thr
1               5                   10

<210> SEQ ID NO 69
<211> LENGTH: 11
<212> TYPE: PRT
<213> ORGANISM: Homo sapiens

<400> SEQUENCE: 69

Gln Thr Tyr Ala Ser Leu Gly Pro Gly Glu Val
1               5                   10

<210> SEQ ID NO 70
<211> LENGTH: 9
<212> TYPE: PRT
<213> ORGANISM: Homo sapiens

<400> SEQUENCE: 70

Gln Gln Tyr Ser Ser Glu Pro Val Thr
1               5

<210> SEQ ID NO 71
<211> LENGTH: 9
<212> TYPE: PRT
<213> ORGANISM: Homo sapiens

<400> SEQUENCE: 71

Ser Ser Trp Thr Pro Ser Ser Val Val
1               5

<210> SEQ ID NO 72
<211> LENGTH: 11
<212> TYPE: PRT
<213> ORGANISM: Homo sapiens

<400> SEQUENCE: 72

Ser Ser Trp Thr Asp Thr Pro Asn Met Ile Val
1               5                   10

<210> SEQ ID NO 73
<211> LENGTH: 11
<212> TYPE: PRT
<213> ORGANISM: Homo sapiens

<400> SEQUENCE: 73

Ala Ser Trp Thr Asp Gly Leu Ser Leu Val Val
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Synthesized human sequence
<220> FEATURE:
<221> NAME/KEY: unsure
<222> LOCATION: (1)
<223> OTHER INFORMATION: Where Xaa can be S or A
<220> FEATURE:
<221> NAME/KEY: unsure
<222> LOCATION: (6)
<223> OTHER INFORMATION: Where Xaa can be T or G
<220> FEATURE:

```
<221> NAME/KEY: unsure
<222> LOCATION: (7)
<223> OTHER INFORMATION: Where Xaa can be P or L
<220> FEATURE:
<221> NAME/KEY: unsure
<222> LOCATION: (8)
<223> OTHER INFORMATION: Where Xaa can be S or N
<220> FEATURE:
<221> NAME/KEY: unsure
<222> LOCATION: (9)
<223> OTHER INFORMATION: Where Xaa can be S, M, or L
<220> FEATURE:
<221> NAME/KEY: unsure
<222> LOCATION: (10)
<223> OTHER INFORMATION: Where Xaa can be I or V

<400> SEQUENCE: 74

Xaa Ser Trp Thr Asp Xaa Xaa Xaa Xaa Xaa Val
1               5                   10

<210> SEQ ID NO 75
<211> LENGTH: 11
<212> TYPE: PRT
<213> ORGANISM: Homo sapiens

<400> SEQUENCE: 75

Ser Ser Tyr Asp Thr Asn Lys Pro Leu Val Val
1               5                   10

<210> SEQ ID NO 76
<211> LENGTH: 11
<212> TYPE: PRT
<213> ORGANISM: Homo sapiens

<400> SEQUENCE: 76

Gly Ser Tyr Asp Val Tyr Gly Arg Phe Tyr Val
1               5                   10

<210> SEQ ID NO 77
<211> LENGTH: 11
<212> TYPE: PRT
<213> ORGANISM: Homo sapiens

<400> SEQUENCE: 77

Ser Ser Tyr Tyr Phe Tyr Leu Gln Arg Ile Val
1               5                   10

<210> SEQ ID NO 78
<211> LENGTH: 11
<212> TYPE: PRT
<213> ORGANISM: Homo sapiens

<400> SEQUENCE: 78

Gln Thr Tyr Tyr Phe Ser Tyr Ser Gly Pro Val
1               5                   10

<210> SEQ ID NO 79
<211> LENGTH: 11
<212> TYPE: PRT
<213> ORGANISM: Homo sapiens

<400> SEQUENCE: 79

Gly Ser Trp Asp Pro Ile Phe Ser Tyr Glu Val
1               5                   10

<210> SEQ ID NO 80
<211> LENGTH: 117
```

```
<212> TYPE: PRT
<213> ORGANISM: Homo sapiens

<400> SEQUENCE: 80

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Met Phe Gly Tyr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ile Tyr Ala Gly Met Asp Val Trp Gly Gln Gly Thr Leu
            100                 105                 110

Val Thr Val Ser Ser
            115

<210> SEQ ID NO 81
<211> LENGTH: 117
<212> TYPE: PRT
<213> ORGANISM: Homo sapiens

<400> SEQUENCE: 81

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Val Phe Gly Phe Thr His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ile Tyr Ala Gly Met Asp Val Trp Gly Gln Gly Thr Leu
            100                 105                 110

Val Thr Val Ser Ser
            115

<210> SEQ ID NO 82
<211> LENGTH: 108
<212> TYPE: PRT
<213> ORGANISM: Homo sapiens

<400> SEQUENCE: 82

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Leu Gly Asn
            20                  25                  30

Tyr Leu Ala Trp Tyr Gln Gln Lys Pro Gly Gln Ala Pro Arg Leu Leu
        35                  40                  45
```

-continued

Ile Tyr Gly Ala Ser Ser Arg Ala Thr Gly Val Pro Ala Arg Phe Ser
            50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys His Gln Tyr Gly Ser Ile Ser
                85                  90                  95

Thr Thr Phe Gly Gln Gly Thr Lys Val Glu Ile Lys
            100                 105

<210> SEQ ID NO 83
<211> LENGTH: 108
<212> TYPE: PRT
<213> ORGANISM: Homo sapiens

<400> SEQUENCE: 83

Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Leu Gly Asn
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Val Pro Ala Arg Phe Ser
        50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln Tyr Ser His Ile Ser
                85                  90                  95

Leu Thr Phe Gly Gln Gly Thr Lys Val Glu Ile Lys
            100                 105

<210> SEQ ID NO 84
<211> LENGTH: 108
<212> TYPE: PRT
<213> ORGANISM: Homo sapiens

<400> SEQUENCE: 84

Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Leu Gly Asn
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Val Pro Ala Arg Phe Ser
        50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln Tyr Ser His Leu Ile
                85                  90                  95

Ile Thr Phe Gly Gln Gly Thr Lys Val Glu Ile Lys
            100                 105

<210> SEQ ID NO 85
<211> LENGTH: 108
<212> TYPE: PRT
<213> ORGANISM: Homo sapiens

<400> SEQUENCE: 85

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Leu Gly Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Phe Ala His Ile Leu
                85                  90                  95

Leu Thr Phe Gly Gln Gly Thr Lys Val Glu Ile Lys
            100                 105

<210> SEQ ID NO 86
<211> LENGTH: 127
<212> TYPE: PRT
<213> ORGANISM: Homo sapiens

<400> SEQUENCE: 86

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Tyr Ile Ser Trp Val Arg Gln Ala Pro Gly Gln Gly Leu Glu Trp Met
        35                  40                  45

Gly Gly Ile Ile Pro Ile Phe Gly His Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Lys Gly Met Tyr Gly Gly Trp Thr Tyr Pro Leu Met
            100                 105                 110

Met Phe Asp Leu Trp Gly Gln Gly Thr Leu Val Thr Val Ser Ser
        115                 120                 125

<210> SEQ ID NO 87
<211> LENGTH: 127
<212> TYPE: PRT
<213> ORGANISM: Homo sapiens

<400> SEQUENCE: 87

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Tyr Ile Ser Trp Val Arg Gln Ala Pro Gly Gln Gly Leu Glu Trp Met
        35                  40                  45

Gly Ile Ile Ile Pro Pro Ile Gly Asn Ala Trp Tyr Ala Gln Lys Phe
50                  55                  60

Gln Gly Arg Val Thr Ile Thr Ala Asp Glu Ser Thr Ser Thr Ala Tyr
65                  70                  75                  80

-continued

```
Met Glu Leu Ser Ser Leu Arg Ser Glu Asp Thr Ala Val Tyr Tyr Cys
            85                  90                  95

Ala Arg Ser Lys Lys Gly Met Tyr Gly Gly Trp Thr Tyr Pro Leu Met
            100                 105                 110

Met Phe Asp Leu Trp Gly Gln Gly Thr Leu Val Thr Val Ser Ser
            115                 120                 125

<210> SEQ ID NO 88
<211> LENGTH: 127
<212> TYPE: PRT
<213> ORGANISM: Homo sapiens

<400> SEQUENCE: 88

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Tyr Ile Ser Trp Val Arg Gln Ala Pro Gly Gln Gly Leu Glu Trp Met
            35                  40                  45

Gly Ile Ser Pro Gly Thr Gly Ile Asn Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Ser Lys Lys Gly Met Tyr Gly Gly Trp Thr Tyr Pro Leu Met
            100                 105                 110

Met Phe Asp Leu Trp Gly Gln Gly Thr Leu Val Thr Val Ser Ser
            115                 120                 125

<210> SEQ ID NO 89
<211> LENGTH: 126
<212> TYPE: PRT
<213> ORGANISM: Homo sapiens

<400> SEQUENCE: 89

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Tyr Ile Ser Trp Val Arg Gln Ala Pro Gly Gln Gly Leu Glu Trp Met
            35                  40                  45

Gly Ile Asn Ala His Leu Gly Gly Thr Trp Tyr Ala Gln Lys Phe Gln
    50                  55                  60

Gly Arg Val Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
            85                  90                  95

Arg Ser Lys Lys Gly Met Tyr Gly Gly Trp Thr Tyr Pro Leu Met Met
            100                 105                 110

Phe Asp Leu Trp Gly Gln Gly Thr Leu Val Thr Val Ser Ser
            115                 120                 125

<210> SEQ ID NO 90
<211> LENGTH: 127
<212> TYPE: PRT
<213> ORGANISM: Homo sapiens
```

<400> SEQUENCE: 90

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Tyr Ile Ser Trp Val Arg Gln Ala Pro Gly Gln Gly Leu Glu Trp Met
        35                  40                  45

Gly Leu Ile Asp Pro Asn Phe Gly Gly Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Lys Gly Met Tyr Gly Gly Trp Thr Tyr Pro Leu Met
            100                 105                 110

Met Phe Asp Leu Trp Gly Gln Gly Thr Leu Val Thr Val Ser Ser
        115                 120                 125

<210> SEQ ID NO 91
<211> LENGTH: 127
<212> TYPE: PRT
<213> ORGANISM: Homo sapiens

<400> SEQUENCE: 91

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Tyr Ile Ser Trp Val Arg Gln Ala Pro Gly Gln Gly Leu Glu Trp Met
        35                  40                  45

Gly Leu Ile Asp Pro Val Phe Gly Gly Ala Tyr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Lys Gly Met Tyr Gly Gly Trp Thr Tyr Pro Leu Met
            100                 105                 110

Met Phe Asp Leu Trp Gly Gln Gly Thr Leu Val Thr Val Ser Ser
        115                 120                 125

<210> SEQ ID NO 92
<211> LENGTH: 127
<212> TYPE: PRT
<213> ORGANISM: Homo sapiens

<400> SEQUENCE: 92

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Tyr Ile Ser Trp Val Arg Gln Ala Pro Gly Gln Gly Leu Glu Trp Met
        35                  40                  45

Gly Leu Ile Asp Pro Met Phe Gly Gly Ala Tyr Tyr Ala Gln Lys Phe
    50                  55                  60

```
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Lys Lys Gly Met Tyr Gly Gly Trp Thr Tyr Pro Leu Met
            100                 105                 110

Met Phe Asp Leu Trp Gly Gln Gly Thr Leu Val Thr Val Ser Ser
        115                 120                 125
```

<210> SEQ ID NO 93
<211> LENGTH: 108
<212> TYPE: PRT
<213> ORGANISM: Homo sapiens

<400> SEQUENCE: 93

```
Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Asn
                20                  25                  30

Tyr Leu Ala Trp Tyr Gln Gln Lys Pro Gly Gln Ala Pro Arg Leu Leu
            35                  40                  45

Ile Tyr Tyr Ala Ser Arg Arg Ala Thr Gly Val Pro Ala Arg Phe Ser
 50                  55                  60

Gly Ser Gly Ser Gly Thr Asp Phe Thr Leu Thr Ile Ser Ser Leu Glu
 65                  70                  75                  80

Pro Glu Asp Phe Ala Thr Tyr Tyr Cys Gln Gln Thr Ser Asn Thr Pro
                 85                  90                  95

Phe Thr Phe Gly Gln Gly Thr Lys Val Glu Ile Lys
            100                 105
```

<210> SEQ ID NO 94
<211> LENGTH: 108
<212> TYPE: PRT
<213> ORGANISM: Homo sapiens

<400> SEQUENCE: 94

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Asn
                20                  25                  30

Tyr Leu Ala Trp Tyr Gln Gln Lys Pro Gly Gln Ala Pro Arg Leu Leu
            35                  40                  45

Ile Tyr Tyr Ala Ser Arg Arg Ala Thr Gly Val Pro Ala Arg Phe Ser
 50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln Thr Ser Asn Thr Pro
                 85                  90                  95

Phe Thr Phe Gly Gln Gly Thr Lys Val Glu Ile Lys
            100                 105
```

<210> SEQ ID NO 95
<211> LENGTH: 108
<212> TYPE: PRT
<213> ORGANISM: Homo sapiens

```
<400> SEQUENCE: 95

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Tyr Ala Ser Arg Arg Ala Thr Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Phe Ile Thr Tyr Leu
                85                  90                  95

Pro Thr Phe Gly Gln Gly Thr Lys Val Glu Ile Lys
                100                 105

<210> SEQ ID NO 96
<211> LENGTH: 108
<212> TYPE: PRT
<213> ORGANISM: Homo sapiens

<400> SEQUENCE: 96

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Tyr Ala Ser Arg Arg Ala Thr Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Asp Ala Leu Ser Pro
                85                  90                  95

Phe Thr Phe Gly Gln Gly Thr Lys Val Glu Ile Lys
                100                 105

<210> SEQ ID NO 97
<211> LENGTH: 108
<212> TYPE: PRT
<213> ORGANISM: Homo sapiens

<400> SEQUENCE: 97

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Tyr Ala Ser Arg Arg Ala Thr Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Asp Arg Gly Thr Pro
                85                  90                  95
```

```
Phe Thr Phe Gly Gln Gly Thr Lys Val Glu Ile Lys
            100                 105
```

<210> SEQ ID NO 98
<211> LENGTH: 108
<212> TYPE: PRT
<213> ORGANISM: Homo sapiens

<400> SEQUENCE: 98

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Tyr Ala Ser Arg Arg Ala Thr Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Ser Leu Asn Ile Pro
                85                  90                  95

Phe Thr Phe Gly Gln Gly Thr Lys Val Glu Ile Lys
            100                 105
```

<210> SEQ ID NO 99
<211> LENGTH: 116
<212> TYPE: PRT
<213> ORGANISM: Homo sapiens

<400> SEQUENCE: 99

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Ser Trp Val Arg Gln Ala Pro Gly Lys Gly Leu Glu Trp Met
        35                  40                  45

Gly Trp Ile Arg Pro Gly Asp Ser Asp Thr Arg Tyr Ser Pro Ser Phe
50                  55                  60

Glu Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Tyr Tyr Gly Met Asp Tyr Trp Gly Gln Gly Thr Leu Val
            100                 105                 110

Thr Val Ser Ser
        115
```

<210> SEQ ID NO 100
<211> LENGTH: 110
<212> TYPE: PRT
<213> ORGANISM: Homo sapiens

<400> SEQUENCE: 100

```
Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Tyr
            20                  25                  30
```

```
Tyr Val Asn Trp Tyr Gln Gln Leu Pro Gly Thr Ala Pro Lys Leu Leu
            35                  40                  45

Ile Tyr Gly Asn Thr His Arg Pro Ser Gly Val Pro Asp Arg Phe Ser
        50                  55                  60

Gly Ser Lys Ser Gly Thr Ser Ala Ser Leu Ala Ile Thr Gly Leu Gln
 65                  70                  75                  80

Ser Glu Asp Glu Ala Asp Tyr Tyr Cys Gln Thr Tyr Ala Ser Leu Gly
                 85                  90                  95

Pro Gly Glu Val Phe Gly Gly Gly Thr Lys Leu Thr Val Leu
                100                 105                 110
```

<210> SEQ ID NO 101
<211> LENGTH: 121
<212> TYPE: PRT
<213> ORGANISM: Homo sapiens

<400> SEQUENCE: 101

```
Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Trp Ile Thr Trp Val Arg Gln Ala Pro Gly Lys Gly Leu Glu Trp Val
            35                  40                  45

Ser Tyr Ile Ser Ser Ser Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Thr Phe Trp Ser Phe Gly Asn Tyr Phe Ala Asn Trp Gly
                100                 105                 110

Gln Gly Thr Leu Val Thr Val Ser Ser
            115                 120
```

<210> SEQ ID NO 102
<211> LENGTH: 107
<212> TYPE: PRT
<213> ORGANISM: Homo sapiens

<400> SEQUENCE: 102

```
Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Ile Phe Tyr Asn
             20                  25                  30

Leu Ala Trp Tyr Gln Gln Lys Pro Gly Gln Ala Pro Arg Leu Leu Ile
            35                  40                  45

Tyr Gly Ala Ser Asn Arg Ala Thr Gly Val Pro Ala Arg Phe Ser Gly
        50                  55                  60

Ser Gly Ser Gly Thr Asp Phe Thr Leu Thr Ile Ser Ser Leu Glu Pro
 65                  70                  75                  80

Glu Asp Phe Ala Thr Tyr Tyr Cys Gln Gln Tyr Ser Ser Glu Pro Val
                 85                  90                  95

Thr Phe Gly Gln Gly Thr Lys Val Glu Ile Lys
                100                 105
```

<210> SEQ ID NO 103

```
<211> LENGTH: 117
<212> TYPE: PRT
<213> ORGANISM: Homo sapiens

<400> SEQUENCE: 103

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
                20                  25                  30

Trp Ile Gly Trp Val Arg Gln Met Pro Gly Lys Gly Leu Glu Trp Met
            35                  40                  45

Gly Ile Ile Asp Pro Ser Asn Ser Tyr Thr Asn Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
                100                 105                 110

Val Thr Val Ser Ser
            115

<210> SEQ ID NO 104
<211> LENGTH: 117
<212> TYPE: PRT
<213> ORGANISM: Homo sapiens

<400> SEQUENCE: 104

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
                20                  25                  30

Trp Ile Gly Trp Val Arg Gln Met Pro Gly Lys Gly Leu Glu Trp Met
            35                  40                  45

Gly Ile Ile Asp Pro Ser Asn Ser Tyr Thr Asp Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
                100                 105                 110

Val Thr Val Ser Ser
            115

<210> SEQ ID NO 105
<211> LENGTH: 117
<212> TYPE: PRT
<213> ORGANISM: Homo sapiens

<400> SEQUENCE: 105

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
                20                  25                  30

Trp Ile Gly Trp Val Arg Gln Met Pro Gly Lys Gly Leu Glu Trp Met
            35                  40                  45
```

```
Gly Ile Ile Asp Pro Ser Asn Ser Tyr Thr Arg Tyr Ser Pro Ser Phe
        50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Trp Tyr Tyr Lys Pro Phe Asp Val Trp Gly Gln Gly Thr Leu
                100                 105                 110

Val Thr Val Ser Ser
            115

<210> SEQ ID NO 106
<211> LENGTH: 117
<212> TYPE: PRT
<213> ORGANISM: Homo sapiens

<400> SEQUENCE: 106

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Ser Asn Tyr
                 20                  25                  30

Trp Ile Gly Trp Val Arg Gln Met Pro Gly Lys Gly Leu Glu Trp Met
             35                  40                  45

Gly Ile Ile Asp Pro Ser Asn Ser Tyr Thr Arg Tyr Ser Pro Ser Phe
        50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Trp Tyr Tyr Lys Pro Phe Asp Val Trp Gly Gln Gly Thr Leu
                100                 105                 110

Val Thr Val Ser Ser
            115

<210> SEQ ID NO 107
<211> LENGTH: 117
<212> TYPE: PRT
<213> ORGANISM: Homo sapiens

<400> SEQUENCE: 107

Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Ser Asn Tyr
                 20                  25                  30

Trp Ile Gly Trp Val Arg Gln Met Pro Gly Lys Gly Leu Glu Trp Met
             35                  40                  45

Gly Ile Ile Asp Pro Val Ser Ser Trp Thr Lys Tyr Ser Pro Ser Phe
        50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Trp Tyr Tyr Lys Pro Phe Asp Val Trp Gly Gln Gly Thr Leu
                100                 105                 110

Val Thr Val Ser Ser
            115
```

<210> SEQ ID NO 108
<211> LENGTH: 117
<212> TYPE: PRT
<213> ORGANISM: Homo sapiens

<400> SEQUENCE: 108

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Ser Pro Ser Gly Ser Thr Thr Trp Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
            100                 105                 110

Val Thr Val Ser Ser
            115

<210> SEQ ID NO 109
<211> LENGTH: 117
<212> TYPE: PRT
<213> ORGANISM: Homo sapiens

<400> SEQUENCE: 109

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Phe Ile Ser Pro Asp Gly Ser His Thr Trp Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
            100                 105                 110

Val Thr Val Ser Ser
            115

<210> SEQ ID NO 110
<211> LENGTH: 117
<212> TYPE: PRT
<213> ORGANISM: Homo sapiens

<400> SEQUENCE: 110

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
            35                  40                  45

Gly Ile Ile Ser Pro Thr Gly Ser Val Thr Trp Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
                100                 105                 110

Val Thr Val Ser Ser
        115

<210> SEQ ID NO 111
<211> LENGTH: 117
<212> TYPE: PRT
<213> ORGANISM: Homo sapiens

<400> SEQUENCE: 111

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
                20                  25                  30

Trp Ile Gly Trp Val Arg Gln Met Pro Gly Lys Gly Leu Glu Trp Met
            35                  40                  45

Gly Ile Ile Ser Pro Thr Gly Ser Ser Thr Trp Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
                100                 105                 110

Val Thr Val Ser Ser
        115

<210> SEQ ID NO 112
<211> LENGTH: 117
<212> TYPE: PRT
<213> ORGANISM: Homo sapiens

<400> SEQUENCE: 112

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
                20                  25                  30

Trp Ile Gly Trp Val Arg Gln Met Pro Gly Lys Gly Leu Glu Trp Met
            35                  40                  45

Gly Ile Ile Ser Pro Thr Gly Ser Ala Thr Trp Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Tyr Lys Pro Phe Asp Val Trp Gly Gln Gly Thr Leu
                100                 105                 110

Val Thr Val Ser Ser
        115

<210> SEQ ID NO 113
<211> LENGTH: 109
<212> TYPE: PRT
<213> ORGANISM: Homo sapiens

<400> SEQUENCE: 113

Asp Ile Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ser Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Lys Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ser Glu Asp Glu Ala Asp Tyr Tyr Cys Ser Ser Trp Thr Pro Ser
                85                  90                  95

Ser Val Val Phe Gly Gly Gly Thr Lys Leu Thr Val Leu
                100                 105

<210> SEQ ID NO 114
<211> LENGTH: 111
<212> TYPE: PRT
<213> ORGANISM: Homo sapiens

<400> SEQUENCE: 114

Asp Ile Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ser Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Lys Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ser Glu Asp Glu Ala Asp Tyr Tyr Cys Ser Ser Trp Thr Asp Thr
                85                  90                  95

Pro Asn Met Ile Val Phe Gly Gly Thr Lys Leu Thr Val Leu
                100                 105                 110

<210> SEQ ID NO 115
<211> LENGTH: 111
<212> TYPE: PRT
<213> ORGANISM: Homo sapiens

<400> SEQUENCE: 115

Asp Ile Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ser Gly
            20                  25                  30

Tyr Asp Val His Trp Tyr Gln Gln Leu Pro Gly Thr Ala Pro Lys Leu
            35                  40                  45

-continued

```
Leu Ile Tyr Gly Asn Ser Lys Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ser Glu Asp Glu Ala Asp Tyr Tyr Cys Ala Ser Trp Thr Asp Gly
                 85                  90                  95

Leu Ser Leu Val Val Phe Gly Gly Gly Thr Lys Leu Thr Val Leu
            100                 105                 110

<210> SEQ ID NO 116
<211> LENGTH: 111
<212> TYPE: PRT
<213> ORGANISM: Homo sapiens

<400> SEQUENCE: 116

Gln Ser Val Leu Thr Gln Pro Pro Ser Val Ser Ala Pro Gly Gln
 1               5                  10                  15

Arg Val Thr Ile Ser Cys Thr Gly Ser Ser Asn Ile Gly Ser Gly
                 20                  25                  30

Tyr Asp Val His Trp Tyr Gln Gln Leu Pro Gly Thr Ala Pro Lys Leu
             35                  40                  45

Leu Ile Tyr Gly Asn Ser Lys Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ser Glu Asp Glu Ala Asp Tyr Tyr Cys Ala Ser Trp Thr Asp Gly
                 85                  90                  95

Leu Ser Leu Val Val Phe Gly Gly Gly Thr Lys Leu Thr Val Leu
            100                 105                 110

<210> SEQ ID NO 117
<211> LENGTH: 121
<212> TYPE: PRT
<213> ORGANISM: Homo sapiens

<400> SEQUENCE: 117

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Phe
                 20                  25                  30

Gly Met Ser Trp Val Arg Gln Ala Pro Gly Lys Gly Leu Glu Trp Val
             35                  40                  45

Ser Asn Ile Ser Ser Ser Gly Ser Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Trp Gly Thr Pro Tyr Leu Met Gln Phe Asp Asn Trp Gly
            100                 105                 110

Gln Gly Thr Leu Val Thr Val Ser Ser
        115                 120

<210> SEQ ID NO 118
<211> LENGTH: 123
<212> TYPE: PRT
<213> ORGANISM: Homo sapiens
```

<400> SEQUENCE: 118

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Asn Ile Glu His Lys Phe Met Gly Tyr Thr Thr Tyr Tyr Ala Ala
    50                  55                  60

Gly Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
            115                 120

<210> SEQ ID NO 119
<211> LENGTH: 123
<212> TYPE: PRT
<213> ORGANISM: Homo sapiens

<400> SEQUENCE: 119

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Glu His Lys Tyr Thr Gly Tyr Thr Thr Tyr Tyr Ala Ala
    50                  55                  60

Pro Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
            115                 120

<210> SEQ ID NO 120
<211> LENGTH: 123
<212> TYPE: PRT
<213> ORGANISM: Homo sapiens

<400> SEQUENCE: 120

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Asn Ile Glu His Lys Tyr Thr Ser Tyr Thr Thr Tyr Tyr Ala Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
        115                 120

<210> SEQ ID NO 121
<211> LENGTH: 123
<212> TYPE: PRT
<213> ORGANISM: Homo sapiens

<400> SEQUENCE: 121

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Asn Ile Glu His Lys Tyr Leu Asn Tyr Ala Thr Tyr Tyr Ala Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
        115                 120

<210> SEQ ID NO 122
<211> LENGTH: 123
<212> TYPE: PRT
<213> ORGANISM: Homo sapiens

<400> SEQUENCE: 122

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Asn Ile Glu His Lys Tyr Leu Gly Tyr Ala Thr Val Tyr Ala Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
        115                 120

<210> SEQ ID NO 123

```
<211> LENGTH: 123
<212> TYPE: PRT
<213> ORGANISM: Homo sapiens

<400> SEQUENCE: 123

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Glu His Lys Tyr Leu Ser Tyr Ala Thr Tyr Tyr Ala Ala
    50                  55                  60

Gly Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
            115                 120

<210> SEQ ID NO 124
<211> LENGTH: 123
<212> TYPE: PRT
<213> ORGANISM: Homo sapiens

<400> SEQUENCE: 124

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Glu His Lys Tyr Leu Ser Tyr Thr Thr Phe Tyr Ala Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Tyr Trp Gly Thr Pro Tyr Leu Met Gln Phe Asp Asn
            100                 105                 110

Trp Gly Gln Gly Thr Leu Val Thr Val Ser Ser
            115                 120

<210> SEQ ID NO 125
<211> LENGTH: 123
<212> TYPE: PRT
<213> ORGANISM: Homo sapiens

<400> SEQUENCE: 125

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45
```

Ser Gly Ile Glu His Lys Tyr Leu Ser Tyr Thr Thr His Tyr Ala Ala
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Tyr Trp Gly Thr Pro Tyr Leu Met Gln Phe Asp Asn
                100                 105                 110

Trp Gly Gln Gly Thr Leu Val Thr Val Ser Ser
            115                 120

<210> SEQ ID NO 126
<211> LENGTH: 123
<212> TYPE: PRT
<213> ORGANISM: Homo sapiens

<400> SEQUENCE: 126

Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Phe
                 20                  25                  30

Gly Met Ser Trp Val Arg Gln Ala Pro Gly Lys Gly Leu Glu Trp Val
             35                  40                  45

Ser Gln Ile Glu His Lys Tyr Leu Ser Tyr Thr Thr Leu Tyr Ala Ala
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Tyr Trp Gly Thr Pro Tyr Leu Met Gln Phe Asp Asn
                100                 105                 110

Trp Gly Gln Gly Thr Leu Val Thr Val Ser Ser
            115                 120

<210> SEQ ID NO 127
<211> LENGTH: 123
<212> TYPE: PRT
<213> ORGANISM: Homo sapiens

<400> SEQUENCE: 127

Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Phe
                 20                  25                  30

Gly Met Ser Trp Val Arg Gln Ala Pro Gly Lys Gly Leu Glu Trp Val
             35                  40                  45

Ser Gly Ile Glu His Lys Tyr Leu Ser Tyr Ala Thr Leu Tyr Ala Ala
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Tyr Trp Gly Thr Pro Tyr Leu Met Gln Phe Asp Asn
                100                 105                 110

Trp Gly Gln Gly Thr Leu Val Thr Val Ser Ser
            115                 120

<210> SEQ ID NO 128
<211> LENGTH: 111
<212> TYPE: PRT
<213> ORGANISM: Homo sapiens

<400> SEQUENCE: 128

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Ser Val Ser Ser Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Thr Asn
                85                  90                  95

Lys Pro Leu Val Val Phe Gly Gly Gly Thr Lys Leu Thr Val Leu
            100                 105                 110

<210> SEQ ID NO 129
<211> LENGTH: 111
<212> TYPE: PRT
<213> ORGANISM: Homo sapiens

<400> SEQUENCE: 129

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Ser Val Ser Ser Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Tyr Phe Tyr
                85                  90                  95

Leu Gln Arg Ile Val Phe Gly Gly Gly Thr Lys Leu Thr Val Leu
            100                 105                 110

<210> SEQ ID NO 130
<211> LENGTH: 111
<212> TYPE: PRT
<213> ORGANISM: Homo sapiens

<400> SEQUENCE: 130

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Ser Val Ser Ser Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Thr Tyr Tyr Phe Ser
                85                  90                  95

Tyr Ser Gly Pro Val Phe Gly Gly Gly Thr Lys Leu Thr Val Leu
            100                 105                 110

<210> SEQ ID NO 131
<211> LENGTH: 111
<212> TYPE: PRT
<213> ORGANISM: Homo sapiens

<400> SEQUENCE: 131

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Ser Val Ser Trp Tyr Gln Gln His Pro Gly Lys Ala Pro Lys Leu
            35                  40                  45

Met Ile Tyr Ser Val Ser Ser Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Asp Val Tyr
                85                  90                  95

Gly Arg Phe Tyr Val Phe Gly Gly Gly Thr Lys Leu Thr Val Leu
            100                 105                 110

<210> SEQ ID NO 132
<211> LENGTH: 111
<212> TYPE: PRT
<213> ORGANISM: Homo sapiens

<400> SEQUENCE: 132

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Ser Val Ser Trp Tyr Gln Gln His Pro Gly Lys Ala Pro Lys Leu
            35                  40                  45

Met Ile Tyr Ser Val Ser Ser Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Trp Asp Pro Ile
                85                  90                  95

Phe Ser Tyr Glu Val Phe Gly Gly Gly Thr Lys Leu Thr Val Leu
            100                 105                 110

<210> SEQ ID NO 133
<211> LENGTH: 381
<212> TYPE: DNA
<213> ORGANISM: Homo sapiens

<400> SEQUENCE: 133
caggtgcagc tggtgcagtc tggggctgag gtgaagaagc ctgggtcctc ggtgaaggtc      60
tcctgcaagg cttctggagg caccttcagc agcaactaca tcagctgggt gcgacaggcc     120

```
cctggacaag ggcttgagtg gatgggatc agccctggca ccggtatcaa cgcatactac    180
gcacagaagt tccagggcag agtcacgatt accgcggacg aatccacgag cacagcctac    240
atggagctga gcagcctgag atctgaggac acggccgtgt attactgtgc gagaagcaag    300
aagggcatgt acggcggctg gacctacccc ctgatgatgt tcgacctgtg gggccagggc    360
accctggtga ccgtgagcag c                                               381

<210> SEQ ID NO 134
<211> LENGTH: 381
<212> TYPE: DNA
<213> ORGANISM: Homo sapiens

<400> SEQUENCE: 134
caggtgcagc tggtgcagag cggcgccgag gtgaagaagc ccggcagcag cgtgaaggtg    60
agctgcaagg ccagcggcgg caccttcagc agcaactaca tcagctgggt gcgccaggcc    120
cccggccagg gcctggagtg gatgggcatc agccccggca ccggcatcaa cgcctactac    180
gcccagaagt tccagggccg cgtgaccatc accgccgacg agagcaccag caccgcctac    240
atggagctga gcagcctgcg cagcgaggac accgccgtgt actactgcgc cgcagcaag    300 aagggcatgt acgcggctg gacctacccc ctgatgatgt tcgacctgtg gggccagggc    360
accctggtga ccgtgagcag c                                               381

<210> SEQ ID NO 135
<211> LENGTH: 381
<212> TYPE: DNA
<213> ORGANISM: Homo sapiens

<400> SEQUENCE: 135
caggtgcaat tggttcagtc tggcgcggaa gtgaaaaaac cgggcagcag cgtgaaagtg    60
agctgcaaag cctccggagg cacttttttct tctaattata tttcttgggt gcgccaagcc    120
cctgggcagg gtctcgagtg gatgggcatt tctcctggta ctggtattaa tgcttattat    180
gctcagaagt ttcagggtcg ggtgaccatt accgcggatg aaagcaccag caccgcgtat    240
atggaactga gcagcctgcg tagcgaagat acggccgtgt attattgcgc gcgttctaag    300
aagggtatgt atggtggttg gacttatcct cttatgatgt ttgatctttg gggccaaggc    360
accctggtga cggttagctc a                                               381

<210> SEQ ID NO 136
<211> LENGTH: 324
<212> TYPE: DNA
<213> ORGANISM: Homo sapiens

<400> SEQUENCE: 136
gagatcgtgc tgacccagag cccgccacc ctgagcctga ccccggcga gcgcgccacc    60 ctgagctgcc gcgccagcca gagcgtgagc agcaactacc tggcctggta ccagcagaag    120
cccggccagg ccccccgcct gctgatctac tacgccagcc gccgcgccac cggcgtgccc    180
gcccgcttca gcggcagcgg cagcggcacc gacttcaccc tgaccatcag cagcctggag    240
cccgaggact tcgccgtgta ctactgccag cagaccagca cacccccctt caccttcggc    300
cagggcacca aggtggagat caag                                            324

<210> SEQ ID NO 137
<211> LENGTH: 324
<212> TYPE: DNA
```

<213> ORGANISM: Homo sapiens

<400> SEQUENCE: 137

| gaaattgtgt tgacacagtc tccagccacc ctgtctttgt ctccagggga aagagccacc | 60 |
| ctctcctgca gggccagtca gagtgttagc agcaactact tagcctggta ccaacagaaa | 120 |
| cctggccagg ctcccaggct cctcatctat tacgcatccc gcagggccac tggcgtgcca | 180 |
| gccaggttca gtggcagtgg gtctgggaca gacttcactc tcaccatcag cagcctagag | 240 |
| cctgaagatt ttgcagttta ttactgtcag cagacttcta atactccttt tacctttggc | 300 |
| cagggtacga aagttgaaat taaa | 324 |

<210> SEQ ID NO 138
<211> LENGTH: 324
<212> TYPE: DNA
<213> ORGANISM: Homo sapiens

<400> SEQUENCE: 138

| gagatcgtgc tgacccagag cccggcgacc ctgagcctgt ctccgggcga acgtgcgacc | 60 |
| ctgagctgca gagcgagcca gtctgtttct tctaattatc tggcttggta ccagcagaaa | 120 |
| ccaggtcaag caccgcgtct attaatttat tatgcttctc gtcgtgcaac tggggtcccg | 180 |
| gcgcgtttta gcggctctgg atccggcacg gattttaccc tgaccattag cagcctggaa | 240 |
| cctgaagact ttgcggtgta ttattgccag cagacttcta atactccttt tacctttggc | 300 |
| cagggtacga aagttgaaat taaa | 324 |

<210> SEQ ID NO 139
<211> LENGTH: 351
<212> TYPE: DNA
<213> ORGANISM: Homo sapiens

<400> SEQUENCE: 139

| gaggtgcagc tggtgcagtc tggagcagag gtgaaaaagc ccggggagtc tctgaagatc | 60 |
| tcctgtaagg gttctggata cagctttagc aactactgga tcggctgggt gcgccagatg | 120 |
| cccgggaaag gcctggagtg gatggggatc atcgacccta gcaactctta caccagatac | 180 |
| agcccgtcct tccaaggcca ggtcaccatc tcagccgaca gtccatcag caccgcctac | 240 |
| ctgcagtgga gcagcctgaa ggcctcgac accgccatgt attactgtgc gagatggtac | 300 |
| tacaagcccct tcgacgtgtg gggccagggc accctggtga ccgtgagcag c | 351 |

<210> SEQ ID NO 140
<211> LENGTH: 351
<212> TYPE: DNA
<213> ORGANISM: Homo sapiens

<400> SEQUENCE: 140

| gaggtgcagc tggtgcagag cggcgccgag gtgaagaagc ccggcgagag cctgaagatc | 60 |
| agctgcaagg gcagcggcta cagcttcagc aactactgga tcggctgggt gcgccagatg | 120 |
| cccggcaagg gcctggagtg gatgggcatc atcgaccca gcaacagcta cacccgctac | 180 |
| agccccagct ccagggcca ggtgaccatc agcgccgaca gagcatcag caccgcctac | 240 |
| ctgcagtgga gcagcctgaa ggccagcgac accgccatgt actactgcgc ccgctggtac | 300 |
| tacaagcccct tcgacgtgtg gggccagggc accctggtga ccgtgagcag c | 351 |

<210> SEQ ID NO 141
<211> LENGTH: 351

<212> TYPE: DNA
<213> ORGANISM: Homo sapiens

<400> SEQUENCE: 141

```
gaggtgcaat tggttcagag cggcgcggaa gtgaaaaaac cgggcgaaag cctgaaaatt      60
agctgcaaag gttccggata ttccttttct aattattgga ttggttgggt gcgccagatg     120
cctgggaagg gtctcgagtg gatgggcatt atcgatccgt ctaatagcta tacccgctat     180
tctccgagct ttcagggcca ggtgaccatt agcgcggata aaagcattag caccgcgtat     240
cttcaatgga gcagcctgaa agcgagcgat acggccatgt attattgcgc gcgttggtat     300
tataagcctt ttgatgtttg gggccaaggc accctggtga cggttagctc a              351
```

<210> SEQ ID NO 142
<211> LENGTH: 336
<212> TYPE: DNA
<213> ORGANISM: Homo sapiens

<400> SEQUENCE: 142

```
cagtctgtgc tgacgcagcc gcccctcagtg tctggggccc cagggcagag ggtcaccatc      60
tcctgcactg ggagcagctc caacatcggg agcggttatg atgtacactg gtaccagcag     120
cttccaggaa cagcccccaa actcctcatc tatggtaaca gcaagcggcc ctcaggggtc     180
cctgaccgat tctctggctc caagtctggc acctcagcct ccctggccat cactgggctc     240
cagagcgagg atgaggctga ttattactgc gccagctgga ccgacggcct gagcctggtg     300
gtgttcggcg gcggcaccaa gctgaccgtg ctgggc                               336
```

<210> SEQ ID NO 143
<211> LENGTH: 336
<212> TYPE: DNA
<213> ORGANISM: Homo sapiens

<400> SEQUENCE: 143

```
cagagcgtgc tgacccagcc ccccagcgtg agcggcgccc ccggccagcg cgtgaccatc      60
agctgcaccg gcagcagcag caacatcggc agcggctacg acgtgcactg gtaccagcag     120
ctgcccggca ccgcccccaa gctgctgatc tacggcaaca gcaagcgccc cagcggcgtg     180
cccgaccgct tcagcggcag caagagcggc accagcgcca gcctggccat caccggcctc     240
cagagcgagg acgaggccga ctactactgt gccagctgga ccgacggcct gagcctggtg     300
gtgttcggcg gcggcaccaa gctgaccgtg ctgggc                               336
```

<210> SEQ ID NO 144
<211> LENGTH: 336
<212> TYPE: DNA
<213> ORGANISM: Homo sapiens

<400> SEQUENCE: 144

```
cagagcgtgc tgacccagcc gccttcagtg agtggcgcac aggtcagcg tgtgaccatc      60
tcgtgtacgg gcagcagcag caacattggt tctggttatg atgtgcattg gtaccagcag     120
ttgcccggga cggcgccgaa acttctgatt tatggtaatt ctaagcgtcc ctcaggcgtg     180
ccggatcgtt ttagcggatc caaaagcggc accagcgcga gccttgcgat tacgggcctg     240
caaagcgaag acgaagcgga ttattattgc gcttcttgga ctgatggtct ttctcttgtt     300
gtgtttggcg gcggcacgaa gttaaccgtt cttggc                               336
```

<210> SEQ ID NO 145

```
<211> LENGTH: 189
<212> TYPE: PRT
<213> ORGANISM: Homo sapiens

<400> SEQUENCE: 145

Met Leu Gly Ser Arg Ala Val Met Leu Leu Leu Leu Pro Trp Thr
1               5                   10                  15

Ala Gln Gly Arg Ala Val Pro Gly Gly Ser Ser Pro Ala Trp Thr Gln
                20                  25                  30

Cys Gln Gln Leu Ser Gln Lys Leu Cys Thr Leu Ala Trp Ser Ala His
                35                  40                  45

Pro Leu Val Gly His Met Asp Leu Arg Glu Glu Gly Asp Glu Glu Thr
50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
                100                 105                 110

Pro Ser Leu Leu Pro Asp Ser Pro Val Ala Gln Leu His Ala Ser Leu
                115                 120                 125

Leu Gly Leu Ser Gln Leu Leu Gln Pro Glu Gly His His Trp Glu Thr
130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
                180                 185

<210> SEQ ID NO 146
<211> LENGTH: 19
<212> TYPE: PRT
<213> ORGANISM: Homo sapiens

<400> SEQUENCE: 146

Asn Ile Glu His Lys Tyr Leu Gly Tyr Ala Thr Ser Tyr Ala Ala Ser
1               5                   10                  15

Val Lys Gly

<210> SEQ ID NO 147
<211> LENGTH: 123
<212> TYPE: PRT
<213> ORGANISM: Homo sapiens

<400> SEQUENCE: 147

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
                35                  40                  45

Ser Asn Ile Glu His Lys Tyr Leu Gly Tyr Ala Thr Ser Tyr Ala Ala
                50                  55                  60

Ser Val Lys Gly Arg Phe Thr Ile Ser Arg Asp Asn Ser Lys Asn Thr
65                  70                  75                  80
```

```
Leu Tyr Leu Gln Met Asn Ser Leu Arg Ala Glu Asp Thr Ala Val Tyr
                85                  90                  95
Tyr Cys Ala Arg Tyr Trp Gly Thr Pro Tyr Leu Met Gln Phe Asp Asn
            100                 105                 110
Trp Gly Gln Gly Thr Leu Val Thr Val Ser Ser
        115                 120

<210> SEQ ID NO 148
<211> LENGTH: 12
<212> TYPE: PRT
<213> ORGANISM: Homo sapiens

<400> SEQUENCE: 148

His Gln Gly Leu Ile Phe Tyr Glu Lys Leu Leu Gly
1               5                   10
```

What is claimed is:

1. A method of treating Crohn's disease in a patient, comprising administering an antibody to IL-23 to the patient, wherein the antibody comprises a light chain variable region and a heavy chain variable region, said light chain variable region comprising:
   a complementarity determining region light chain 1 (CDRL1) amino acid sequence of SEQ ID NO:50;
   a CDRL2 amino acid sequence of SEQ ID NO:56; and
   a CDRL3 amino acid sequence of SEQ ID NO:73,
   said heavy chain variable region comprising:
   a complementarity determining region heavy chain 1 (CDRH1) amino acid sequence of SEQ ID NO:5;
   a CDRH2 amino acid sequence of SEQ ID NO:20; and
   a CDRH3 amino acid sequence of SEQ ID NO:44;
   and wherein the antibody is administered intravenously in three equal doses of: an initial dose, a second dose 4 weeks after the initial dose, and a third dose 8 weeks after the initial dose and the doses are selected from the group consisting of 200 mg, 600 mg and 1200 mg.

2. The method of claim 1, wherein the method further comprises administering a subcutaneous dose every 4 or 8 weeks after the dose at 8 weeks.

3. The method of claim 1, wherein the subcutaneous dose is 100 mg or 200 mg.

4. The method of claim 2, wherein the intravenous dose is 1200 mg and the subcutaneous dose is 200 mg every 4 weeks.

5. The method of claim 3, wherein the intravenous dose is 600 mg and the subcutaneous dose is 200 mg every 4 weeks.

6. The method of claim 3, wherein the intravenous dose is 200 mg and the subcutaneous dose is 100 mg every 8 weeks.

7. The method of claim 3, wherein the intravenous dose is 200 mg and the subcutaneous dose is 200 Mg every 4 weeks.

8. The method of claim 1, wherein the patient is a responder to the antibody and is identified as meeting at least two clinical endpoints selected from the group consisting of:
   (i) Change from Baseline in the Crohn's Disease Activity Index (CDAI) Score at Week 12;
   (ii) Clinical remission at Week 12, defined as CDAI less than (<) 150 points:
   (iii) Clinical response at Week 12, defined as greater than or equal to (>=) 100-point reduction from baseline in CDAI score or CDAI score <150;
   (iv) Patient-Reported Outcome (PRO)-2 Remission at Week 12 defined based on average daily stool frequency (SF) and average daily abdominal pain (AP) score;
   (v) Clinical-Biomarker Response at Week 12 defined using clinical response based on the CDAI score and reduction from baseline in C-reactive protein (CRP) or fecal calprotectin;
   (vi) Endoscopic Response at Week 12 measured by the Simple Endoscopic Score for Crohn's Disease (SES-CD) is based on the evaluation of 4 endoscopic components across 5 ileocolonic segments, with a total score ranging from 0 to 56;
   (vii) Clinical remission at Week 48 defined as CDAI score <150;
   (viii) Durable Clinical Remission at Week 48 defined as CDAI<150 for most of all visits between Week 12 and Week 48;
   (ix) Corticosteroid-Free Clinical Remission at Week 48 defined as CDAI score <150 at Week 48 and not receiving corticosteroids at Week 48;
   (x) PRO-2 remission at Week 48 defined based on average daily stool frequency (SF) and average daily abdominal pain (AP) score;
   (xi) Fatigue response at Week 12 based on the Patient-Reported Outcomes Measurement Information System (PROMIS) Fatigue Short Form 7a; and
   (xii) Endoscopic response at Week 48 measured by the Simple Endoscopic Score for Crohn's Disease (SES-CD).

9. The method of claim 6, wherein the antibody is in a composition comprising 7.9% (w/v) sucrose, 4.0 mM Histidine, 6.9 mM L-Histidine monohydrochloride monohydrate, and 0.053% (w/v) Polysorbate 80 of the composition, wherein the composition comprises a diluent of water at standard state.

10. The method of claim 1, further comprising administering to the patient one or more additional drugs used to treat Crohn's disease.

11. The method of claim 10, wherein the additional drug is selected from the group consisting of immunosuppressive agents, non-steroidal anti-inflammatory drugs (NSAIDs), methotrexate (MTX), anti-B-cell surface marker antibodies, anti-CD20 antibodies, rituximab, TNF-inhibitors, corticosteroids, and co-stimulatory modifiers.

12. The method of claim 1, wherein the antibody comprises a light chain variable region of the amino acid sequence of SEQ ID NO: 116 and a heavy chain variable region of the amino acid sequence of SEQ ID NO: 106.

13. The method of claim 1, wherein the antibody is guselkumab.

14. A method of treating Crohn's disease in a patient, comprising administering an antibody to IL-23 to the patient, wherein the antibody is guselkumab comprising a light chain variable region of the amino acid sequence of SEQ ID NO: 116 and a heavy chain variable region of the amino acid sequence of SEQ ID NO: 106, and wherein the antibody is administered in an initial intravenous dose of 200 mg, an intravenous dose of 200 mg 4 weeks after initial treatment, an intravenous dose of 200 mg 8 weeks after initial treatment, and a subcutaneous dose of 200 mg every 4 weeks thereafter.

15. A method of treating Crohn's disease in a patient, comprising administering an antibody to IL-23 to the patient, wherein the antibody is guselkumab comprising a light chain variable region of the amino acid sequence of SEQ ID NO: 116 and a heavy chain variable region of the amino acid sequence of SEQ ID NO: 106, and wherein the antibody is administered in an initial intravenous dose of 200 mg, an intravenous dose of 200 mg 4 weeks after initial treatment, an intravenous dose of 200 mg 8 weeks after initial treatment, and a subcutaneous dose of 100 mg every 8 weeks thereafter.

* * * * *